(12) United States Patent  (10) Patent No.: US 7,582,739 B2
Lukhtanov et al.  (45) Date of Patent: Sep. 1, 2009

(54) NEGATIVELY CHARGED MINOR GROOVE BINDERS

(75) Inventors: Eugeny A. Lukhtanov, Bothell, WA (US); Nicolaas M. J. Vermeulen, Woodinville, WA (US); Alexander A. Gall, Woodinville, WA (US)

(73) Assignee: Epoch Biosciences, Inc., Bothell, WA (US)

( * ) Notice: Subject to any disclaimer, the term of this patent is extended or adjusted under 35 U.S.C. 154(b) by 302 days.

(21) Appl. No.: 10/507,267

(22) PCT Filed: Mar. 11, 2003

(86) PCT No.: PCT/US03/07467

§ 371 (c)(1),
(2), (4) Date: Apr. 6, 2005

(87) PCT Pub. No.: WO03/078450

PCT Pub. Date: Sep. 25, 2003

(65) Prior Publication Data

US 2005/0187383 A1    Aug. 25, 2005

(51) Int. Cl.
*C07H 21/04*    (2006.01)
(52) U.S. Cl. ................................................. 536/23.1
(58) Field of Classification Search ............ None
See application file for complete search history.

(56) References Cited

U.S. PATENT DOCUMENTS 5,237,101 A    8/1993   Nicolaou et al.
5,446,137 A    8/1995   Maag et al.
5,493,012 A    2/1996   Rokita et al.
5,786,138 A    7/1998   Swenson
5,801,155 A    9/1998   Kutyavin et al.
5,955,590 A    9/1999   Levina et al.

(Continued)

FOREIGN PATENT DOCUMENTS

WO    WO 91/06556 A1    5/1991
WO    WO 92/20698 A1    11/1992

OTHER PUBLICATIONS

Bailly, Topoisomerase I Poisons and Suppressors as Anticancer Drugs, Current Medicinal Chemistry, 2000, 7, 39-58.*

(Continued)

*Primary Examiner*—Kenneth R. Horlick
*Assistant Examiner*—Mark Staples
(74) *Attorney, Agent, or Firm*—Townsend and Townsend and Crew LLP

(57) ABSTRACT

The present invention provides a negatively charged minor groove binding compound, oligonucleotide conjugates comprising the same, and methods for using the same. The negatively charged minor groove binding compounds of the present invention comprises an acidic moiety that is capable of being ionized under physiological conditions. In particular, the negatively charged minor groove binding compound of the present invention comprises a binding moiety that binds preferentially into a minor groove of a double, triple or higher stranded DNA, RNA, PNA or hybrids thereof. The binding moiety comprises at least one aryl moiety and an acidic moiety which is covalently attached to a phenyl portion of the aryl moiety or to a heteroatom of a heteroaryl portion of the aryl moiety.

32 Claims, 2 Drawing Sheets

U.S. PATENT DOCUMENTS

| | | | |
|---|---|---|---|
| 6,084,102 | A | 7/2000 | Kutyavin et al. |
| 6,312,894 | B1 | 11/2001 | Hedgpeth et al. |
| 6,426,408 | B1 | 7/2002 | Kutyavin et al. |
| 6,486,308 | B2 | 11/2002 | Kutyavin et al. |
| 6,492,346 | B1 | 12/2002 | Hedgpeth et al. |
| 6,790,945 | B2 * | 9/2004 | Lukhtanov et al. .......... 536/23.1 |
| 6,884,584 | B2 | 4/2005 | Hedgpeth et al. |
| 7,205,105 | B2 | 4/2007 | Afonina et al. |

OTHER PUBLICATIONS

Sinyakov et al., Stabilization of DNA Triple Helices Using Conjugates of Oligonucleotides and Synthetic Ligands, Molecular Biology, vol. 35, No. 2, 2001, pp. 251-260. Translated from Molekulyarnaya Biologiya, vol. 35, No. 2, 2001, pp. 298-308.*

Afonina, Irina et al.; "Sequence-specific arrest of primer extension on single-stranded DNA by an oligonucleotide-minor groove binder conjugate"; 1996, *PNAS*, vol. 93, pp. 3199-3204.

Afonina, Irina et al.; "Efficient priming of PCR with short oligonucleotides conjugated to a minor groove binder"; 1997, *Nucleic Acids Research*, vol. 25, No. 13, pp. 2657-2660.

Bailly, christian et al.; "DNA Recognition by Intercalator-Minor-Groove Binder Hybrid Molecules"; 1991, Bioconjugate Chemistry, vol. 2, No. 6.

Bailly, Christian et al.; "Sequence-Specific DNA Minor Groove Binders. Design and Synthesis of Netropsin and Distamycin Analogues"; 1991, Bioconjugate Chemistry, vol. 9, No. 5.

Boger, Dale L. et al.; "CC-1065 and the duocarmycins: Unraveling the keys to a new class of naturally derived DNA alkylating agents"; 1995, *PNAS*, vol. 92, pp. 3642-3649.

Kumar, Surat et al.; "Solution structure of a highly stable DNA duplex conjugated to a minor groove binder"; 1998, *Nucleic Acids Research*, vol. 26, No. 3, pp. 831-838.

Kutyavin, Igor V. et al.; "Oligonucleotides with conjugated dihydropyrroloindole tripeptides: base composition and backbone effects on hybridization"; 1997, *Nucleic Acids Research*, vol. 25, No. 18, pp. 3718-3723.

Lukhtanov, Eugeny A. et al.; "Oligodeoxyribonucleotides with Conjugated Dihydropyrroloindole Oligopeptides: Preparation and Hybridization Properties"; 1995, *Bioconjugate Chemistry*, vol. 6, pp. 418-426.

Lukhtanov, Eugeny A. et al.; "Rapid and efficient hybridization-triggered crosslinking within a DNA duplex by an oligodeoxyribonucleotide bearing a conjugated cyclopropapyrroloindole"; 1996, *Nucleic Acids Research*, vol. 24, No. 4, pp. 683-687.

Lukhtanov, Eugeny A. et al.; "Monor groove DNA alkylation directed by major groove triplex forming oligodeoxyribonucleotides"; 1997, *Nucleic Acids Research*, vol. 25, No. 24, pp. 5077-5084.

Lukhtanov, Eugeny A. et al.; "Sequence and Structure Dependence of the Hybridization-Triggered Reacton of Olibonucleotides Bearing Conjugated Cyclopropapyrroloindole"; *Journal of the American Chemical Society*, vol. 119, No. 27, pp. 6214-6225.

Lukhtanov, Eugeny A. et al.; "Direct, Solid Phase Assembly of Dihydropyrroloindole Peptides with COnjugated Oligonucleotides"; *Bioconjugate Chemistry*, vol. 7, No. 5, pp. 564-567.

O'Donnell, Maryanne J. et al.; "Synthesis and Properties of a Hoechst-Like Minor-Groove Binding Agent Tethered to an Oligodeoxynucleotide"; 1995, *Bioorganic & Medicinal Chemistry*, vol. 3, No. 6, pp. 743-750.

Robles, Jordi et al.; "A Parallel-Standed DNA Triplex Tethering a Hoechst 33258 Analogue Results in Complex Stablization by Simultaneous Major Groove and Minor Groove Binding"; 1996, *J. Am. Chem. Soc.*, vol. 118, pp. 5820-5821.

Robles, Jordi et al.; "DNA Triplex Stablization Using a Tethered Minor Groove Binding Hoechst 33258 Analogue"; 1997, *J. Am. Chem. Soc.*, vol. 119, pp. 6014-6021.

Sinyakov, Alexander N. et al.; "Exceptional and Selective Stabilization of A-T Rich DNA-DNA Duplexes by N-Methylpyrrole Carboxamide Peptides Conjugated to Oligodeoxynucleotides"; 1995, The Journal of the American Chemical Society.

Wiederholt, Kristin et al.; "DNA-Tethered Hoechst Groove-Binding Agents: Duplex Stabilization and Fluorescence Characteristics"; 1996, American Chemical Society.

* cited by examiner

SEQUENCE LISTING

```
<160> NUMBER OF SEQ ID NOS: 6

<210> SEQ ID NO 1
<211> LENGTH: 10
<212> TYPE: DNA
<213> ORGANISM: Artificial Sequence
<220> FEATURE:
<223> OTHER INFORMATION: synthetic oligonucleotide conjugate
<221> NAME/KEY: modified_base
<222> LOCATION: (10)...(10)
<223> OTHER INFORMATION: c conjugated to minor groove binder X-11
      (CDPI-3 (C), CDPI-3-SO-3, CDPI-3 (N) or CDPI-4-SO-3)-2)

<400> SEQUENCE: 1
ccaaaattac                                                           10

<210> SEQ ID NO 2
<211> LENGTH: 10
<212> TYPE: DNA
<213> ORGANISM: Artificial Sequence
<220> FEATURE:
<223> OTHER INFORMATION: 3'-conjugated PCR complementary target
      oligonucleotide (ODN) #1
<221> NAME/KEY: modified_base
<222> LOCATION: (10)...(10)
<223> OTHER INFORMATION: g conjugated to minor groove binder X (CDPI-3
      (C), CDPI-3 (N) or CDPI-4-SO-3)-2)

<400> SEQUENCE: 2
ggttttaatg                                                           10

<210> SEQ ID NO 3
<211> LENGTH: 10
<212> TYPE: DNA
<213> ORGANISM: Artificial Sequence
<220> FEATURE:
<223> OTHER INFORMATION: 3'-conjugated PCR complementary target
      containing A/C mismatch oligonucleotide (ODN) #0
<221> NAME/KEY: modified_base
<222> LOCATION: (10)...(10)
<223> OTHER INFORMATION: g conjugated to minor groove binder X (CDPI-3
      (C), CDPI-3 (N) or CDPI-4-SO-3)-2)

<400> SEQUENCE: 3
ggtttcaatg                                                           10
```

```
<210> SEQ ID NO 4
<211> LENGTH: 10
<212> TYPE: DNA
<213> ORGANISM: Artificial Sequence
<220> FEATURE:
<223> OTHER INFORMATION: 3'-conjugated PCR complementary target
      containing A/C mismatch oligonucleotide (ODN) #2
<221> NAME/KEY: modified_base
<222> LOCATION: (10)...(10)
<223> OTHER INFORMATION: g conjugated to minor groove binder X (CDPI-3
      (C), CDPI-3 (N) or CDPI-4-SO-3)-2)

<400> SEQUENCE: 4
ggttctaatg                                                              10

<210> SEQ ID NO 5
<211> LENGTH: 10
<212> TYPE: DNA
<213> ORGANISM: Artificial Sequence
<220> FEATURE:
<223> OTHER INFORMATION: 3'-conjugated PCR complemetary target
      containing A/C mismatch oligonucleotide (ODN) #3
<221> NAME/KEY: modified_base
<222> LOCATION: (10)...(10)
<223> OTHER INFORMATION: g conjugated to minor groove binder X (CDPI-3
      (C), CDPI-3 (N) or CDPI-4-SO-3)-2)

<400> SEQUENCE: 5
ggtcttaatg                                                              10

<210> SEQ ID NO 6
<211> LENGTH: 10
<212> TYPE: DNA
<213> ORGANISM: Artificial Sequence
<220> FEATURE:
<223> OTHER INFORMATION: 3'-conjugated PCR complementary target
      containing A/C mismatch oligonucleotide (ODN) #4
<221> NAME/KEY: modified_base
<222> LOCATION: (10)...(10)
<223> OTHER INFORMATION: g conjugated to minor groove binder X (CDPI-3
      (C), CDPI-3 (N) or CDPI-4-SO-3)-2)

<400> SEQUENCE: 6
ggctttaatg                                                              10
```

NEGATIVELY CHARGED MINOR GROOVE BINDERS

FIELD OF THE INVENTION

The present invention relates to a negatively charged minor groove binder or salts thereof.

BACKGROUND OF THE INVENTION

Intercalating agents that bind to double stranded oligonucleotides (e.g., DNA, RNA or hybrids thereof) are well known in the art. In general, intercalating agents are aromatic molecules that non-covalently bind to double stranded oligonucleotides by intercalating themselves between interfacing purine and pyrimidine bases of the two strands of double stranded oligonucleotides. Thus, oligonucleotides carrying, i.e., connected to, an intercalating group can be used in a variety of applications, including as hybridization probes.

Similarly, minor groove binding agents are compounds that bind non-covalently into the minor groove of a double stranded oligonucleotides. However, minor groove binding agents are generally higher molecular weight molecules than intercalating agents. Typically, the molecular weight of minor groove binder agents range from about 150 to about 2000 Daltons. Minor groove binding agents generally bind in a non-intercalating manner into the minor groove of double stranded oligonucleotides. Thus, minor groove binding agents can be used for duplex stabilization and are useful as hybridization improving tools, as well as other applications. For example, hybridization reagents comprising a covalently attached oligonucleotides and minor groove binders are described in U.S. Pat. No. 6,321,894. In addition, using minor groove binders in sequence specific binding and melting temperature modulation have been described in U.S. Pat. Nos. 6,303,312 and 6,221,589, respectively.

Minor groove binder agents usually have a chain of connected (conjugated or non-conjugated) aromatic rings. The presence of a plurality of aromatic rings renders the minor groove binders prone to self-association (aggregation) due to the pi-interaction between the aromatic systems. Aggregation reduces effective concentration of the minor groove binders (poorly soluble) and consequently their minor groove binding performance. One method for reducing non-specific self-associations is to introduce an electrostatic charge within the minor groove binders. Some minor groove binding compounds bearing positive charges at the terminal position of the molecules are known. See, for example, Reddy et al., *Pharmacol. Therapeut.*, 1999, 84, 1-111. The positive charge improves the attraction to the negatively charged DNA duplexes thereby increasing the DNA binding affinity. Unfortunately, however, the positive charge can also increase non-specific binding.

Therefore, there is a need for minor groove binding compounds with reduced self-associations and non-specific binding.

SUMMARY OF THE INVENTION

Some aspects of the present invention are based on a negatively charged minor groove binding (NMGB) compound that binds preferentially into a minor groove of a double, triple or higher stranded oligonucleotides, e.g., DNA, RNA, PNA or hybrids thereof. Preferably, the negatively charged minor groove binding compound binds to the oligonucleotide duplex in a non-intercalating manner.

In one aspect of the present invention, an oligonucleotide-negatively charged minor groove binder conjugate is provided. The conjugate comprises:

a negatively charged minor groove binder moiety comprising:
   at least one aryl moiety, and
   at least one acidic moiety capable of ionizing under physiological conditions, wherein said acidic moiety is covalently attached to at least one of said aryl moiety and optionally comprises an acidic moiety linker; and
an oligonucleotide moiety which is covalently attached to said negatively charged minor groove binder moiety.

The negatively charged minor groove binder moiety can be covalently attached to any portion of the oligonucleotide. In one embodiment, the negatively charged minor groove binder moiety is attached to 3'-position, 5'-position or an internal sugar moiety of the oligonucleotide. In another embodiment, the negatively charged minor groove binder moiety is covalently attached to a heterocyclic base portion of the oligonucleotide moiety.

The negatively charged minor groove binder moieties of the present invention comprise one or more acidic moieties. In one embodiment, the negatively charged minor groove binder moiety comprises two or more acidic moieties, preferably at least three acidic moieties.

Preferably, the aryl moiety of negatively charged minor groove binder is selected from the group consisting of phenyl, a heteroaryl, a fused phenyl-heteroaryl, a fused heteroaryl-phenyl-heterocyclyl and a combination thereof.

In one embodiment, the acidic moiety is covalently attached to a phenyl moiety or a heteroatom of a heteroaryl portion of the aryl moiety, optionally through the acidic moiety linker. While any acidic moiety which is capable of ionizing under physiological condition can be used in the present invention, in one particular embodiment, the acidic moiety has pKa of about 6 or less. Preferably, each of the acidic moiety is independently selected from the group consisting of:

(i) $-(O)_d S(O)_e OH$, wherein d is 0 or 1 and e is 1 or 2, and
(ii) $-(O)_f P(O)_g (OR^{a1})_h (OH)_i$, wherein each $R^{a1}$ is independently selected from the group consisting of alkyl, aralkyl and aryl; f is 0 or 1; each of g and h is independently 0, 1, or 2; and i is 1, 2 or 3, provided the sum of g+h+i is 2 or 3;
(iii) $-CO_2 H$; and
(iv) salts thereof.

More preferably, each of the acidic moiety is independently selected from the group consisting of $-SO_2 OH$, $-OPO_2(OH)$, $-CO_2 H$, and salts thereof.

In another embodiment, at least one of the acidic moiety is covalently attached to at least one of said aryl moiety through the acidic moiety linker. Preferably, the acidic moiety linker comprises a chain of atoms. Such chain of atoms can be arranged in a variety of manners such as cyclic, acyclic, aryl or a combination thereof of. Preferably, the backbone of the acidic moiety linker chain comprises from 1 to about 30 atoms. Each of the backbone atom is independently selected from the group consisting of C, N, O, S, P. In addition, each of these backbone atoms can be substituted with appropriate substituents known to one skilled in the art. For example, carbon atom can be substituted with a hydrogen, carbonyl oxygen, alkoxy, halide, amine, amide, cyano, hydroxyl. And sulfur and phosphorous atoms can be substituted with one or more oxygen atoms. Preferably, carbon atoms of the chain backbone are independently substituted with hydrogen or carbonyl oxygen.

In one particular embodiment, the acidic moiety linker is of the formula:

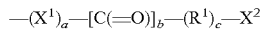
—(X¹)ₐ—[C(=O)]ᵦ—(R¹)ᶜ—X² wherein
each of a, b and c is independently 0 or 1;
each $X^1$ is independently selected from the group consisting of:
(i) O,
(ii) $NR^2$, where each $R^2$ is independently selected from the group consisting of hydrogen, alkyl, cycloalkyl and a nitrogen protecting group, and
(iii) alkylene;
each $R^1$ is independently selected from the group consisting of alkylene, cycloalkylene, arylene and a combination thereof; and
each $X^2$ is independently said acid moiety.

The number of nucleotide units present in the oligonucleotide moiety can vary depending on a variety of factors. In one embodiment, the oligonucleotide moiety comprises from 3 to about 100 nucleotide units. However, it should be appreciated that the present invention is not limited to this particular number of nucleotide units in the oligonucleotide moiety.

Still in another embodiment, the oligonucleotide-negatively charged minor groove binder conjugate comprises a covalently attached fluorophore moiety. The fluorophore moiety can be attached to any portion of the conjugate, including the negatively charged minor groove binder or a linker, if present. In addition, more than one fluorophore moiety can be present in the conjugate. Preferably, the fluorophore is covalently attached to the oligonucleotide moiety optionally via a second linker moiety.

While any conventionally known fluorophores are suitable in oligonucleotide-negatively charged minor groove binder conjugates of the present invention, preferred fluorophores includes those with the emission wavelength of from about 400 to about 1000 nm.

In one embodiment, the negatively charged minor groove binder moiety is covalently attached to the oligonucleotide moiety through a first linker moiety. The first linker moiety can also comprise a covalently attached quencher moiety. Preferably, the quencher moiety is compatible with the fluorophore moiety such that the emission wave of the fluorophore moiety is absorbed by the quencher moiety. In one embodiment, the absorbance maximum of the quencher moiety is from about 400 nm to about 1000 nm.

In one specific embodiment of the present invention, the oligonucleotide-negatively charged minor groove binder conjugate is of the formula:

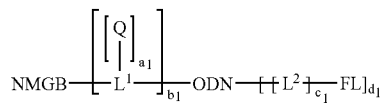

wherein
NMGB is said negatively charged minor groove binder;
ODN is said oligonucleotide;
FL is a fluorophore;
Q is a quencher;
$L^1$ is a first linker comprising a chain of from 3 to about 100 atoms selected from the group consisting of C, N, O, S, P and combinations thereof;

$L^2$ is a second linker comprising a chain of from 1 to about 30 atoms selected from the group consisting of C, N, O, S, P and combinations thereof; and
each of $a_1$, $b_1$, $c_1$ and $d_1$ is independently 0 or 1.

In one embodiment, the negatively charged minor groove binder moiety is of the formula:

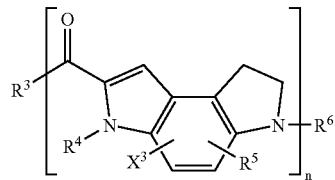

wherein
n is an integer from 2 to 10;
$R^3$ is selected from the group consisting of:
(a) alkoxy,
(b) aryloxy,
(c) $R^a$—O—$L^3$—N($R^b$)—, where $L^3$ is a third linker comprising a chain of from 3 to 20 atoms selected from the group consisting of C, N, O, S, P and combinations thereof; and $R^a$ is hydrogen, a hydroxyl protecting group or it is attached to the first linker $L^1$; and $R^b$ is hydrogen, alkyl, cycloalkyl or a nitrogen protecting group,
(d) a moiety of the formula:

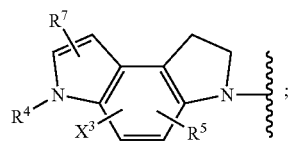

where
each of $X^3$ is independently selected from the group consisting of hydrogen, alkyl, alkoxy, halide, cyano, nitro, said acidic moiety optionally comprising an acidic linker and —$NR^{b1}$—C(=O)$R^c$, where each $R^{b1}$ is hydrogen, alkyl, cycloalkyl or a nitrogen protecting group, each $R^c$ is independently selected from the group consisting of hydrogen, alkyl, and cycloalkyl;
each of $R^4$ is independently selected from the group consisting of:
(a) hydrogen,
(b) alkyl,
(c) the acidic moiety optionally comprising an acidic moiety linker,
(d) —C(=O)—$R^{71}$, where $R^{71}$ is hydrogen, alkyl, hydroxy or alkoxy,
(e) —NR'R", where each of R' and R" is independently hydrogen or alkyl, and
(f) -(alkylene)-$OR^{72}$, where $R^{72}$ is hydrogen or alkyl,
each $R^5$ is independently selected from the group consisting of:
(a) hydrogen,
(b) alkyl,
(c) alkoxy,
(d) cycloalkyl,
(e) halide,
(f) cyano,
(g) nitro,
(h) —$[X^4]_{m1}$—C(=O)—$[O]_{m2}$—$R^8$, wherein each of the subscripts m1 and m2 is independently 0 or 1, $X^4$ is O, $NR^{b1}$, where $R^{b1}$ is hydrogen, alkyl, cycloalkyl or a nitrogen protecting group and $R^8$ is hydrogen, alkyl or cycloalkyl, provided when m2 is 1, $R^8$ is alkyl or cycloalkyl, and
(i) —C(=O)—$NR^eR^f$, where each of $R^e$ and $R^f$ is independently hydrogen, alkyl, cycloalkyl and a nitrogen protecting group,
(j) the acidic moiety optionally comprising an acidic moiety linker,
(k) —NR'R", where each of R' and R" is independently hydrogen or alkyl, and
(l) -(alkylene)-$OR^{72}$, where $R^{72}$ is hydrogen or alkyl;

each of $R^6$ and $R^7$ is selected from the group consisting of:
(a) hydrogen,
(b) alkyl,
(c) cycloalkyl,
(d) -$L^x$-$Z^x$, where $L^x$ is a linker comprising from 3 to 20 atoms selected from the group consisting of C, N, O, S, P and combinations thereof; $Z^x$ is hydrogen, a protecting group, a solid support or a point of attachment to said first linker $L^1$,
(e) the acidic moiety optionally comprising an acidic moiety linker, and
(f) a moiety of the formula -$(Z^1)_j$-C(=O)—$(R^{10})_k$—[C(=O)]$_l$—$R^{11}$,
where
each of j, k and l is independently 0 or 1;
each $Z^1$ is independently selected from the group consisting of O, $NR^{12}$ and alkylene;
each $R^{10}$ is independently selected from the group consisting of alkylene and cycloalkylene;
each $R^{11}$ is independently selected from the group consisting of alkyl, alkoxy, aryloxy, —$NR^{13}R^{14}$, —$NR^{15}$—$NR^{16}R^{17}$, hydroxyalkyl and thioalkyl; and
each of $R^{12}$, $R^{13}$, $R^{14}$, $R^{15}$, $R^{16}$, and $R^{17}$ is independently selected from the group consisting of hydrogen, alkyl, cycloalkyl and a nitrogen protecting group;
(g) —NR'R", where each of R' and R" is independently hydrogen or alkyl;
(h) -(alkylene)-$OR^{72}$, where $R^{72}$ is hydrogen or alkyl; and
(i) —CHO provided at least one of $X^3$, $R^4$, $R^6$, or $R^7$ comprises said acidic moiety optionally comprising said acidic moiety linker, and provided that one of $R^3$, $R^6$, $R^7$ and $R^a$ is a point of attachment to said first linker $L^1$. The negatively charged minor groove binding (i.e., NMGB) moiety can be part of or attached to $R^3$ moiety and/or $R^6$ moiety. Furthermore, the NMGB can be attached to any portion of the sugar moiety, e.g., the 3'- or 5'-position.

In another embodiment, the negatively charged minor groove binder moiety is of the formula:

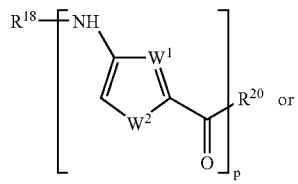

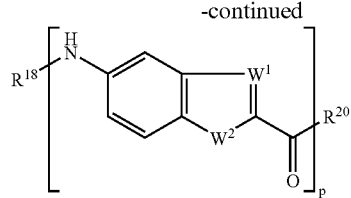

wherein
$W^1$ is N or $CR^{x30}$, where $R^{x30}$ is hydrogen, alkyl, or hydroxy, preferably $R^{x30}$ is hydrogen, methyl, hydroxy or trifluoromethyl;
$W^2$ is $NR^{19}$, S or O;
p is an integer from 2 to 12;
each $R^{19}$ is independently selected from the group consisting of:
(a) hydrogen,
(b) alkyl,
(c) a nitrogen protecting group, and
(b) said acidic moiety optionally comprising an acidic moiety linker;
each of $R^{18}$ and $R^{20}$ is independently selected from the group consisting of:
(a) hydrogen,
(b) alkyl,
(c) cycloalkyl,
(d) said acidic moiety; and
(e) -$(Z^1)_j$-C(=O)—$(R^{10})_k$—[C(=O)]$_l$—$R^{11}$,
where j, k, l, $Z^1$, $R^{10}$, $R^{11}$ are those define above;

provided at least one of $R^{18}$, $R^{19}$ or $R^{20}$ is said acidic moiety, optionally comprising said acidic moiety linker, and provided that one of $R^{18}$ and $R^{20}$ is a point of attachment to said first linker $L^1$. Preferably, the negatively charged minor groove binder moiety is of the formula:

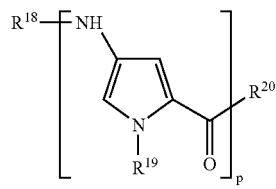

Yet in another embodiment, the negatively charged minor groove binder moiety is of the formula:

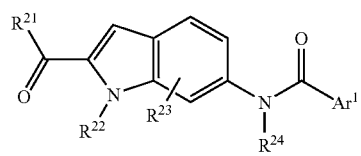

wherein
$R^{21}$ is an optionally substituted aryl-heterocyclyl;
each of $R^{22}$ and $R^{24}$ is independently selected from the group consisting of hydrogen, alkyl, cycloalkyl and a nitrogen protecting group;
$Ar^1$ is optionally substituted aryl moiety; and
$R^{23}$ is selected from the group consisting of hydrogen and said acidic moiety optionally comprising said acidic moiety linker, provided when $R^{23}$ is hydrogen at least one of $Ar^1$ or $R^{21}$ is substituted with said acidic moiety optionally comprising said acidic moiety linker, and provided that one of $R^{21}$, $R^{22}$, $R^{23}$ and $R^{24}$ is a point of attachment to said first linker $L^1$.

In one particular embodiment, the quencher moiety is a diazo moiety. Preferably, a diazo moiety of the formula:

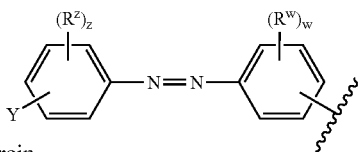

wherein
Y is selected from the group consisting of substituted phenyldiazenyl, nitro and —NR$^{50}$R$^{51}$, where each of R$^{50}$ and R$^{51}$ is independently selected from the group consisting of hydrogen, alkyl, cycloalkyl and a nitrogen protecting group;
each of z and w is independently an integer from 0 to 4;
each R$^z$ is independently selected from the group consisting of hydrogen, nitro, cyano, halide and —S(O)$_{aa}$NR$^{52}$R$^{53}$, where aa is 0, 1 or 2 and each of R$^{52}$ and R$^{53}$ is independently selected from the group consisting of hydrogen, alkyl, cycloalkyl and a nitrogen protecting group, or two adjacent R$^z$'s and carbon atom to which they are attached to forms a five- or six-membered ring having from zero to three heteroatoms as ring members; and
each R$^w$ is independently selected from the group consisting of alkoxy, halide and —NR$^{54}$—C(=O)R$^{55}$, where R$^{54}$ is selected from the group consisting of hydrogen, alkyl and a nitrogen protecting group, and R$^{55}$ is selected from the group consisting of hydrogen, alkyl and cycloalkyl, or two adjacent R$^w$'s and carbon atom to which they are attached to forms a five- or six-membered ring having from zero to three heteroatoms as ring members.

In one particular embodiment, the quencher moiety is of the formula:

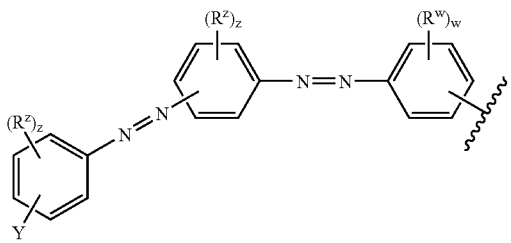

where Y, w, z, R$^w$ and R$^z$ are those defined herein.

In one embodiment, the quencher moiety is of the formula:

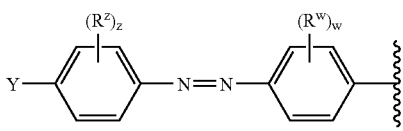

where w, z, R$^w$ and R$^z$ are those defined herein; and Y is selected from the group consisting of nitro and —N(CH$_3$)$_2$.

In one particular embodiment, the fluorophore moiety, FL, is selected from the group consisting of:

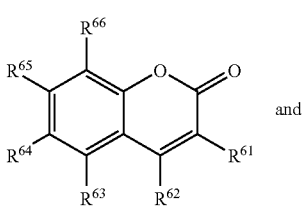

and

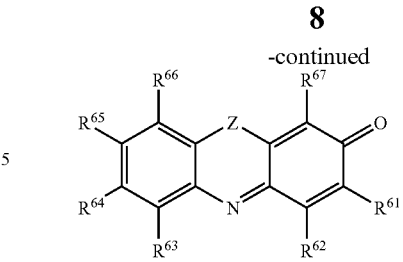

wherein
each of R$^{61}$, R$^{62}$, R$^{63}$, R$^{64}$, R$^{65}$, R$^{66}$ and R$^{67}$ is independently selected from the group consisting of hydrogen, halide, nitro, cyano, SO$_3$R$^{70}$, SO$_2$N(R$^{70}$)$_2$, C(O)OR$^{70}$, C(O)N(R$^{70}$)$_2$, CNS, —OR$^{70}$, —OC(O)R$^{70}$, —SR$^{70}$, —CF$_3$, —NHC(O)R$^{70}$, —N(R$^{70}$)$_2$, wherein each R$^{70}$ is independently selected from the group consisting of hydrogen, C$_1$-C$_8$ alkyl, aryl and a protecting group compatible with oligonucleotide synthesis, or
two adjacent groups of R$^{61}$ through R$^{66}$ together with the carbon atoms to which they are attached form a five- or six-membered ring having from zero to three heteroatoms as ring member; and
Z is O or S;

provided that at least one of R$^{61}$ through R$^{67}$ is a point of attachment to said second linker L$^2$ or to said oligonucleotide ODN.

In one embodiment, the first linker, L$^1$, is selected from the group consisting of moieties the formula:

(a)

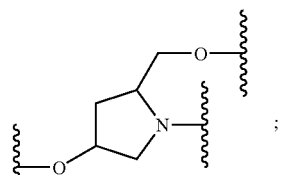

(b)

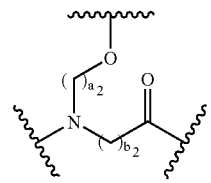

where a$_2$ and b$_2$ are independently an integer from 2 to 10;

(c)

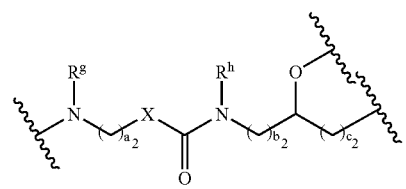

where a$_2$, b$_2$ and c$_2$ are independently an integer from 2 to 10, X is O, CH$_2$ or NR$^i$ and each of R$^g$, R$^h$ and R$^i$ is independently hydrogen, alkyl, cycloalkyl or a nitrogen protecting group; and (d)

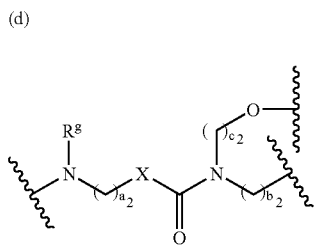

(L-4)

where $a_2$, $b_2$ and $c_2$ are independently an integer from 2 to 10, X is O, $CH_2$ or $NR^i$ and each of $R^g$ and $R^i$ is independently hydrogen, alkyl, cycloalkyl or a nitrogen protecting group.

Another aspect of the present invention provides a negatively charged minor groove binding compound comprising a binding moiety that binds preferentially into a minor groove of a double stranded oligonucleotide, wherein said binding moiety comprises:

at least one aryl moiety, and at least one acidic moiety capable of ionizing under physiological conditions, wherein said acidic moiety is covalently attached to a phenyl moiety of said aryl moiety or a heteroatom of a heteroaryl portion of said aryl moiety, wherein said acidic moiety optionally comprises an acidic moiety linker.

In one embodiment, the aryl moiety is selected from the group consisting of phenyl, a heteroaryl, a fused phenyl-heteroaryl, a fused heteroaryl-phenyl-heterocyclyl and a combination thereof. Preferably, each of the aryl moiety is independently selected from the group consisting of indole, benzofuran, pyrroloindole, hydropyrroloindole, phenyl, pyrrole, benzimidazole, imidazole, pyridine, 6-phenylimidazo[4,5-b]pyridine, furan, thiazole and oxazole.

In one embodiment, the binding moiety comprises a plurality of aryl moieties. Preferably, at least three aryl moieties.

In one particular embodiment, the negatively charged minor groove binding compound is of the formula:

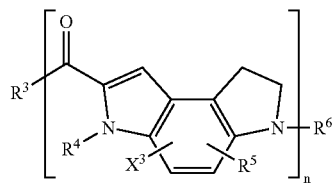

wherein n, $R^3$, $R^4$, $R^5$, $R^6$ and $X^3$ are those defined above, provided at least one of $X^3$, $R^4$, $R^6$ and $R^7$ is an acidic moiety optionally comprising an acidic moiety linker.

In another embodiment, the negatively charged minor groove binding compound is of the formula:

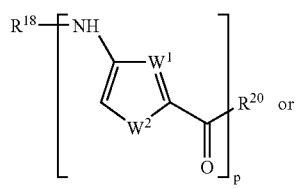

-continued

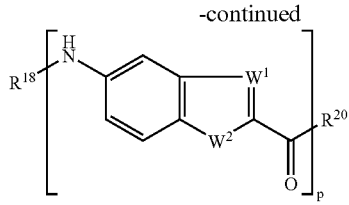

where p, $R^{18}$, $R^{20}$, $W^1$ and $W^2$ are those defined herein, provided at least one of $R^{18}$, $R^{19}$ (when $W^2$ is $NR^{19}$) or $R^{20}$ is an acidic moiety, optionally comprising an acidic moiety linker. In this embodiment, the negatively charged minor groove binding compound is preferably of the formula:

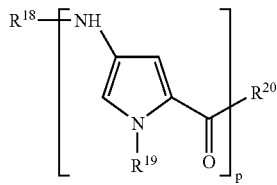

where p, $R^{18}$, $R^{19}$ and $R^{20}$ are those defined herein, provided at least one of $R^{18}$, $R^{19}$ or $R^{20}$ is an acidic moiety, optionally comprising an acidic moiety linker.

Yet in another embodiment, the negatively charged minor groove binding compound is of the formula:

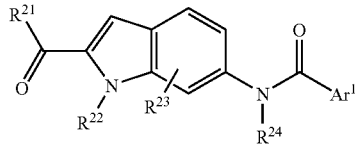

where $R^{21}$, $R^{22}$, $R^{23}$, $R^{24}$ and $Ar^1$ are those defined herein, provided when $R^{23}$ is hydrogen at least one of $Ar^1$ or $R^{21}$ is substituted with an acidic moiety, optionally comprising an acidic moiety linker. Preferably, $R^{22}$, $R^{24}$ and $R^{25}$ are hydrogen.

In one particular embodiment, $R^{21}$ is selected from the group consisting of:

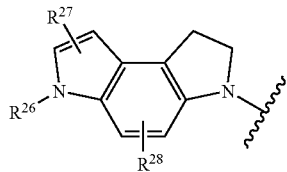

wherein $R^{26}$ is selected from the group consisting of hydrogen, alkyl, and a nitrogen protecting group;

$R^{27}$ is selected from the group consisting of:
(a) hydrogen,
(b) alkyl,
(c) cycloalkyl,
(d) said acidic moiety, optionally comprising said acidic moiety linker,
(e) $-(Z^1)_j-C(=O)-(R^{10})_k-[C(=O)]_l-R^{11}$,
where
each of j, k and l is independently 0 or 1;
each $Z^1$ is independently selected from the group consisting of O, $NR^{12}$ and alkylene;

each $R^{10}$ is independently selected from the group consisting of alkylene and cycloalkylene;

each $R^{11}$ is independently selected from the group consisting of alkyl, alkoxy, aryloxy, —$NR^{13}R^{14}$, $NR^{15}$—$NR^{16}R^{17}$, hydroxyalkyl and thioalkyl; and each of $R^{12}$, $R^{13}$, $R^{14}$, $R^{15}$, $R^{16}$, and $R^{17}$ is independently selected from the group consisting of hydrogen, alkyl, cylcoalkyl, and a nitrogen protecting group, and (f) -$L^xZ^x$, where $L^x$ is a linker comprising from 3 to 20 atoms selected from the group consisting of C, N, O, S, P and combinations thereof, and $Z^x$ is selected from the group consisting of hydrogen, a protecting group or a solid support; and $R^{28}$ is selected from the group consisting of hydrogen and said acidic moiety optionally comprising said acidic moiety linker.

In one embodiment, $Ar^1$ is selected from the group consisting of:

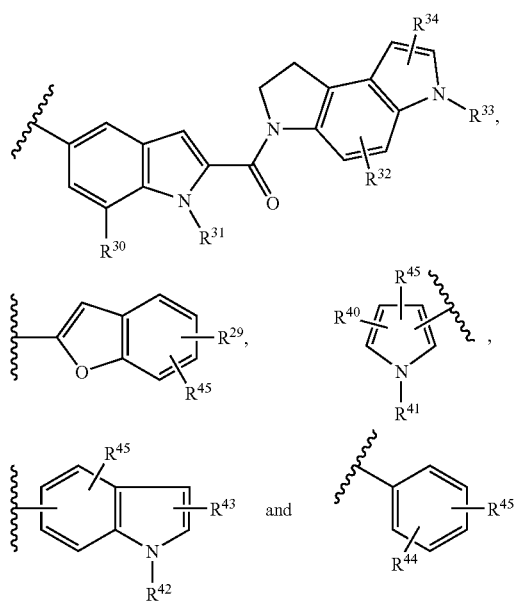

wherein each of $R^{29}$, $R^{30}$ and $R^{32}$ is independently selected from the group consisting of hydrogen and said acidic moiety, optionally comprising said acidic moiety linker;

$R^{34}$ is selected from the group consisting of:
(a) hydrogen,
(b) alkyl,
(c) cycloalkyl,
(d) said acidic moiety, optionally comprising said acidic moiety linker,
(e) -$(Z^1)_j$-C(=O)—$(R^{10})_k$-[C(=O)]$_l$—$R^{11}$, where
    each of j, k and l is independently 0 or 1;
    each $Z^1$ is independently selected from the group consisting of O, $NR^{12}$ and alkylene;
    each $R^{10}$ is independently selected from the group consisting of alkylene and cycloalkylene;
    each $R^{11}$ is independently selected from the group consisting of alkyl, alkoxy, aryloxy, —$NR^{13}R^{14}$, —$NR^{15}$—$NR^{16}R^{17}$, hydroxyalkyl and thioalkyl; and
    each of $R^{12}$, $R^{13}$, $R^{14}$, $R^{15}$, $R^{16}$, and $R^{17}$ is independently selected from the group consisting of hydrogen, alkyl, cylcoalkyl, and a nitrogen protecting group, and (f) -$L^xZ^x$, where $L^x$ is a linker comprising from 3 to 20 atoms selected from the group consisting of C, N, O, S, P and combinations thereof, and $Z^x$ is selected from the group consisting of hydrogen, a protecting group or a solid support;

each of $R^{31}$ and $R^{33}$ is independently selected from the group consisting of hydrogen, alkyl, a nitrogen protecting group and said acidic moiety optionally comprising an acidic moiety linker;

each of $R^{40}$, $R^{43}$ and $R^{44}$ is independently selected from the group consisting of hydrogen, alkyl, and a moiety of the formula: -$L^xZ^x$, -$(Z^1)_j$-C(=O)—$(R^{10})_k$—[C(=O)]$_l$—$R^{11}$, where $L^x$, $Z^x$, $Z^1$, j, $R^{10}$, k, l, and $R^{11}$ are those defined herein.

each of $R^{41}$ and $R^{42}$ is independently selected from the group consisting of hydrogen, alkyl, and said acidic moiety which optionally comprises said acidic moiety linker; and $R^{45}$ is selected from the group consisting of hydrogen, alkyl, alkoxy, cycloalkyl, halide, cyano, nitro, and a moiety of the formula: —[$X^4$]$_{m1}$—C(=O)—[O]$_{m2}$—$R^8$, where $X^4$, m1, m2, and $R^8$ are those defined herein.

In another embodiment, the negatively charged minor groove binding compound is covalently attached to a solid support, preferably through a solid support linker.

Another aspect of the present invention provides, a method for identifying a nucleic acid comprising:
(a) incubating a first oligonucleotide with an oligonucleotide probe; and
(b) identifying a hybridized nucleic acid;

wherein said oligonucleotide probe comprises:
a negatively charged minor groove binder moiety comprising:
    at least one aryl moiety, and
    at least one acidic moiety capable of ionizing under physiological conditions, wherein said acidic moiety is covalently attached to at least one of said aryl moiety, optionally through an acidic moiety linker; and
an oligonucleotide moiety which is covalently attached to said negatively charged minor groove binder moiety.

In one embodiment, the oligonucleotide probe is of the formula:

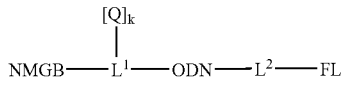

where NMGB, ODN, FL, Q, $L^1$, $L^2$ and k are those defined herein.

DEFINITIONS

Figure 1:
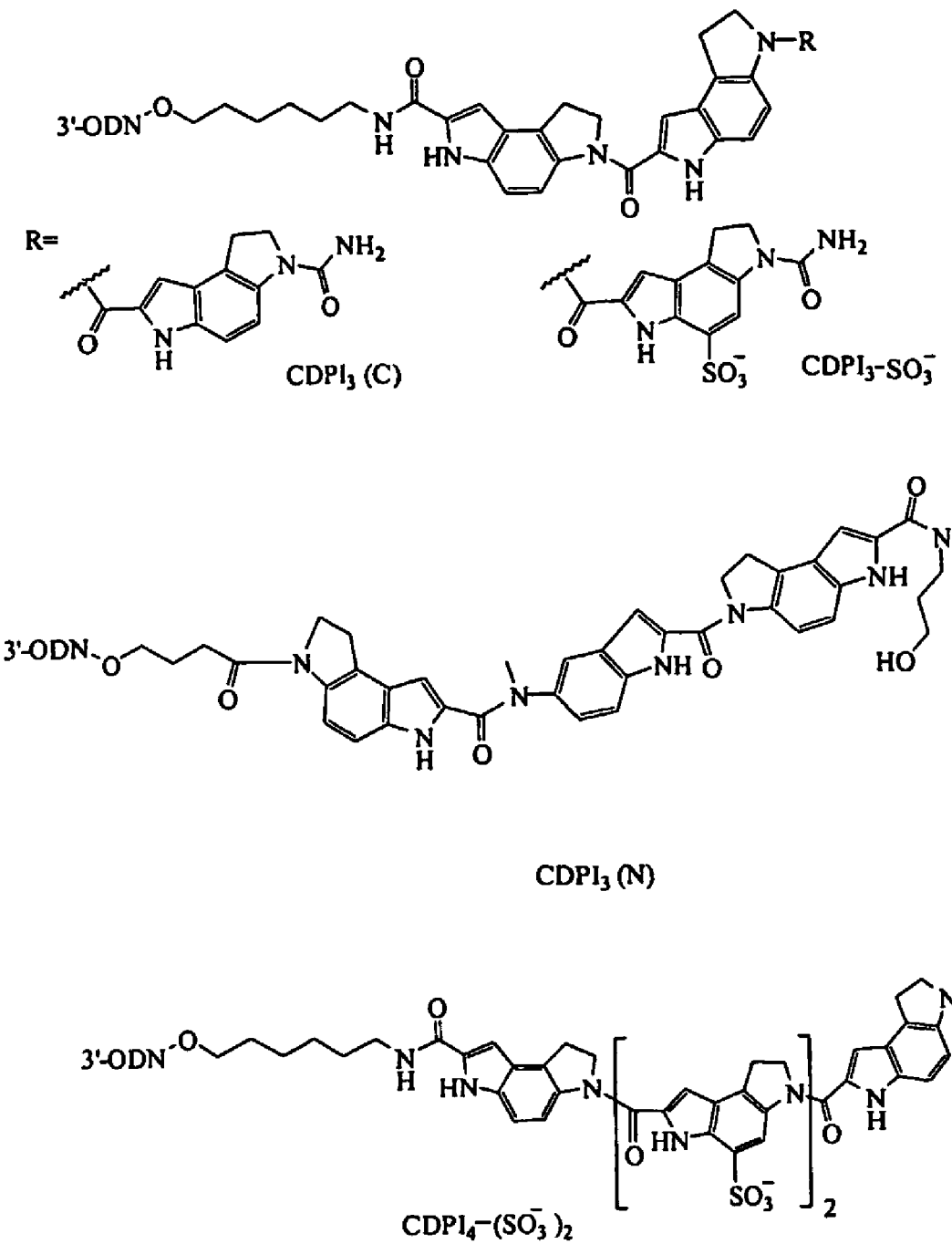
FIG. 1 shows structures of compounds that were used in a match and mismatch discrimination comparison test of Examples 4 and 5.

As used in this specification and the appended claims, the singular forms "a," "an" and "the" include plural references unless the content clearly dictates otherwise.

Throughout this disclosure, a squiggly line in a chemical structure indicates a point of attachment.

The terms "negatively charged minor groove binding compound", "negatively charged minor groove binder" and "negative minor groove binder" are used interchangeably herein and refer to a minor groove binding compound comprising an acidic moiety that is capable of being ionized under physiological conditions. Preferably, the acidic moiety has pKa of about 7 or less, more preferably pKa of about 6 or less, still more preferably pKa of about 5 or less, and most preferably pKa of about 4 or less.

The term "binds preferentially into a minor groove" means that the molecule binds within the double-stranded □-DNA minor groove in a high-affinity, preferably in a non-intercalative manner. Thus, a "minor groove binder" refers to a molecule that is capable of binding within the minor groove of double-stranded DNA, double-stranded RNA, DNA-RNA hybrids, DNA-PNA hybrids, hybrids in which one strand is a PNA/DNA chimera and/or polymers containing purine and/or pyrimidine bases and/or their analogues which are capable of base-pairing to form duplex, triplex or higher order structures comprising a minor groove.

The terms "quencher" refers to an acceptor moiety in fluorescence resonance energy transfer (FRET) detection method which is used in DNA or RNA probes.

The terms "fluorophore," "fluorescent label" and "reporter" are used interchangeably herein and refer to a reporter moiety in fluorescence resonance energy transfer (FRET) detection method which is used in DNA or RNA probes. Preferably, the fluorophore has a fluorescent emission maximum from about 400 to about 1000 nm, more preferably from about 400 to about 900 nm, and still more preferably from about 400 to about 800 nm. These compounds include, with their emission maxima in nm in brackets, CY2™ (506), YO PRO™-1 (509), YOYO™-1 (509), Calcein (517), FITC (518), FLUORX™ (519), ALEXA™ (520), Rhodamine 110 (520), 5-carboxyfluorescein (522), OREGON GREEN™ 500 (522), OREGON GREEN™ 488 (524), RIBOGREEN™ (525), RHODAMINE GREEN™ (527), Rhodamine 123 (529), MAGNESIUM GREEN™ (531), CALCIUM GREEN™ (533), TO PRO™-1 (533), TOTO@ -1 (533), JOE (548), BODIPY 530/550 (550), Dil (565), BODIPY® (568), BODIPY 558/568 (568), BODIPY 564/570 (570), CY3™ (570), ALEXA™ 546 (570), TRITC (572), MAGNESIUM ORANGE™ (575), Phycoerythrin R&B (575), Rhodamine Phalloidin (575), CALCIUM ORANGE™ (576), Pyronin Y (580), Rhodamine B (580), tetramethylrhodamine (582), Rhodamine RED™ (590), CY3.5™ (596), ROX (608), Calcium CRIMSON™ (615), ALEXA™ 594 (615), TEXAS RED (615), NILE RED (628), YO-3 (631), YOYO™-3 (631), R-phycocyanin (642), C-Phycocyanin (648), TO-PRO™-3 (660), TOTO (D-3 (660), DiD DilC(5) (665), CY5™ (670), Thiadicarbocyanine (671), Cy5.5 (694).

The terms "oligonucleotide," "nucleic acid" and "polynucleotide" are used interchangeable herein. These terms refer to a compound comprising nucleic acid, nucleotide, or its polymer in either single- or double-stranded form, e.g., DNA, RNA, analogs of natural nucleotides described below, and hybrids thereof. Unless otherwise limited, the terms encompass known analogs of natural nucleotides that hybridize to nucleic acids in a manner similar to naturally-occurring nucleotides. Examples of such analogs include. without limitation, phosphorothioates, phosphoramidates, methyl phosphonates, chiral-methyl phosphonates, 2-O-methyl ribonucleotides, and peptide-nucleic acids (PNAs). A "subsequence" or "segment" refers to a sequence of nucleotides that comprise a part of a longer sequence of nucleotides.

The terms "linker," "linking group" and "linking chain" are used interchangeably herein and refer to a chain of atoms that is used to assemble various portions of the molecule or to covalently attach the molecule (or portions thereof) to a solid support. Typically a linker has functional groups that are used to interact with and form covalent bonds with functional groups in the ligands or components (e.g., fluorophores, oligonucleotides, negatively charged minor groove binders, or quenchers) of the conjugates described and used herein. Examples of functional groups on the linking groups (prior to interaction with other components) include —NH2, —NHNH2, —ONH2, —NH—C=(O)—NHNH2, —OH, and —SH. A linker can include acyclic portions, cyclic portions, aromatic rings or combinations thereof. Preferably, the linker is cyclic, acyclic or a combination thereof. Typically, the linker (i.e., backbone) comprises a prescribed number of atoms selected from the group consisting of C, N, O, S, P and a combination thereof. Each of the atoms can be substituted with appropriate substituents known to one skilled in the art. For example, carbon atom can be substituted with a hydrogen, carbonyl oxygen, alkoxy, halide, amine, amide, cyano, hydroxyl. And sulfur and phosphorous atoms can be substituted with one or more oxygen atoms.

"Alkyl" means a linear or branched saturated monovalent hydrocarbon moiety which can be optionally substituted with one or more halides. Exemplary alkyl groups include, but are not limited to, methyl, trifluoromethyl, ethyl, n-propyl, 2-propyl, tert-butyl, pentyl, and the like.

"Alkylene" means a linear saturated divalent hydrocarbon moiety of one to ten, preferably one to six, carbon atoms or a branched saturated divalent hydrocarbon moiety of three to ten, preferably three to six, carbon atoms, e.g., methylene, ethylene, propylene, 2-methylpropylene, pentylene, and the like.

"Alkoxy" refers to a moiety of the formula —ORa2, where Ra2 is alkyl as defined herein.

"Aryl" means any monocyclic, bicyclic, tricyclic or tetracyclic ring moiety comprising a phenyl moiety and/or a heteroaryl moiety, which can optionally be fused to a heterocyclyl moiety. With the understanding that no two phenyl moieties are bonded together, i.e., no naphthyl moiety is present on the aryl group. With further understanding that the attachment of the aryl group is through a carbon or a heteroatom atom of a phenyl or a heteroaryl moiety. Moreover, the aryl group can be optionally substituted with one or more substituents selected from the group consisting of alkyl, heteroalkyl, heterocyclyl, halo, nitro, nitroso, cyano, carboxy and acyl. Exemplary aryl moieties include, but are not limited to, phenyl, fused phenyl-heteroaryl, and fused heteroaryl-phenyl-heterocyclyl as defined herein. Specific examples of aryl moieties include, but are not limited to, phenyl, indole, pyrroloindole, hydropyrroloindole, benzimidazole, imidazole, pyridine, 6-phenylimidazo[4,5-b]pyridine and furan.

"Aryloxy" refers to a moiety of the formula —ORa3, where Ra3 is an aryl moiety as defined herein.

"Cycloalkyl" refers to a saturated monovalent cyclic hydrocarbon moiety of three to seven ring carbons. The cycloalkyl can be optionally substituted independently with one or more substituents.

"Heteroaryl" means a monovalent monocyclic aromatic moiety of 5 to 12, preferably 5 or 6, ring atoms containing one, two, or three ring heteroatoms selected from the group consisting of N, O, or S, the remaining ring atoms being C. The heteroaryl ring can be optionally substituted independently with one or more substituents selected from the group consisting of alkyl, heteroalkyl, heterocyclyl, halo, nitro, nitroso, cyano, carboxy, acyl. More specifically the term heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl and the derivatives thereof.

"Fused phenyl-heteroaryl" means a bicyclic ring moiety comprising a phenyl moiety and a heteroaryl moiety as defined herein in which the phenyl moiety and the heteroaryl moiety share two or more, preferably two, common atoms. Such bicyclic ring moiety can be represented by a general formula:

where Het$^1$ is heteroaryl and Ph is phenyl.

"Fused heteroaryl-phenyl-heterocycloalkyl" means a tricyclic ring moiety comprising a phenyl moiety as the core which is covalently attached to both a heteroaryl moiety and a heterocyclyl moiety as defined herein in which the phenyl moiety independently shares at least two or more, preferably two, common atoms with the heteroaryl and the heterocyclyl moieties. Such tricyclic ring moiety can be represented by a general formula:

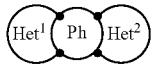

where Het$^1$ is heteroaryl, Ph is phenyl and Het$^2$ is heterocyclyl.

"Fused heteroaryl-heterocyclyl" refers to bycyclic, tricyclic or tetracyclic ring moiety comprising a heterocyclyl moiety and a heteroaryl moiety as defined herein in which the heterocyclyl moiety and the heteroaryl moiety share two or more, preferably two, common atoms with the understanding that the attachement is through the heteroatom of the heterocyclyl moiety. Such ring moiety can be represented by a general formula:

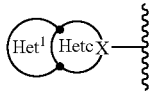

where Het$^1$ is heteroaryl and Hetc is heterocyclyl with X being a heteroatom of the heterocyclyl moiety.

"Fused aryl-heterocyclyl" means any bicyclic, tricyclic or tetracyclic ring moiety comprising a phenyl moiety and/or a heteroaryl moiety, which is fused to a heterocyclyl moiety. With the understanding that the attachment of the fused aryl-heterocyclyl group is through a heteroatom of a heterocyclyl moiety. Specific examples of fused aryl-heterocyclyl moieties include, but are not limited to, 1,2-dihydro-(3H)-pyrrolo[3,2-e]indole-7-carboxylate (i.e., CDPI), CPI, pyrroloindole and hydropyrroloindole.

"Heterocycloalkyl" refers to a saturated monocyclic or bicyclic moiety of 3 to 12, preferably 5 or 8, ring atoms in which one or two ring atoms are heteroatoms selected from N, O, or S(O)$_n$ (where n is an integer from 0 to 2), the remaining ring atoms being C, where one or two C atoms can optionally be replaced by a carbonyl group. The heterocyclyl ring can optionally be substituted with one or more substituents with the understanding that the heterocyclyl moiety is attached through a carbon atom of the heterocycloalkyl moiety.

"Heterocyclyl" refers to a non-aromatic monocyclic or bicyclic moiety of 3 to 12, preferably 5 or 8, ring atoms in which one or two ring atoms are heteroatoms selected from N, O, or S(O)$_n$ (where n is an integer from 0 to 2), the remaining ring atoms being C, where one or two C atoms can optionally be replaced by a carbonyl group. The heterocyclyl ring can optionally be substituted with one or more substituents with the understanding that the heterocyclyl moiety is attached through a heteroatom.

The terms "CDPI$_n$" and "DPI$_n$" are used interchangeably herein and refer to a moiety of the general formula:

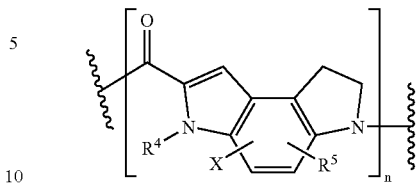

where X, R$^4$ and R$^5$ are those defined herein. Formula Z$^1$-CDPI$_n$-Z$^2$ means there are n-mer of CDPI (or DPI) with Z$^1$ being attached to the terminal carbonyl carbon and Z$^2$ being attached to the nitrogen atom of the pyrrole ring system. For example, a compound of the formula:

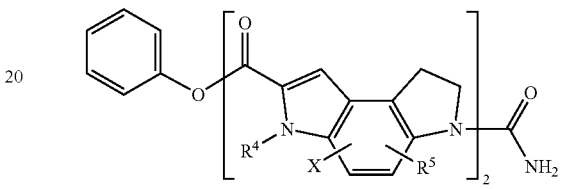

can be represented by a short hand notation PhO-CDPI$_2$—C(=O)—NH$_2$.

"Protecting group" refers to a moiety, except alkyl or cycloalkyl group, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, Harrison and Harrison et al., *Compendium of Synthetic Organic Methods*, Vols. 1-8 (John Wiley and Sons, 1971-1996), and "*Protection of Nucleosides for Oligonucleotide Synthesis*," Current Protocols in Nucleic Acid Chemistry, ed. by Boyle, A. L., John Wiley & Sons, Inc., 2000, New York, N.Y., all of which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom to which it is attached.

"Nitrogen protecting group" means an appropriate protecting group corresponding to the nitrogen atom to which the protecting group is attached. Such nitrogen atom can be in the form of an amine, an amide, a urea, an imine or other nitrogen functional group known to one skilled in the art. Suitable nitrogen protecting group for each nitrogen atom functional group are well known to one skilled in the art. See, for example, T. W. Greene and P. G. M. Wuts, *Protective Groups in Organic Synthesis*, 3$^{rd}$ edition, John Wiley & Sons, New York, 1999, Harrison and Harrison et al., *Compendium of Synthetic Organic Methods*, Vols. 1-8 (John Wiley and Sons, 1971-1996), and "*Protection of Nucleosides for Oligonucleotide Synthesis*," Current Protocols in Nucleic Acid Chemistry, ed. by Boyle, A. L., John Wiley & Sons, Inc., 2000, New York, N.Y., all of which were incorporated by reference above.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable excipient" means one or more excipients that are useful in preparing a pharmaceutical composition. Excipients are generally safe, non-toxic and neither biologically nor otherwise undesirable, and include excipients that are acceptable for veterinary use as well as human pharmaceutical use.

"Pharmaceutically acceptable salt" of a compound means a salt that is pharmaceutically acceptable and that possesses the desired pharmacological activity of the parent compound. Such salts include: salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.]

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, and the like.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"The term "treating", "contacting" or "reacting" when referring to a chemical reaction means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as preferred, more preferred and most preferred definitions, if any. Such variables refer to variables that are not part of a schematic illustrations.

DETAILED DESCRIPTION OF THE INVENTION

The presence of a plurality of aromatic rings in minor groove binders makes them prone to self-association due to the pi-interaction between the aromatic systems. One can reduce non-specific self-associations by introducing an electrostatic charge within the minor groove binders. However, because oligonucleotides are negatively charged, it is expected that introduction of one or more negative charges to a minor groove binder will result in electrostatic repulsion between the minor groove binder and DNA or RNA. This electrostatic repulsion, in turn, is expected to reduce the binding affinity of the minor groove binder to oligonucleotides. Thus, conventional electrostatic charged minor groove binding compounds contain a positive charge at the terminal position of the molecules. In addition to reducing aggregation, the positive charge also improves the affinity of the positively charged minor groove binders to negatively charged DNA duplexes. Unfortunately, the positive charge also increases non-specific binding.

I. Overview

The present invention is based on a surprising and unexpected discovery by the present inventors that negatively charged minor groove binders retained good oligonucleotide binding affinities while significantly reducing or eliminating the aggregation problems associated with neutral minor groove binders.

The negative minor groove binders of the present invention are useful in a variety of application including hybridization assays. While the negative minor groove binder can be used alone, it is particularly useful when covalently bound to an oligonucleotide, a quencher, a fluorophore, or a combination thereof.

II. Negatively Charged Minor Groove Binders

The negative minor groove binders of the present invention comprise at least one binding moiety, and at least one acidic moiety which is capable of ionizing under physiological conditions. As such, the acidic moiety has pKa of about 7 or less. Preferably pKa of about 6 or less, more preferably pKa of about 5 or less and still more preferably pKa of about 4 or less. Exemplary acidic moieties which are capable of ionizing under physiological conditions include moieties of the formula —$(O)_a S(O)_b OH$, wherein a is 0 or 1 and b is 1 or 2, —$(O)_c P(O)_d (OR^{a1})_e (OH)_f$, wherein each $R^{a1}$ is independently selected from the group consisting of alkyl, aralkyl and aryl; c is 0 or 1; each of d and e is independently 0, 1, or 2, and f is 1, 2 or 3, provided the sum of d+e+f is 2 or 3; —$CO_2H$; and salts thereof. Preferably, each of the acidic moiety in negative minor groove binder is independently selected from the group consisting of —$SO_2OH$, $OPO_2(OH)$, —$CO_2H$, and salts thereof. As used herein, the term "salts thereof" refers to alkaline metal salts, alkaline-earth metal salts, transition metal salts, ammonium salts, and alkyl substituted ammonium salts. Preferred salts include sodium, potassium, lithium, calcium, and magnesium.

The binding moiety comprises at least one aryl moiety. Preferably, the acidic moiety is covalently attached, optionally via an acidic moiety linker, to a phenyl portion or a heteroatom of a heteroaryl portion of the aryl moiety. In one embodiment, the binding moiety is selected from the group consisting of (a) a phenyl moiety;. (b) a heteroaryl moiety; (c) a fused phenyl-heteroaryl moiety; (d) a fused heteroaryl-phenyl-heterocyclyl moiety; or (e) a combination thereof. Each of which can optionally be substituted with one or more conventional substituents known to one skilled in the art. Preferably, the binding moiety is selected from the group consisting of (a) a heteroaryl moiety; (b) a fused aryl-heteroaryl moiety; (c) a fused heteroaryl-aryl-heterocyclyl moiety; and (d) a combination thereof.

In one embodiment, the binding moiety comprises a plurality of aryl moieties. Preferably at least three aryl moieties, and more preferably at least five aryl moieties. The aryl moieties can be linked directed to each other or can be linked through an aryl moiety linker comprising from 1 to about 10 atoms in the linking chain. In one preferred embodiment, the aryl moieties are covalently linked by an amide linkage (e.g., $Ar^x-R^{q1}-C(=O)-NR^{q2}-R^{q1}-Ar^y$), a urea linkage (e.g., $Ar^x-R^{q1}-NR^{q2}-C(=O)-NR^{q2}-R^{q1}-Ar^y$) or combinations thereof, where each of $Ar^x$ and $Ar^y$ is independently an aryl group, each of $R^{q1}$ is independently a bond or a linker comprising a chain of 1 to about 8 atoms, and each of $R^{q2}$ is independently hydrogen, alkyl, cycloalkyl or a nitrogen protecting group. Preferably, each of $R^{q1}$ is independently $C_1$-$C_8$ alkylene.

In one particular embodiment, each of the aryl moiety is independently selected from the group consisting of indole, benzofuran, pyrroloindole, hydropyrroloindole, phenyl, pyrrole, benzimidazole, imidazole, pyridine, 6-phenylimidazo[4,5-b]pyridine, furan, thioazole and oxazole.

The negative minor groove binders of the present invention comprise a sufficient amount of acidic moieties to provide a significant reduction in aggregation, and provides a sufficient binding affinity to oligonucleotides to be useful. In one particular embodiment, the negatively charged minor groove binder comprises a plurality of acidic moieties. The acidic moieties can be attached to the aryl groups in a variety of combinations. For example, each acidic moiety can be attached to a separate aryl group or some aryl groups can have one or more acidic groups and some aryl groups can have no acidic group attached. Still alternatively, all the acidic moieties can be attached to a single aryl moiety.

Preferably, the negatively charged minor groove binder comprises at least two acidic moieties, more preferably at least about 3 acidic moieties, and still more preferably at least about 5 acidic moieties. However, it should be appreciated that the actual number of acidic moieties are not limited to these specific quantities and examples given herein. The actual number of acidic moieties present in the negative minor groove binder is ultimately determined by the above described requirement, i.e., it should provide a significant reduction in aggregation while retaining a sufficient binding affinity to oligonucleotides. Thus, the number of acidic moieties in the negative minor groove binder can vary significantly depending on a variety of factors, including the overall structure of the negative minor groove binder, and the presence of other moieties, such as an oligonucleotide, a quencher and/or a fluorophore.

The acidic moiety is covalently attached to at least one of the aryl moiety. The acidic moiety can be directly linked to the aryl moiety or optionally via an acidic moiety linker. The acidic moiety linker comprises a chain of atoms arranged in a cyclic and/or acyclic manner. Typically, this linking chain comprises from 1 to about 30 atoms. In some embodiments, carbon atoms are substituted with hydrogen or carbonyl oxygen.

In one particular embodiment, the combination of acidic moiety and acidic moiety linker is of the formula:

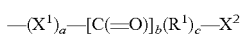

where $X^1$, $X^2$, a, b, c and $R^1$ are those defined herein. Preferably when $X^2$ is alkylene, it is $C_1$-$C_6$ alkylene.

One particularly useful negatively charged minor groove binding compound of the present invention is of the formula:

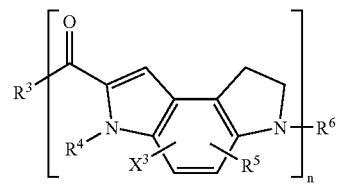

I where n, $R^3$, $R^4$, $R^5$, $R^6$ and $X^3$ are those defined herein, provided at least one of $X^3$, $R^{R4}$, $R^6$ and $R^7$ is an acidic moiety optionally comprising an acidic moiety linker. Preferably n is 2 to 8.

In another embodiment, the negatively charged minor groove binding compound of the present invention is of the formula:

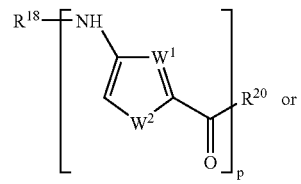

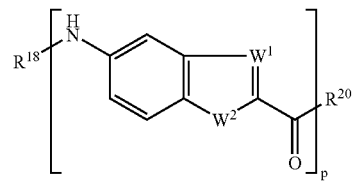

where p, $W^1$, $W^2$, $R^{18}$ and $R^{20}$ are those defined herein, provided at least one of $R^{18}$, $R^{19}$ (when $W^2$ is $NR^{19}$) and $R^{20}$ is an acidic moiety, optionally comprising an acidic moiety linker. In this embodiment, the negatively charged minor groove binding compound is preferably of the formula:

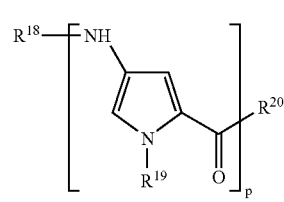

II where p, $R^{18}$, $R^{19}$ and $R^{20}$ are those defined herein.

In yet another embodiment of the present invention, the negatively charged minor groove binding compound is of the formula:

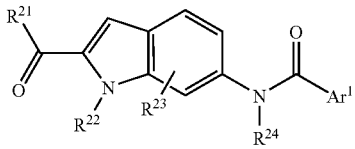

III where $Ar^1$, $R^{21}$, $R^{22}$, $R^{23}$ and $R^{24}$ are those defined herein.

Preferably, $R^{22}$ and $R^{24}$ of compound of Formula III are hydrogen.

Preferably, $R^{21}$ is a moiety of the formula:

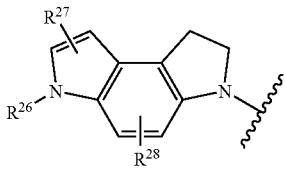

IV wherein $R^{26}$ is selected from the group consisting of hydrogen, alkyl, and a nitrogen protecting group;

$R^{27}$ is selected from the group consisting of:
(a) hydrogen,
(b) alkyl,
(c) cycloalkyl,
(d) said acidic moiety, optionally comprising said acidic moiety linker,
(e) -$(Z^1)_j$-C(=O)—$(R^{10})_k$—[C(=O)]$_l$—$R^{11}$,
where j, k, l, $Z^1$, $R^{10}$ and $R^{11}$ are those defined herein;
(f) -$L^xZ^x$, where $L^x$ and $Z^x$ are those defined herein; and $R^{28}$ is selected from the group consisting of hydrogen and said acidic moiety optionally comprising said acidic moiety linker.

Preferably, $Ar^1$ of compounds of Formula III is selected from the group consisting of:

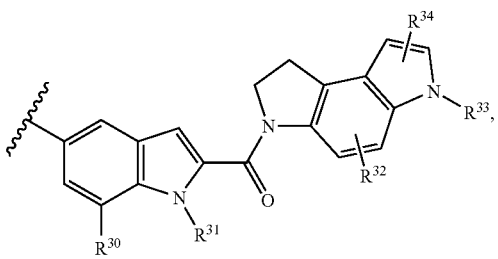

V

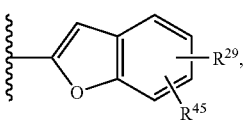

VI

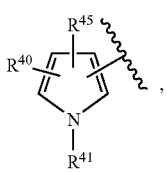

VII

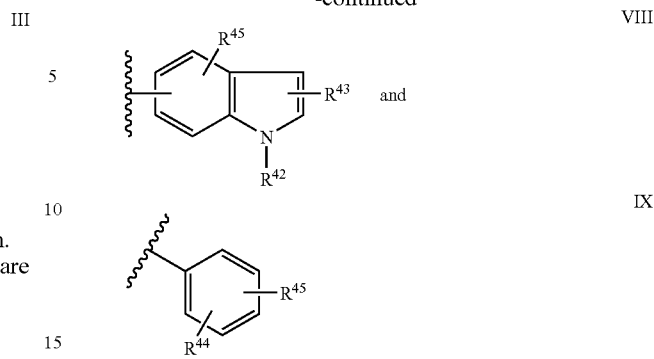

VIII

IX wherein each of $R^{29}$, $R^{30}$ and $R^{32}$ is independently selected from the group consisting of hydrogen and said acidic moiety, optionally comprising said acidic moiety linker;

$R^{34}$ is selected from the group consisting of:
(a) hydrogen,
(b) alkyl,
(c) cycloalkyl,
(d) said acidic moiety, optionally comprising said acidic moiety linker,
(e) -$(Z^1)_j$-C(=O)—$(R^{10})_k$—[C(=O)]$_l$$R^{11}$,
where j, k, l, Z1, $R^{10}$ and $R^{11}$ are those defined herein;
(f) -$L^xZ^x$, where $L^x$ and $Z^x$ are those defined herein;

each of $R^{31}$ and $R^{33}$ is independently selected from the group consisting of hydrogen, alkyl, a nitrogen protecting group and said acidic moiety optionally comprising an acidic moiety linker;

each of $R^{40}$, $R^{43}$ and $R^{44}$ is independently selected from the group consisting of hydrogen, alkyl, and a moiety of the formula: -$L^xZ^x$, -$(Z^1)_j$-C(=O)—$(R^{10})_k$—[C(=O)]$_l$—($R^{11}$, where $L^x$, $Z^x$, $Z^1$, j, $R^{10}$, k, l, and $R^{11}$ are those defined herein.

each of $R^{41}$ and $R^{42}$ is independently selected from the group consisting of hydrogen, alkyl, and said acidic moiety which optionally comprises said acidic moiety linker; and $R^{45}$ is selected from the group consisting of hydrogen, alkyl, alkoxy, cycloalkyl, halide, cyano, nitro, and a moiety of the formula: —$[X^4]_{m1}$—C(=O)—$[O]_{m2}$—$R^8$, where $X^4$, m1, m2, and $R^8$ are those defined herein.

A particularly useful negatively charged minor groove binding compounds of Formula III include those in which $R^{21}$ is a moiety of Formula IV and $Ar^1$ is a moiety of Formula V, VI, VII, VIII, or IX.

The negatively charged minor groove binding compounds of the present invention can also be covalently attached to a solid support. Such covalent attachment can be a direct linkage or, preferably through a solid support linker comprising 1 to about 30 atoms in the linking chain.

Synthesis of Negatively Charged Minor Groove Binders

Negatively charged minor groove binding compounds of the present invention can be synthesized using a variety of methods. One particular method for synthesizing compounds of Formula I comprising CDPI moiety is illustrated in Scheme I below.

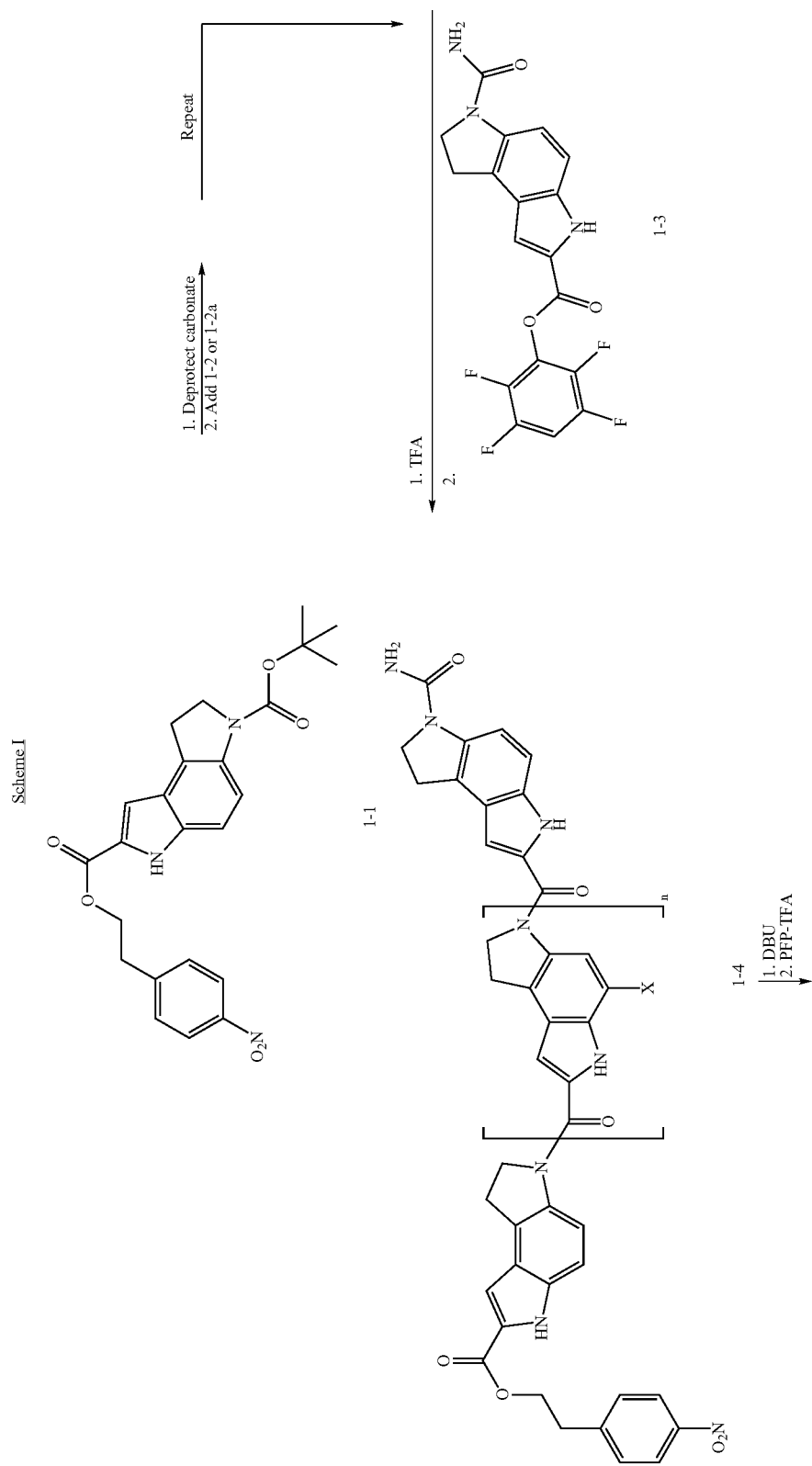

-continued
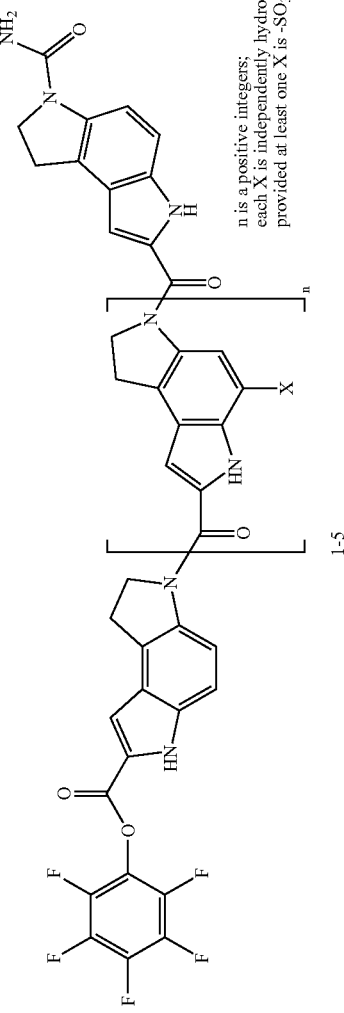
n is a positive integers;
each X is independently hydrogen or -SO₃H;
provided at least one X is -SO₃H
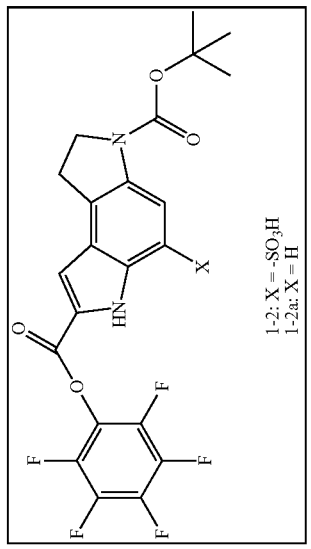
1-2: X = -SO₃H
1-2a: X = H As the above synthetic Scheme I shows, PFPO-CDPI$_m$—C(=O)—NH$_2$ (1-5) (where m=n+2 and PFPO is pentafluorophenoxide, i.e., pentafluorophenoxy, moiety), can be prepared by selective deprotection of tert-butyl carbamate and coupling the deprotected amine group with a suitably substituted pyrroloindoline 1-2 or 1-2a. Selective deprotection of tert-butyl carbamate group can be achieved by any of the conventional methods known to one skilled in the art including deprotecting reagents and conditions described in the above incorporated *Protective Groups in Organic Synthesis*, 3$^{rd}$ edition, and *Compendium of Synthetic Organic Methods*, Vols. 1-8.

Typically, the tert-butyl carbamate is selectively removed by reacting with an acid, such as trifluoroacetic acid (i.e., TFA). The deprotection can be carried out using TFA as both a solvent and a deprotecting reagent. In some cases, the deprotection is carreid out using a solution of TFA in an organic solvent, such as methylene chloride, chloroform and other inert organic solvent. The reaction temperature is typically room temperature. However, lower or higher reaction temperature can also be used depending on the nature of the starting material. For example, reaction temperature of about 0° C. provides slower reaction but higher selectivity, while reaction temperature at 30° C. or higher typically results in shorter reaction time but may yield slightly lower selectivity and/or product yield. The reaction time can range from few minutes to few hours depending on a variety of conditions such as the concentration of the starting material, reaction temperature and whether TFA is used as both a solvent and a deprotecting reagent or whether an inert organic solvent is used. Typically, the selective deprotection of the tert-butyl carbamate can be achieved within about 1 hr.

After the selective deprotection of the tert-butyl carbamate group, the resulting free amine is reacted with pyrroloindoline 1-2 or 1-2a to provide an oligomer of CDPI. The difference between pyrroloindolines 1-2 and 1-2a is the presence or the absence of the acidic moiety, respectively. Therefore, covalent attachment of pyrroloindoline 1-2 or 1-2a depends on whether an acidic group on the phenyl portion of the pyrroloindoline is desired or not. The coupling reaction results in covalent attachment of the free amine to the ester carbonyl group selectively. A carbonyl carbon of an ester group is generally more reactive than a carbonyl carbon of a carbamate group. This difference in the reactivity is increased even further by the presence of a pentafluorophenyl (i.e., PFP) group on the ester group. Thus, the coupling reaction of the present invention results in almost exclusive covalent attachment of the free amine to the ester carbonyl carbon atom. While pyrroloindolines 1-2 and 1-2a are depicted with PFP group, it is intended that such pyrroloindolines with other carbonyl activating group are also within the scope of the present invention. As used herein "carbonyl activating group" refers to a moiety which increases the reactivity of the carbonyl carbon of an ester relative to a similar alkyl ester group (e.g., ethyl).

Suitable coupling reaction conditions between an ester group and an amine group are well known to one skilled in the art. Typically, the coupling reaction involves suspending or, preferably dissolving, the free amine in an inert relatively polar organic solvent, such as DMF, DMSO, DME, and the like, and adding pyrroloindoline 1-2 or 1-2a in the presence of a non-nucleophilic base, such as tertiary amine compounds, bicarbonates and carbonates. The reaction is conveniently carried out at room temperature and is complete within few hours. Often the resulting coupled product precipitates out of the reaction mixture making the product recovery convenient. Typically, the product is simply filtered, washed and dried under vacuum.

As can be seen in Scheme I, the pyrroloindoline 1-2 and 1-2a contain a tert-butyl carbamate group. Therefore, the resulting coupled product can be subjected to selective deprotection and covalent attachment with another pyrroloindolines 1-2 and 1-2a. This process of selective deprotection and coupling is repeated until n number of pyrroloindoline moieties are coupled to the starting material. At least one of the coupling of a selectively deprotected tert-buty carbamate involves pyrroloindoline 1-2, such that the resulting CDPI$_m$ derivative 1-5 comprises an acidic moiety of the present invention. After the final tert-butyl carbamate group is deprotected, the resulting free amine is coupled with (i.e., covalently attached to) an urea derivative of pyrroloindoline 1-3. Pyrroloindoline 1-3 comprises tetrafluorophenyl ester moiety as a carbonyl activating group. However, similar to pyrroloindolines 1-2 and 1-2a discussed above, the ester moiety of pyrroloindoline 1-3 can also be activated with other conventional carbonyl activating group known to one skilled in the art.

The p-nitrophenylethyl ester moiety of Compound 1-4 is then selectively removed and trans-esterified with pentafluorophenyl-trifluoroacetate (i.e., PFP-TFA) to provide PFPO-CDPI$_m$—C(=O)NH$_2$ (1-5). Selective removal of the p-nitrophenylethyl ester moiety of Compound 1-4 can be achieved using a sterically hindered base such as DBU. Typically, a mixture of Compound 1-4 and DBU in an inert relatively polar organic solvent, such as DMF, DME and DMSO, is heated to about 50° C. for about 40 min. to provide a salt of the carboxylic acid. This salt is filtered, washed, dried and suspended in anhydrous organic solvent, e.g., DMF, in the presence of a non-nucleophilic base, such as tertiary amine. Addition of pentafluorophenyl trifluoroacetate then results in trans-esterification reaction to provide PFPO-CDPI$_m$—C(=O)—NH$_2$ (1-5). Compound 1-5 contains activated ester group, and therefore it can be covalently attached to a variety of compounds, including, oligonucleotides, such as DNA, RNA, PNA, hybrids thereof; fluorescent compounds; quencher compounds; and other suitable compounds.

Compound 1-2 can be produced by a variety of methods. In one particular embodiment, Compound 1-2 is synthesized from indoline sulfonic acid as shown in Scheme II below.

Scheme II

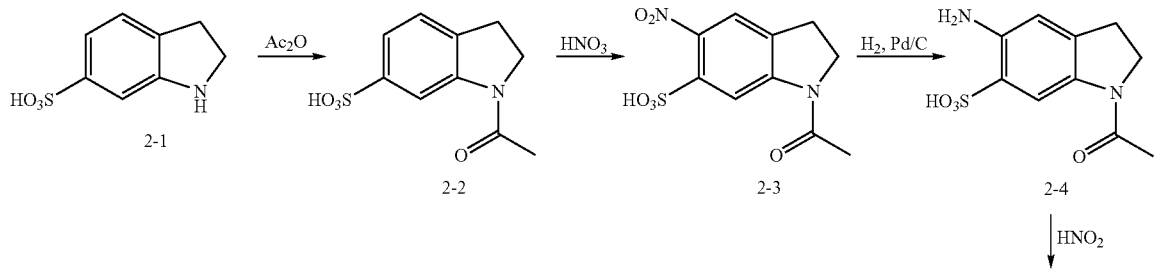

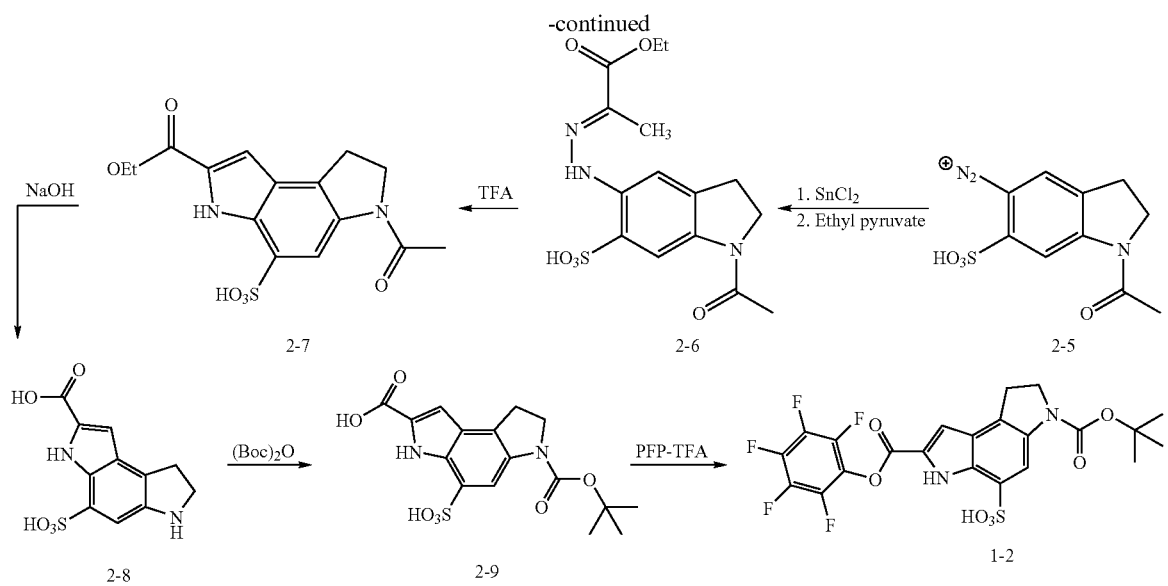

The starting material in Scheme II, indoline-6-sulfonic acid 2-1, can be prepared by a known procedure including the method disclosed in U.S. Pat. No. 4,405,788. Protection of the free amino group of indoline of indoline-6-sulfonic acid 2-1 followed by nitration of the phenyl ring provides a nitro indoline 2-3. While Scheme II illustrates the use of acetyl protecting group for the amino group, it should be appreciated that any conventional amino protecting group that is suitable (i.e., none interfering) for subsequent reaction conditions can be used. Nitration of the phenyl ring moiety of the indoline is well known in the art and can be conveniently achieved at 0° C. by using fuming nitric acid in sulfuric acid solution.

The nitro group is then reduced and converted to a diazonium salt 2-5. Treatment of the diazonium salt 2-5 with ethyl pyruvate in the presence of a Lewis acid affords aza compound 2-6, which is then cyclized to provide pyrroloindoline 2-7. The cyclization of the aza compound 2-6 is achieved using an acid catalyst. Typically refluxing conditions using trifluoroacetic acid is employed for cyclization reaction. To provide a dicarbonyl CDPI compound 1-2, the acetyl amino protecting group of pyrroloindoline 2-7 is then replaced with a Boc protecting group, and the free carboxylic acid is esterified as a pentafluorophenoxy ester. Compound 1-2 comprises two carbonyl groups each with different reactivity. This allows one to selectively attach other compounds on the nitrogen atom of the pyrrole ring moiety or the carbonyl carbon of the indoline ring moiety.

Other negatively charged minor groove binders can be readily prepared using the procedures disclosed herein. For example, as shown in Scheme III, starting with Compound 1 (or an appropriately protected Compound A or B), one can readily synthesize a wide variety of chimeric negatively charged minor groove binders.

Scheme III

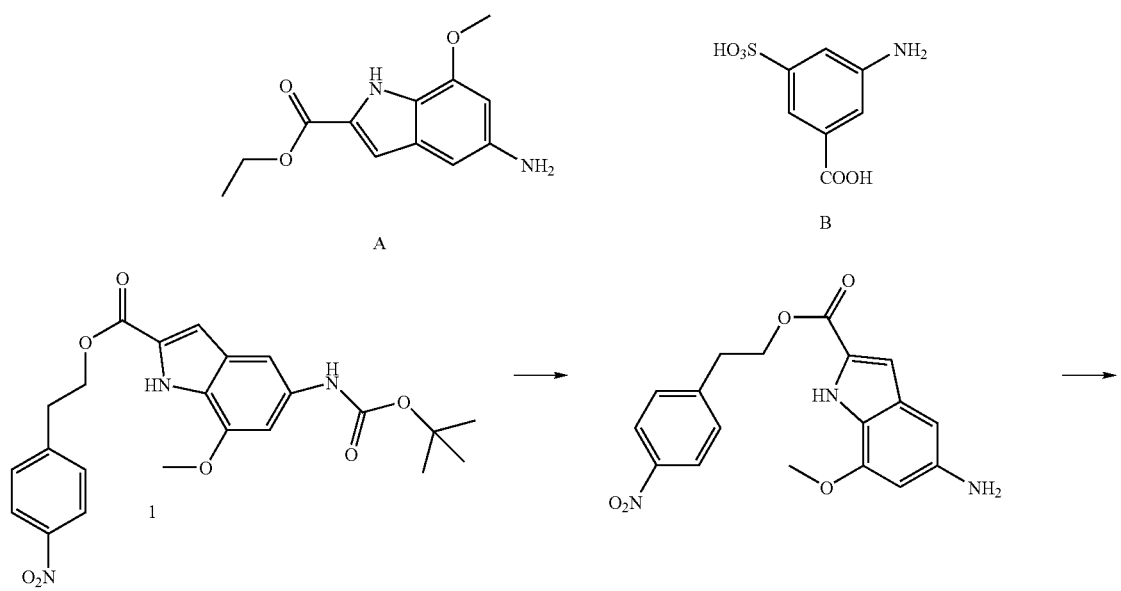

-continued

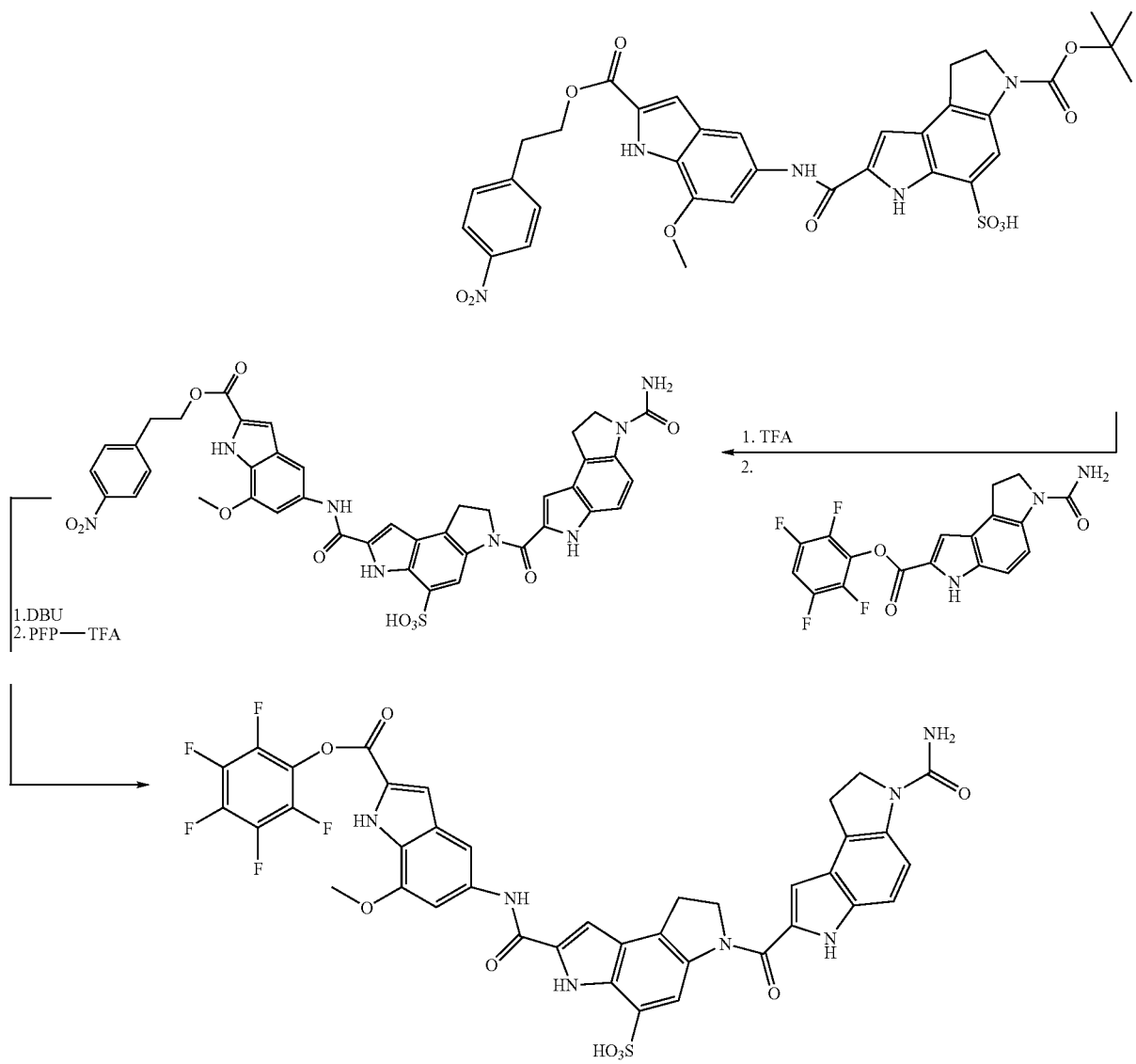

Since a wide variety of substituted indoles and other substituted aryl compounds are known, a number of negatively charged minor groove binders of the present invention can be readily prepared using the methods disclosed herein. For example, ethyl 5-amino-7-methoxyindole-2-carboxylic acid (Compound A) can be readily prepared by methods disclosed by Zhang et al. in *Synthesis,* 1996, 3, 377-382. In addition, 3-amino-5-sulfobenzoic acid (Compound B) can be synthesized from 3-nitro-5-sulfobenzoic acid using methods disclosed by Van Dorssen in *Recl. Trav. Chim. Pays. Bas.,* 1910, 29, 376.

In addition, methods for synthesizing neutral or basic compounds (e.g., Compound C) having structures similar to negatively charged minor groove binders of the present invention are known to one skilled in the art. See, for example, *J. Amer. Chem. Soc.,* 2000, 122, 6382-6394, which is incorporated by reference in its entirety. Such procedures can be used to prepare other negatively charged minor groove binders of the present invention.

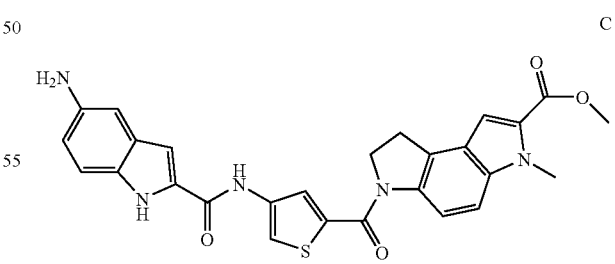

Thus, a wide variety of methods are available for synthesizing negatively charged minor groove binders of the present invention.

III. Oligonucleotide NMGB Conjugate

Another aspect of the present invention provides an oligonucleotide-negatively charged minor groove binder conjugate, or simply the "conjugate". The conjugates of the present invention comprise a negatively charged minor groove binder moiety and an oligonucleotide moiety which is covalently attached to the negatively charged minor groove binder moiety optionally through a linker.

Typically, the oligonucleotide moiety comprises from about 3 to about 100 nucleotide units. The oligonucleotide can be natural, such as DNA and RNA, unnatural, i.e., synthetic, such as PNA, locked nucleic acid, or a modified DNA and RNA containing modified nucleosides, or a combination thereof. Exemplary locked nucleic acids are disclosed in PCT Publication No. WO 01/56746, which is incorporated herein by reference in its entirety. Exemplary modified DNA and RNA containing modified nucleosides are disclosed in U.S. patent application Ser. No. 09/796,988, which is incorporated herein by reference in its entirety. Syntheses of PNA and PNA/DNA chimeras are known in the art and can be prepared from methods disclosed in, for example, Uhlmann et al., *Angew. Chem. Inter. Ed.,* 1998, 37, 2796-2823 and Mayfield et al., *Anal. Biochem.,* 1998, 401-404, which are incorporated herein by reference in their entirety.

In a preferred embodiment, the negatively charged minor groove binder moiety is covalently attached to either the 3'- or 5'-end of the oligonucleotide. Such attachment can be through a terminal base, sugar or phosphate moiety, or through a tail moiety attached to one of these moieties. In additional embodiments, the negatively charged minor groove binder moiety is attached to a nucleotide in an internal position, e.g., to an internal sugar moiety, or preferably to a base portion of the nucleotide.

In addition, the oligonucleotide-negatively charged minor groove binder conjugates of the present invention can also include other useful moieties, such as a fluorophore and/or a quencher. Thus, in one particular embodiment of the present invention, the oligonucleotide-negatively charged minor groove binder conjugate is of the formula:

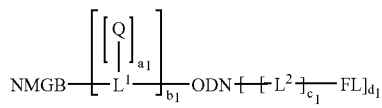

where NMGB, ODN, FL, Q, $L^1$, $L^2$, $a_1$, $b_1$, $c_1$ and $d_1$ are those defined herein.

In one embodiment of the present invention, the NMGB moiety is of the formula:

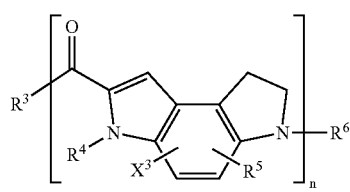

where n, $X^3$, $R^3$, $R^4$, $R^5$ and $R^6$ are those defined herein.

In another embodiment, the NMGB moiety is of the formula:

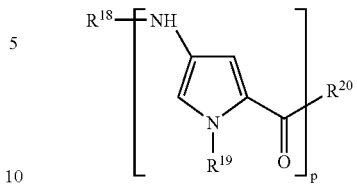

where p, $R^{18}$, $R^{19}$ and $R^{20}$ are those defined herein, provided at least one of $R^{18}$, $R^{19}$ or $R^{20}$ is the acidic moiety optionally comprising the acidic moiety linker, and one of $R^{18}$ and $R^{20}$ is a point of attachment to the first linker $L^1$ or to ODN depending on whether the first linker is present or absent, respectively.

In yet another embodiment, the NMGB moiety is of the formula:

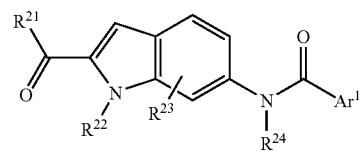

where $Ar^1$, $R^{21}$, $R^{22}$, $R^{23}$ and $R^{24}$ are those defined herein, provided when $R^{23}$ is hydrogen at least one of $Ar^1$ or $R^{21}$ is substituted with the acidic moiety optionally comprising the acidic moiety linker, and one of $R^{21}$, $R^{22}$, $R^{23}$ and $R^{24}$ is a point of attachment to the first linker $L^1$ or the oligonucleotide depending on the presence or absence of the first linker, respectively.

A. Fluorophores

The fluorophore moieties (FL) are well known to one skilled in the art. See, for example, U.S. Pat. No. 6,114,518, U.S. patent application Ser. No. 09/457,616, and Haugland, et al., HANDBOOK OF FLUORESCENT PROBES AND RESEARCH CHEMICALS, SIXTH ED., Molecular Probes, Eugene, Oreg. 1996, all of which are incorporated herein by reference in their entirety. Generally, any conventional fluorophore moieties known to one skilled in the art can be used in the oligonucleotide-negatively charged minor groove binder conjugates of the present invention. Preferably, fluorophores of the present invention have emission wavelength from about 400 to about 1000 nm, more preferably from 400 to about 900 nm, and most preferably from 400 to about 800 nm.

In one particular embodiment, the fluorophore moiety is a latent fluorophore. Such latent fluorophores are used in detection of nucleic acids by hybridization-triggered fluorescence. A latent fluorophore is a molecule in which a physical property of the fluorophore is altered by its interaction with duplex or triplex nucleic acids, resulting in a change in the fluorescence spectrum and/or an increase in the fluorescence quantum yield at a particular wavelength, and/or a change in some other fluorescent property of the molecule. A change in fluorescence spectrum can include a change in the absorption spectrum and/or a change in the emission spectrum. Such fluorophores are disclosed in a commonly assigned U.S. patent application Ser. No. 09/428,236, filed on Oct. 26, 1999, and entitled "Hybridization-triggered fluorescent detection of nucleic acids," which is incorporated herein by reference in its entirety.

In general, the fluorophore moiety can be any polycyclic, preferably polyaryl, compound which has the emission wavelength described herein, for example, fluorescein, rhodamine, bodipy, cyanine, resorufin, coumarin and analogs or derivatives thereof. Specific exemplary fluorophores include analogs or derivatives of fluoresceine, such as carboxyfluorescein, tetrachlorofluorescein, JOE, HEX, VIC, NED, tetramethylrhodamine, and ROX; cyanine, such as Cy3 and Cy5; resorufin; and coumarin. A fluorophore moiety can be covalently attached to an oligonucleotide through any of a variety of methods known to one skilled in the art. For example, the fluorophore moiety can be converted to a fluorophore phosphoramidite reagent of a general formula:

$$FL-L^2-X^{10}$$

where FL and $L^2$ are the fluorophore moiety and the second linker as defined herein, respectively, and $X^{10}$ is a reactive group (e.g., pentafluorophenyl ester or a phosphoramidite). Typically, an activated fluorophore phosphoramidite reagent of the formula:

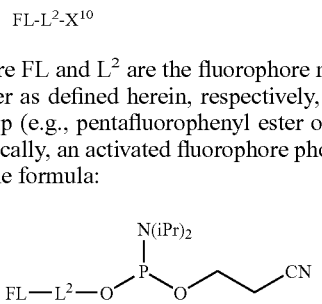

is often used to covalently link the fluorophore moiety to the 3'- or 5'-end of the oligonucleotide, or to an internal sugar moiety of the oligonucleotide using a conventional synthetic procedure known to one skilled in the art.

In one particular embodiment of the present invention, fluorophore moiety is a coumarin derivative selected from the group consisting of:

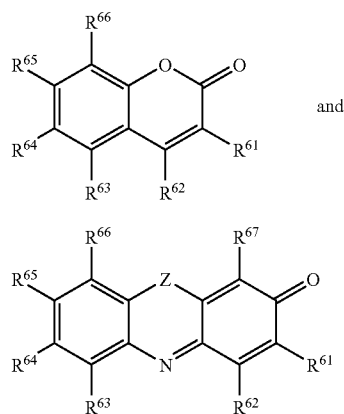

where $R^{61}$, $R^{62}$, $R^{63}$, $R^{64}$, $R^{65}$, $R^{66}$ and $R^{67}$ are those defined herein, provided that at least one of $R^{61}$, $R^{62}$, $R^{63}$, $R^{64}$, $R^{65}$, $R^{66}$ and $R^{67}$ is a bond that attaches the fluorophore to the second linker $L^2$ or to the oligonucleotide ODN depending on the presence or absence of the second linker, respectively.

Synthesis of Fluorophores

In one embodiment, the fluorophore moiety comprises a coumarin chromophore, e.g., moiety of Formula FL-1 above, which are well known to one skilled in the art. Such fluorophore can be covalently attached by using a corresponding phosphoramidite derivative. See, for example, PCT Publication No. WO 01/42505; *Bull. Chem. Soc. Japan.* 71(7):1719-1724 (1998); Kartha, et al., *Proc. Indian Acad. Sci. Sect. A,* 18:28 (1943); Atta, et al., *Phosphorus, Sulfur, Silicon Relat. Elem.* 80:109-116 (1993); U.S. Pat. No. 5,696,157; Nicolaides, et al., *J. Chem. Soc. Perkin Trans. I,* 2:283-290 (1992); and Saleh, et al., *Phosphorus, Sulfur, Silicon Relat. Elem.* 48:285-288 (1990). Other useful fluorophore moieties include 7-hydroxy-3H-phenoxazin-3-one chromophores, which are based on resorufin core structure that has emission wavelength of 595 nm. See, for example, PCT Publication No. WO 01/42505; Forchiassin et al., *J. Heterocyc. Chem.* 1983, 20, 493-494. Other useful fluorophores include phenoxazine and phenothiaxine derivatives, as well as those known to one skilled in the art.

Additional compounds suitable for elaboration into the present resorufin-type phosphoramidite reagents, which are suitable for incorporating into the oligonucleotide-negatively charged minor groove binder conjugates, are described in, for example, co-pending application Ser. No. 09/457,616; U.S. Pat. No. 4,954,630; Pashkevich, et al., *Chem. Heterocycl. Cmpd., Engl. Transl.* 11:308-312 (1975); Morrison, et al., *Photochem. Photobiol.,* 66:245-252 (1997); Afans'eva, et al., *Chem. Heterocycl. Cmpd., Engl. Transl.* 174-177 (1983); Chem. Abstracts 16329 (1955); Long, et al., *J. Heterocycl. Chem.* 36:895-900 (1999); and Musso, et al., *Chem. Ber.,* 96:1936-1944 (1963), all of which are incorporated by reference in their entireties.

A number of FL-1 and FL-2 fluorophores are available with an alkylcarboxyl group substituent which serves as a starting material for the synthesis of the corresponding phosphoramidite reagents. Alternatively, these compounds can be converted to reactive esters, e.g., pentafluorophenyl esters. The activated esters can be used to covalently attach these compounds to amine modified oligonucleotides.

Particular examples of coumarin based fluorophore phosphoramidites that are useful in conjugates of the present invention include, but are not limited to, those shown below.

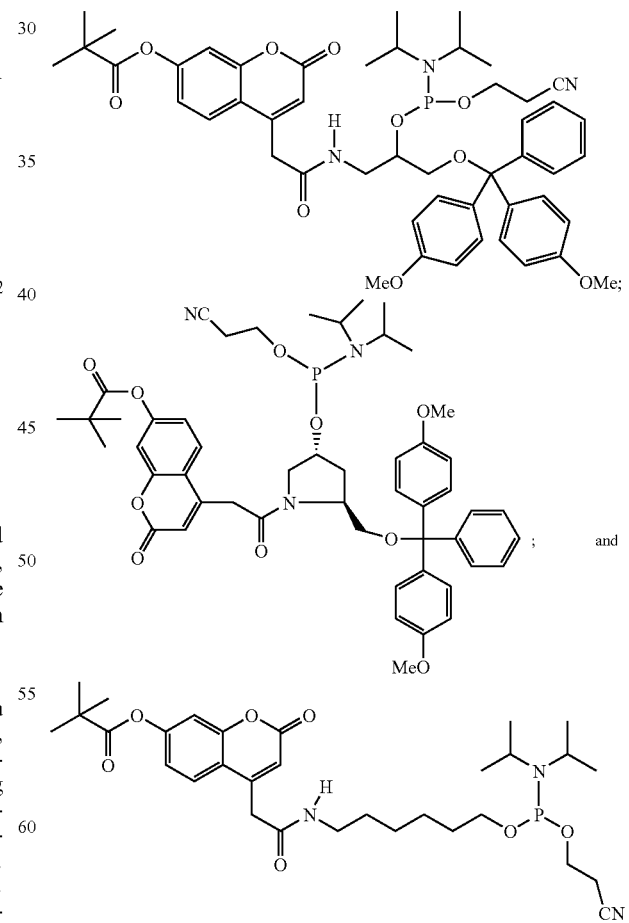

While the oligonucleotide-negatively charged minor groove binder conjugates of the present invention are illustrated in connection with the fluorophores and quenchers described herein, the present invention is not limited to these fluorphores and quenchers discussed herein. Any conventional fluorophores and quenchers known to one skilled in the art is within the scope of the present invention. For example, other suitable fluorophores and quenchers are disclosed in U.S. Pat. Nos. 5,328,824 and 5,824,796, which are incorporated herein by reference in their entireties.

B. Quenchers

The quencher moieties (Q) are also well known to one skilled in the art and are disclosed, for example, in the above incorporated U.S. Pat. No. 6,114,518, U.S. patent application Ser. No. 09/457,616, and Haugland, et al., HANDBOOK OF FLUORESCENT PROBES AND RESEARCH CHEMICALS, SIXTH ED., Molecular Probes, Eugene, Ore. 1996. Generally, any conventional quencher moieties known to one skilled in the art can be used in the oligonucleotide-negatively charged minor groove binder conjugates of the present invention. Preferably, quencher moieties of the present invention have absorbance maximum of from about 400 to about 1000 nm, more preferably from 400 to about 900 nm, and most preferably from 400 to about 800 nm. Exemplary quencher moieties include TAMARA, dabcyl and dabsyl having an absorption maximum in the wavelength region of about 400 to 800 nm; substituted diphenyldiazenes, such as those disclosed in PCT Publication No. WO 01/42505 and U.S. patent application Ser. No. 09/876,830; and substituted phenyl[4-(phenyldiazenyl)-phenyl]diazenes, such as those disclosed in PCT Publication No. WO 01/86001.

In one embodiment, the quencher moiety is a diazo compound of the formula:

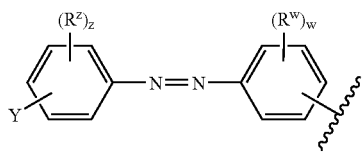

where Y, $R^z$, $R^w$, z and w are those defined herein. When Y is substituted phenyldiazenyl, the diazo quencher moiety comprises a plurality of diazo groups. For example, one particular diazo quencher moiety where Y is substituted phenyldiazenyl is of the formula:

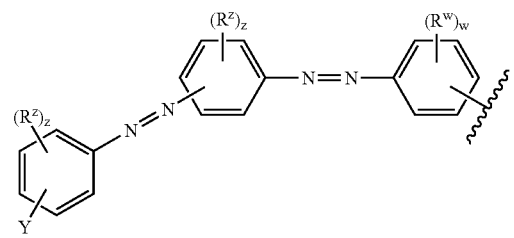

wherein Y, z, w, $R^w$ and $R^z$ are those defined herein;.

Substituted diazenyl can be synthesized using methods known to one skilled in the art. See, for example, PCT Publication No. WO 01/42505 and U.S. patent application Ser. No. 09/876,830. Substituted phenyl diazenyl can also be synthesized using methods known to one skilled in the art. See, for example, PCT Publication No. WO 01/86001. Additional substituted structures with different combinations of substituents at various positions can also be prepared, for example, by using compounds and methods known in the dye chemistry field. See, for example, the Color Index, Issue 3 on CD-ROM, pages 4009-4324; Society of Dyers and Colourists, Bradford, England; http://www.sdc.org.uk.

Particular examples of resorufin based quencher phosphoramidites that are useful in conjugates of the present invention include, but are not limited to, those shown below.

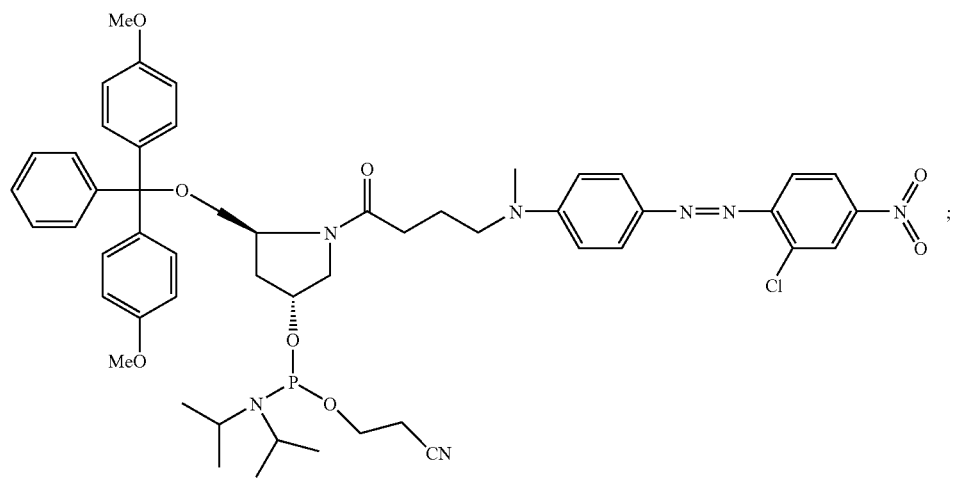

-continued

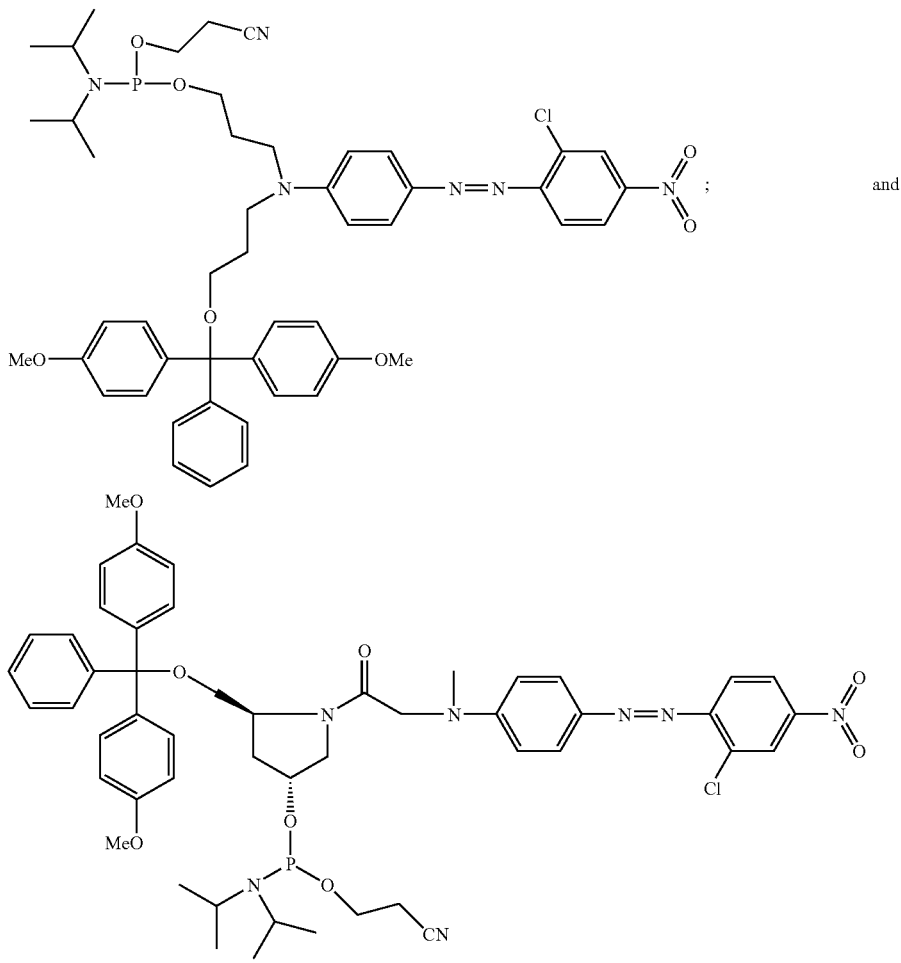

and

For those embodiments in which two adjacent $R^w$'s and carbon atoms to which they are attached form a fused ring system, the linking group $L^1$ of Formula X can be attached to either the phenyl ring (as indicated above) or to the ring formed by two adjacent $R^w$'s. Additionally, for those embodiments herein, where two alkyl groups are attached to a nitrogen atom, forming a dialkylamino substituent, the alkyl groups can be the same or different.

Preferably, the quencher moiety is of the formula:

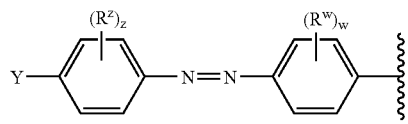

where w, z, $R^w$ and $R^z$ are those defined herein; and Y is selected from the group consisting of nitro and —N(CH$_3$)$_2$.

Synthesis of Quenchers Comprising $L^1$ Linker

Typically, quenchers of the present invention comprise the linker $L^1$, infra. In some instances, the linker comprises a phosphoramidite group and a protected alcohol group which serve as attachment points to a negatively charged minor groove binder and/or an oligonucleotide. Syntheses of these quenchers comprising a linker are illustrated in Schemes IV and V.

As shown in Scheme IV, a substituted 4-(phenyldiazenyl) phenylamine 1, where q is 1 to 20, is reacted with p-nitrophenylchloroformate to yield Compound 2. Compound 1 in Scheme IV is commercially available or can be produced using any of the conventional methods known to one skilled in the art. See, for example, U.S. Pat. No. 2,264,303, which is incorporated herein by reference in its entirety. In Scheme IV, the quencher is shown with linker $L^1$. In particular, the linker comprises a trifunctional pyrrolidinediol. Example of other $L^1$ linkers are discussed in detail below and are disclosed in U.S. Pat. No. 5,512,667, which is incorporated herein by reference in its entirety.

Reaction of Compound 2 with a substituted pyrrolidinediol yields a diol 3, where $R^x$ is a linker having from 1 to 15 chain atoms. The primary hydroxyl group of diol 3 is protected by reacting with dimethoxytrityl chloride (DMTrCl) to yield Compound 4. The secondary hydroxyl group of Compound 4 is reacted with 2-cyanoethyl diisopropylchloro-phosphoramidite to give the dimethoxytrityl protected phosphoramidite reagent 5. The dimethoxytrityl protected phosphoramidite reagent 5 can then be covalently linked to an oligonucleotide using methods conventionally known to one skilled in the art.

Scheme IV
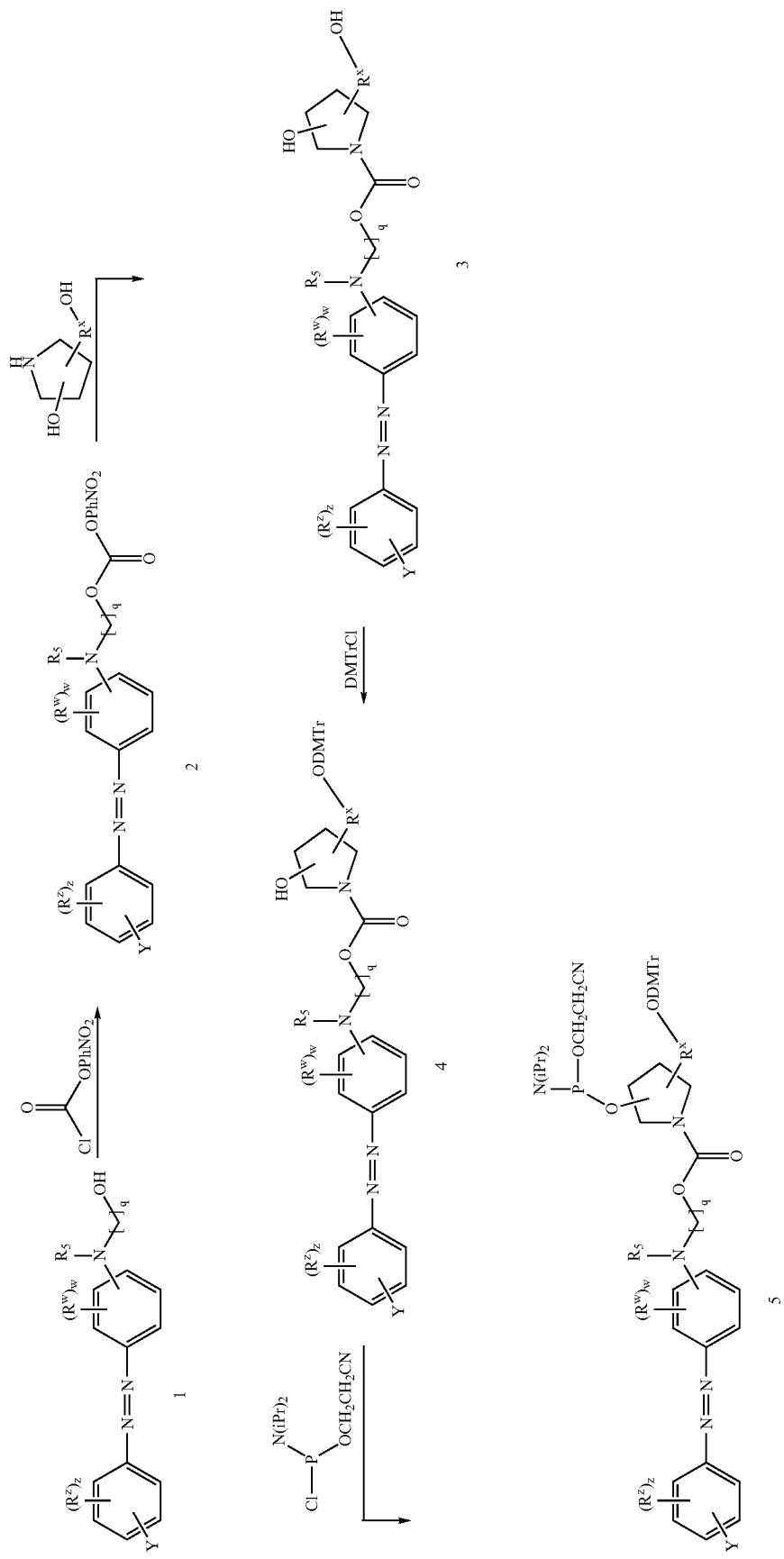

Procedure of Scheme IV is applicable for preparing quenchers with other $L^1$ linking groups. For example, by replacing the pyrrolidinediol with acyclic aminodiol compounds, phosphoramidites of Q-1 and Q-2 can be prepared, where r, s, t and v are each independently integers from 1 to 20; X is —O— or —CH$_2$—.

activated ester 7. The activated ester which is then reacted with a pyrrolidinediol compound having a free primary and a free secondary hydroxyl group to yield Compound 8. Treatment of Compound 8 with DMTrCl followed by reaction with 2-cyanoethyl diisopropylchlorophosphoramidite gives the dimethoxytrityl protected phosphoramidite reagent 10.

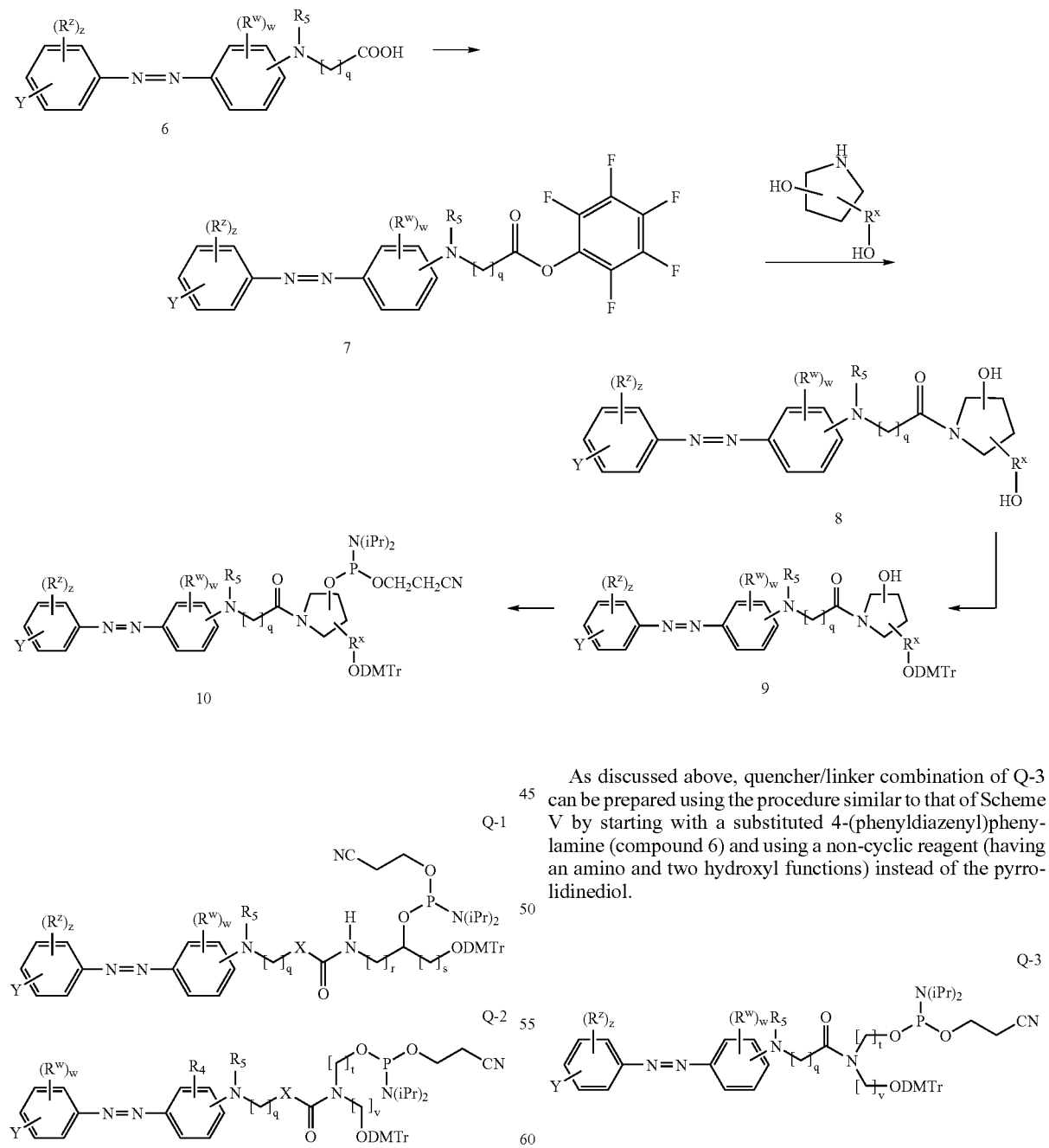

Scheme V illustrates synthesis of another exemplary phosphoramidite quencher 10. Compound 6 is commercially available or can be readily prepared according to procedures known to one skilled in the art. In Scheme V, Compound 6 is reacted with pentafluorophenyl trifluoroacetate to produce an As discussed above, quencher/linker combination of Q-3 can be prepared using the procedure similar to that of Scheme V by starting with a substituted 4-(phenyldiazenyl)phenylamine (compound 6) and using a non-cyclic reagent (having an amino and two hydroxyl functions) instead of the pyrrolidinediol.

Quenchers Attached to a Solid Support Through a Linker

In some aspects of the present invention, the quencher comprising $L^1$ linker is attached to a solid support, for example, controlled pore glass (CPG). This allows solid phase oligonucleotide synthesis. The linker has a hydroxyl function that is protected, usually by a dimethoxytrityl group which is removed during the synthesis when the first nucleotide is attached to the linker. Generally, the same quencher/linker intermediates described above in Schemes IV and V can also be used to prepare these reagents. One such method is illustrated in Scheme VI.

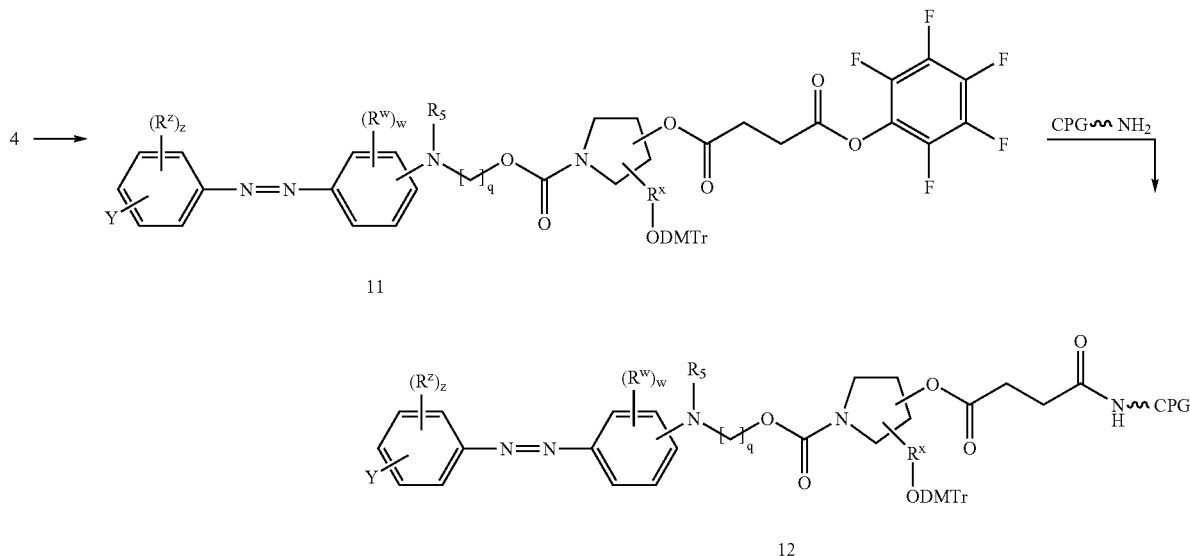

As shown in Scheme VI, the secondary hydroxyl group of Compound 4 in Scheme IV is reacted with succinic anhydride, and thereafter with pentafluorophenyl trifluoroacetate to provide an activated ester 11. The activated ester 11 is then reacted with the free amino group attached to the solid support (e.g., CPG bead) to provide the modified solid support 12. The exemplary modified solid support-bound quencher 12 includes a "linker" derived from pyrrolidine diol. However, it should be appreciated that other linkers and related structures, such as the linkers shown in Q-1, Q-2 and Q-3, can also be used in the procedure illustrated in Scheme VI to provide other solid support-bound quenchers, such as those shown in Q-5 and Q-6.

The solid support-bound quencher 12 in Scheme VI, Q-5 and Q-6 are useful for preparing 3'-quencher conjugates, which in turn allow the introduction of a fluorophore at the 5'-end with the appropriate phosphoramidite or with a fluorophore containing a reactive group. It should be appreciated that other solid supports (such as polystyrene) and other cleavable linker systems (in addition to the succinate linker shown) can also be prepared in accordance with these general teachings and are also within the scope of the invention.

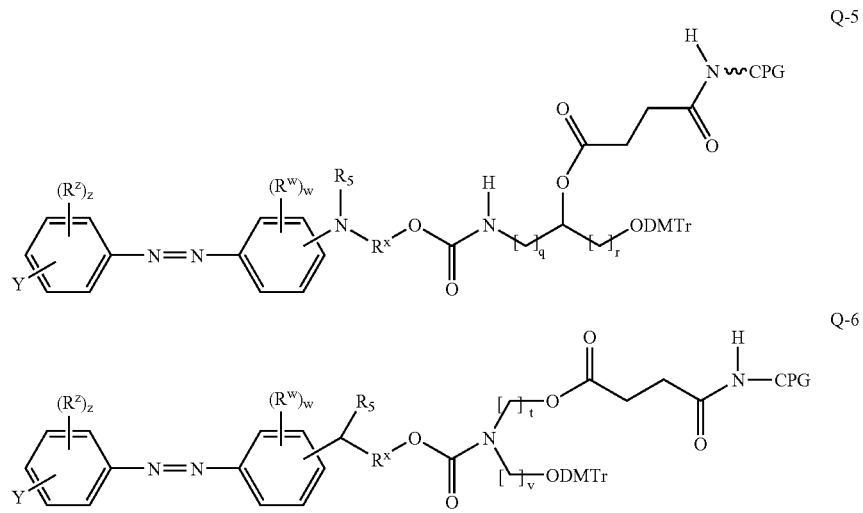

The reaction schemes provided above can be adapted by one of skill in the art to incorporate a variety of diazo quencher compounds and linkers. In addition, other structurally related compounds can be readily modified to produce a variety of quencher compounds using known chemical reactions. See, for example, Thiel, et al., *J. fur prakt. Chemie*, 328:497-514 (1986); U.S. Pat. Nos. 4,324,721 and 4,054,560; Timm, *Melliand Textilberichte*, 9:1090-1096 (1969); Hallas, J. S. D. C. 285-294 (1979); Beyer, et al., *J Prakt. Chem.*, 24:100-104 (1964); Hutchings, et al., *Chem. Europ. J.* 3:1719-1727 (1997) and Morley, et al., *J. Phys. Chem. A.*, 102:5802-5808 (1998); Haak, et al., *J. Chem. Res. Miniprint* 10:2701-2735 (1998) and Ruggli et al., *Helv. Chim. Acta*, 26:814-826 (1943), all of which are incorporated herein by reference in their entirety. Furthermore, structures with different combinations of substituents at various positions can also be prepared based on compounds and methods known in the dye chemistry field. See, for example, Color Index, Issue 3 on CDD-ROM, pages 4009-4324; Society of Dyers and Colourists, Bradford, England; http://www.sdc.org.uk, all of which are incorporated herein by reference in their entirety.

Some of the quencher which are readily available include dabcylnitrothiazole (e.g., Dabcyl®), QSY® (e.g., QSY-7, Molecular Probes, Eugene Oreg.), Rhodamine, Black Hole Quenchers (Biosearch Technologies, Novato, Calif.), tetramethylrhodamine, 6-(N-[7-nitrobenz-2-oxa-1,3-diazol-4-yl] amino) hexanoic acid, and 6-carboxy-X-rhodamine (Rox).

C. Linkers

Linkers are a chain of atoms that is used to assemble various portions of the molecule or to covalently attach the molecule (or portions thereof) to each other or to a solid support. Typically a linker has two or more, preferably two to four, and more preferably three or four, functional groups that are used to interact with and form covalent bonds with functional groups in the ligands or components, e.g., fluorophores, oligonucleotides, negatively charged minor groove binders, or quenchers. Linkers comprise a chain of atom(s) containing 1 to about 100 atoms, where each chain atom is independently selected from the group consisting of C, N, O, S, Si and P. In addition, each chain atom can be substituted with appropriate substituents known to one skilled in the art. For example, carbon atom can be substituted with a hydrogen, carbonyl oxygen, alkoxy, halide, amine, amide, cyano, hydroxyl. And sulfur and phosphorous atoms can be substituted with one or more oxygen atoms.

The linker can be acyclic, cyclic, or a combination thereof. Conventional di-, tri-, and tetra-functional linkers are well known to one skilled in the art. For example, exemplary 3'-alkylamine linkers are described in U.S. Pat. No. 5,419,966; exemplary prolinol linkers are described in U.S. Pat. No. 5,512,667; other exemplary tri- and tetrafunctional linkers are described in U.S. Pat. Nos. 5,451,463, 5,942,610 and 5,696,251. Some trifunctional linkers are commercially available, for example, from Glen Research (Sterling, Va.).

Typically, the linking groups are sufficiently robust so that they are stable to reaction conditions used in oligonucleotide synthesis, as well as the protection/deprotection chemistries used to prepare the conjugates described herein. Suitable linkers are well known to one skilled in the art. See, for example, U.S. Pat. No. 5,512,667, (prolinol based linkers), U.S. Pat. Nos. 5,451,463 and 5,141,813, (acyclic linkers), and U.S. Pat. Nos. 5,696,251, 5,585,422 and 6,031,091, (tetrafunctional linking groups), all of which are incorporated herein by reference in their entireties. Suitable functional groups on linkers for covalently attaching each component include, but are not limited to, primary and secondary nitrogen, —OH and —SH, and carbonyl derivatives (e.g., esters, anhydrides, amides, acids, carbamates, urea, carbonates, etc.).

Typically, the linker $L^2$ can be essentially any linking group that provides sufficient spacing for reaction of the phosphoramidite moiety to proceed when the composition is used to introduce FL into an oligonucleotide conjugate or composition. A variety of heterobifunctional linking groups are commercially available and can be used in the present invention.

It should be appreciated that each of the first linkers, $L^1$, described above represents a common core-structure. As such, the first linkers described above can further comprise additional linkers between the point of attachment, as indicated by a squiggly line, and a portion of the conjugate to which it is attached. Moreover, the functional groups which forms a link can be part of the portion of the conjugate to which the linker is attached. In some cases, $L^1$ is present on the quencher moiety during its preparation.

In one particular embodiment, the oligonucleotide-negatively charged minor groove binder conjugate is of the formula:

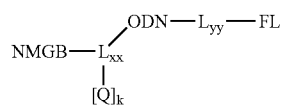

where

NMGB, ODN, FL, and Q are those defined herein;

each of $L_{xx}$ and $L_{yy}$ is independently a linker comprising a chain of 2 to 100 chain atoms, wherein each chain atom is independently selected from the group consisting of C, N, O, P, and S, provided that the total chain atoms of $L_{xx}$ and $L_{yy}$ is 100 or less; and k is 0 or 1.

In one particular embodiment, $L^1$ comprises a moiety selected from the group consisting of:

(a)

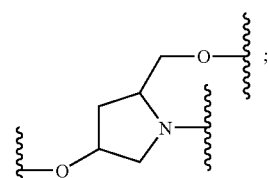

(L-1)

(b)

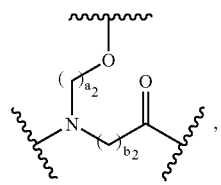

(L-2)

where $a_2$ and $b_2$ are those defined herein;

(c)

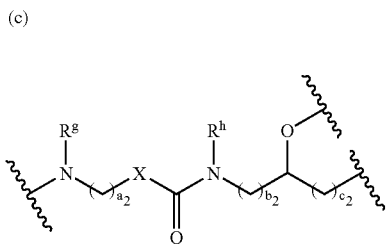
(L-3)

where $a_2, b_2, c_2, X, R^g$ and $R^h$ are those defined herein; and (d)

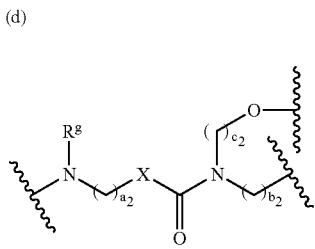
(L-4)

where $a_2, b_2, c_2, X,$ and $R^g$ are those defined herein.

Attachment of Q, ODN and NMGB can be any attachment point indicated by a squiggly line. Thus, each linkers above can have a wide variety of combinations of Q, ODN and NMGB attachments. In addition, the above described linker moieties can further comprise additional linkers covalently attached to the heteroatom attachment point. For example, one or more components, i.e, Q, ODN and/or NMGB, can be attached to the linkers shown above at the attachment point indicated, or they can be further tethered to another linking group.

In one particular embodiment, the first linker, $L^1$, is preferably a moiety of Formula L-1 or L-2.

In one embodiment, Formula L-1 is a particularly preferred linker when the quencher moiety is absent. In another embodiment, Formula L-2 is a particularly preferred linker when the quencher moiety is present.

In one particular embodiment of the present invention, the oligonucleotide-negatively charged minor groove binder conjugate is of the formula:

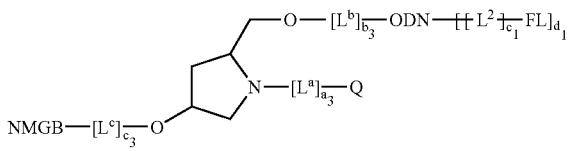

where
$c_1, d_1, L^2, Q, ODN, NMGB,$ and FL are those defined herein;

each of $a_3, b_3,$ and $c_3$ is independently 0 or 1; and each of $L^a, L^b$ and $L^c$ is independently a linker comprising an acyclic chain of from 1 to about 10 atoms, wherein each chain atom is independently selected from the group consisting of C, N, O, S and P.

In another embodiment of the present invention, the oligonucleotide-negatively charged minor groove binder conjugate is of the formula:

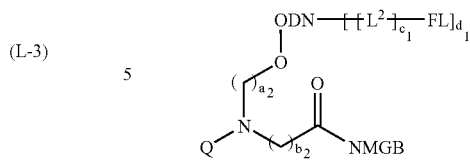

where $a_2, b_2, c_1, d_1, L^2,$ FL, Q, ODN and NMGB are those defined herein.

Still in another embodiment of the present invention, the oligonucleotide-negatively charged minor groove binder conjugate is of the formula:

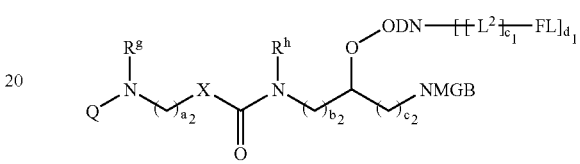

where $R^g, R^h, X, a_2, b_2, c_2, Q, ODN, NMGB, FL, L^2, c_1$ and $d_1$ are those defined herein.

Yet in another embodiment of the present invention, the oligonucleotide-negatively charged minor groove binder conjugate is of the formula:

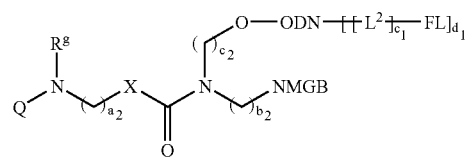

where $R^g, X, a_2, b_2, c_2, Q, ODN, NMGB, FL, L^2, c_1$ and $d_1$ are those defined herein.

D. Oligonucleotides

Preferably, an oligonucleotide comprises a plurality of nucleotide units, a 3'-end and a 5'-end. The oligonucleotide can contain one or more modified bases other than the normal purine and pyrimidine bases, as well as modified internucleotide linkages capable of specifically binding target polynucleotide through Watson-Crick base pairing, or the like. In addition, oligonucleotides can include peptide oligonucleotides (PNAs) or PNA/DNA chimeras, the synthesis of which is known. See, for example, Uhlmann et al., *Angew. Chem. Inter. Ed.*, 37:2796-2823 (1998); Mayfield et al., *Anal. Biochem.*, 401-404 (1998); and Kyaemo, et al., *J. Org. Chem.* 65:5167-5176 (2000), all of which are incorporated herein by reference in their entirety.

Preferably, the oligonucleotide has a sufficient number of phophodiester linkages adjacent to the 5' end to allow 5'-3' exonuclease activity to allow efficient cleavage between the quencher and fluorophore components in the conjugate. A suitable number of phosphodiester linkages in this regard is approximately between 1 and 100, but preferably between 3 and 40. In other embodiments, conjugates containing fluorophore and quencher pairs will provide adequate signal upon hybridization to the target nucleic acid, with cleavage of the probe. Amplified material can be detected with 5'-MGB-Q-ODN-FL conjugates in which the target is amplified via PCR and the detection is performed in real-time without cleavage of the conjugate. This method can also be used as an endpoint assay rather than a real-time procedure.

Similarly, modified sugars or sugar analogues can be present in one or more of the nucleotide subunits of an oligonucleotide conjugate. Sugar modifications include, but are not limited to, attachment of substituents to the 2', 3' and/or 4' position of the sugar, different epimeric forms of the sugar, differences in the α- or β-configuration of the glycosidic bond, and other anomeric changes. Sugar moieties include, but are not limited to, pentose, deoxypentose, hexose, deoxyhexose, ribose, deoxyribose, glucose, arabinose, pentofuranose, xylose, lyxose, cyclopentyl, and locked sugars (e.g., sugars containing other cyclic or bridged system resulting in a conformationally locked ring structure).

Oligonucleotide can also include modified bases, in addition to the naturally-occurring bases adenine, cytosine, guanine, thymine and uracil. Modified bases are considered to be those that differ from the naturally-occurring bases by addition or deletion of one or more functional groups, differences in the heterocyclic ring structure (i.e., substitution of carbon for a heteroatom, or vice versa), and/or attachment of one or more linker arm structures to the base. The modified nucleotides which may be included in the ODN conjugates of the invention include 7-deazapurines and their derivatives and pyrazolopyrimidines (described in PCT WO 90/14353); and in commonly assigned U.S. patent application Ser. No. 09/054,630.

Exemplary modified bases include the guanine analogues 6-amino-1H-pyrazolo[3,4-d]pyrimidin-4(5H)-one (ppG or PPG) and the adenine analogues 4-amino-1H-pyrazolo[3,4-d]pyrimidine (ppA or PPA). Also of use is the xanthine analogue 1H-pyrazolo[5,4-d]pyrimidin-4(5H)-6(7H)-dione (ppX). These base analogues, when present in an oligonucleotide, strengthen hybridization and improve mismatch discrimination. All tautomeric forms of naturally-occurring bases, modified bases and base analogues may be included in the oligonucleotide conjugates of the invention. In addition, modified internucleotide linkages capable of specifically binding target polynucleotide through Watson-Crick base pairing, or the like may also be included in the oligonucleotide conjugates of the present invention. Oligonucleotides can also include peptide oligonucleotides (PNAs) or PNA/DNA chimeras, the synthesis of which is known and can be performed for example in accordance with the publications Uhlmann et al., *Angew. Chem. Inter. Ed.*, 37:2796-2823 (1998) and Mayfield et al., *Anal. Biochem.*, 401-404 (1998).

As stated above, modified internucleotide linkages can also be present in oligonucleotide conjugates of the invention. Such modified linkages include, but are not limited to, peptide, phosphate, phosphodiester, phosphotriester, alkylphosphate, alkanephosphonate, thiophosphate, phosphorothioate, phosphorodithioate, methylphosphonate, phosphoramidate, substituted phosphoramidate and the like. Several further modifications of bases, sugars and/or internucleotide linkages, that are compatible with their use in oligonucleotides serving as probes and/or primers, will be apparent to those of skill in the art.

IV. Utility

Minor groove binders are useful in a variety of pharmaceutical applications. See, for example, Reddy et al., *Pharmacol. & Therap.*, 1999, 84, 1-111. Briefly, it is well known that certain bis-distamycins and related lexitropsins show activities against human immunodeficiency virus (HIV)-1 and HIV-2 at low nanomolar concentrations. It is also well recognized that some furan-containing analogues of berenil play an important role in their activities against *Pneumocystis carinii* and *Cryptosporidium parvuam* infections in vivo. Furthermore, Pt-pentamidine shows higher antiproliferative activity against small cell lung, non-small cell lung, and melanoma cancer cell lines compared with many other tumor cell lines. Moreover, trans-butenamidine shows good anti-*P. carinii* activity in rats. Pentamidine is used against *P. carinii* pneumonia in individuals infected with HIV who are at high risk from this infection. Neothramycin is used clinically for the treatment of superficial carcinoma of the bladder. Turner and Denny, *Current Drug Targets,* 2000, 1, 1-14 reported on the potential of sequence specific minor groove binders in the treatment of human disease. These compounds act in a variety of ways to inhibit gene expression, DNA replication and also alter nuclear architecture. Hybrid molecules containing pyrrolo[2,1-c]benzodiazepine and minor-groove-binding oligopyrrole carriers showed in vitro antiproliverative activity of K562 and Jurkat cell lines. See Baraldi et al., *J. Med. Chem.*, 1999, 42, 5131-5141. Positively charged netropsin derivatives has been described in WO 01/74898, these compounds have multiple applications, including use in human and animal medicine and in agriculture. Please note that charged minor groove binders show biological activity (Reddy et al)

The compositions (i.e., conjugates) of the present invention can be used with a variety of techniques, both currently in use and to be developed, in which hybridization of an oligonucleotide to another nucleic acid is involved. These include, but are not limited to, techniques in which hybridization of an oligonucleotide to a target nucleic acid is the endpoint; techniques in which hybridization of one or more oligonucleotides to a target nucleic acid precedes one or more polymerase-mediated elongation steps which use the oligonucleotide as a primer and the target nucleic acid as a template; techniques in which hybridization of an oligonucleotide to a target nucleic acid is used to block extension of another primer; techniques in which hybridization of an oligonucleotide to a target nucleic acid is followed by hydrolysis of the oligonucleotide to release an attached label; and techniques in which two or more oligonucleotides are hybridized to a target nucleic acid and interactions between the multiple oligonucleotides are measured. The conditions for hybridization of oligonucleotides, and the factors which influence the degree and specificity of hybridization, such as temperature, ionic strength and solvent composition, are well-known to those of skill in the art. See, for example, Sambrook et al., supra; Ausubel et al., supra; Innis et al. (eds.) PCR Protocols, Academic Press, San Diego, 1990; Hames et al. (eds.) NUCLEIC ACID HYBRIDISATION: A PRACTICAL APPROACH, IRL Press, Oxford, 1985; and van Ness et al. (1991) *Nucleic Acids Res.* 19:5143-5151.

Additionally, the compounds described herein can be used to detect polymeric targets such a nucleic acids using techniques utilized for, e.g., gene expression, SNP detection, sequencing methods, FRET detection (TaqMan assays, molecular beacons, linear beacons), array-based methods, primer extension, enzymatic methods, and the like.

In one embodiment, one or more FL-oligonucleotide conjugates are used as probe(s) to identify a target nucleic acid by assaying hybridization between the probe(s) and the target nucleic acid. A probe can be labeled with any detectable label of the present invention, or it can have the capacity to become labeled either before or after hybridization, such as by containing a reactive group capable of association with a label or by being capable of hybridizing to a secondary labeled probe, either before or after hybridization to the target. As a basis of this technique it is noted that conditions for hybridization of nucleic acid probes are well-known to those of skill in the art.

See, for example, Sambrook et al., MOLECULAR CLONING: A LABORATORY MANUAL, SECOND EDITION, Cold Spring Harbor Laboratory Press (1989); Ausubel et al., CURRENT PROTOCOLS IN MOLECULAR BIOLOGY, John Wiley & Sons (1987, 1988, 1989, 1990, 1991, 1992, 1993, 1994, 1995, 1996); Hames et al. (eds.) NUCLEIC ACID HYBRIDIZATION: A PRACTICAL APPROACH, IRL Press, Oxford, 1985; and van Ness et al. *Nucleic Acids Res.* 19:5143-5151(1991).

Hybridization can be assayed (i.e., hybridized nucleic acids can be identified) by distinguishing hybridized probe from free probe by one of several methods that are well-known to those of skill in the art. These include, but are not limited to, attachment of target nucleic acid to a solid support, either directly or indirectly (by hybridization to a second, support-bound probe or interaction between surface-bound and probe-conjugated ligands) followed by direct or indirect hybridization with probe, and washing to remove unhybridized probe; determination of nuclease resistance; buoyant density determination; affinity methods specific for nucleic acid duplexes (e.g., hydroxyapatite chromatography); interactions between multiple probes hybridized to the same target nucleic acid; and other known techniques. See, for example, Falkow et al., U.S. Pat. No. 4,358,535; Urdea et al., U.S. Pat. Nos. 4,868,105 and 5,124,246; Freifelder, PHYSICAL BIOCHEMISTRY, SECOND EDITION, Freeman & Co., San Francisco, 1982; Sambrook, et al., supra; Ausubel et al., supra; and Hames et al., supra.

Other applications for oligonucleotide-negatively charged minor groove binder conjugates comprising a fluorophore and quencher are found in assays in which a labeled probe is hybridized to a target and/or an extension product of a target, and a change in the physical state of the label is effected as a consequence of hybridization. A probe is a nucleic acid molecule that is capable of hybridizing to a target sequence in a second nucleic acid molecule. By way of example, one assay of this type, the hydrolyzable probe assay, takes advantage of the fact that many polymerizing enzymes, such as DNA polymerases, possess intrinsic 5'-3' exonucleolytic activities. Accordingly, if a probe is hybridized to a sequence that can serve as a template for polymerization (for instance, if a probe is hybridized to a region of DNA located between two amplification primers, during the course of an amplification reaction), a polymerizing enzyme that has initiated polymerization at an upstream amplification primer is capable of exonucleolytically digesting the probe. Any label attached to such a probe will be released, if the probe is hybridized to its target and if amplification is occurring across the region to which the probe is hybridized. Released label is separated from labeled probe and detected by methods well-known to those of skill in the art, depending on the nature of the label. For example, radioactively labeled fragments can be separated by thin-layer chromatography and detected by autoradiography; while fluorescently-labeled fragments can be detected by irradiation at the appropriate excitation wavelengths with observation at the appropriate emission wavelengths. This basic technique is described for example in U.S. Pat. No. 5,210,015.

A probe can contains both a fluorescent label and a quenching agent, which quenches the fluorescence emission of the fluorescent label. In this case, the fluorescent label is not detectable until its spatial relationship to the quenching agent has been altered, for example by exonucleolytic release of the fluorescent label from the probe. Thus, prior to hybridization to its target sequence, the dual fluorophore/quencher labeled probe does not emit fluorescence. Subsequent to hybridization of the fluorophore/quencher-labeled probe to its target, it becomes a substrate for the exonucleolytic activity of a polymerizing enzyme which has initiated polymerization at an upstream primer. Exonucleolytic degradation of the probe releases the fluorescent label from the probe, and hence from the vicinity of the quenching agent, allowing detection of a fluorescent signal upon irradiation at the appropriate excitation wavelengths. This method has the advantage that released label does not have to be separated from intact probe. Multiplex approaches utilize multiple probes, each of which is complementary to a different target sequence and carries a distinguishable label, allowing the assay of several target sequences simultaneously.

Another application embodiment uses a self-probing primer with an integral tail, where the quencher/fluorophore is present in the hairpin, that can probe the extension product of the primer and after amplification hybridizes to the amplicon in a form that fluoresces. The probing of a target sequence can thereby be converted into a unimolecular event (Whitcombe, et al., *Nat. Biotech.*, 17:804-807 (1999)).

Compositions of the invention can also be used in various techniques which involve multiple fluorescent-labeled probes. In some of these assays, changes in properties of a fluorescent label are used to monitor hybridization. For example, fluorescence resonance energy transfer (FRET) has been used as an indicator of oligonucleotide hybridization. In one embodiment of this technique, two probes are used, each containing a fluorescent label and a quencher molecule respectively. The fluorescent label is a donor, and the quencher is an acceptor, wherein the emission wavelengths of the donor overlap the absorption wavelengths of the acceptor. The sequences of the probes are selected so that they hybridize to adjacent regions of a target nucleic acid, thereby bringing the fluorescence donor and the acceptor into close proximity, if target is present. In the presence of target nucleic acid. irradiation at wavelengths corresponding to the absorption wavelengths of the fluorescence donor will result in emission from the fluorescence acceptor. These types of assays have the advantage that they are homogeneous assays, providing a positive signal without the necessity of removing unreacted probe. For further details and additional examples of the assays which are known in the art, see, for example, European Patent Publication 070685; Agrawal & Zamecnik, *Nucl. Acids Res.*, 18:5419-5423 (1990); and Cardullo et al. (1988) *Proc. Natl. Acad. Sci. USA* 85: 8790-8794. Additional applications of the novel compositions of the present invention are in those and related techniques in which interactions between two different oligonucleotides that are both hybridized to the same target nucleic acid are measured. The selection of appropriate fluorescence donor/fluorescence acceptor pairs will be apparent to one of skill in the art, based on the principle that, for a given pair, the emission wavelengths of the fluorescence donor will overlap the absorption wavelengths of the acceptor.

In another application of the novel compositions of the invention, the fluorescence of the conjugate is quenched in its native state. But, after hybridization with the intended target the spatial arrangement of the fluorophore and quencher moieties are changed such that fluorescence occurs. For this basic technique see, for example, Tyagi et al., *Nat. Biotech.*, 16:49-53 (1998); and U.S. Pat. No. 5,876,930.

It should be understood that in addition to the fluorophores which are found in accordance with the present invention especially useful to be used with the quenchers of the invention, and which fluorophores are incorporated into ODNs in accordance with the invention, a person of ordinary skill can choose additional fluorophores to be used in combination with the quenchers of the present invention, based on the optical properties described in the literature, such as the references: Haugland HANDBOOK OF FLUORESCENT PROBES AND RESEARCH CHEMICALS, Six Edition, Eugene, Oreg. pp. 235-236. 1996; Berlman, Handbook of Fluorescence Spectra of Aromatic Molecules, $2^{nd}$, Academic Press, New York, 1971; Du et al., PhotochemCAD. A Computer-Aided Design and Research Tool in Photochemistry, *Photochem. Photobiol.* 68:141-142 (1998).

In another application, the minor groove binder, dihydrocyclopyrroloindole tripeptide (i.e., $DPI_3$ or $CDPI_3$), is coupled to a quencher in a $FL-ODN-Q-CDPI_3$ conjugate to improve signal to noise ratios.

Yet another application of the conjugates of the present invention is to incorporate the pair into enzyme substrates, where fluorescence is quenched because of the proximity of the fluorophore and quencher. However, after an enzyme cleaves the substrate the fluorophore and quencher become separated and fluorescence is observed. It should be appreciated that conjugates containing both the quenchers and fluorophores can be constructed such that they are cleaved enzymatically.

Still in another application, the oligonucleotide conjugates of the present invention are utilized in procedures employing arrays of oligonucleotides or oligonucleotide conjugates. Techniques for sequencing by hybridization, single nucleotide polymorphism analysis (SNPs) and array-based analysis of gene expression (see, Hacia, et al., Nat. Genet. 22:119-120 (1999)) are well-known and can be readily adapted to utilize the conjugates of the present invention. For example, an ordered array of oligonucleotides of different known sequences (or their conjugates) is used as a platform for hybridization to one or more test polynucleotides, nucleic acids or nucleic acid populations. Determination of the oligonucleotides which are hybridized and alignment of their known sequences allows reconstruction of the sequence of the test polynucleotide. See, for example, U.S. Pat. Nos. 5,492,806; 5,525,464; 5,556,752; and PCT Publications WO 92/10588 and WO 96/17957. Materials for construction of arrays include, but are not limited to, nitrocellulose, glass, silicon wafers and optical fibers.

Additional objects, advantages, and novel features of this invention will become apparent to those skilled in the art upon examination of the following examples thereof, which are not intended to be limiting.

EXAMPLES

Example 1

This example illustrates a method for producing 3-[(tert-butyl)oxycarbonyl]-7-[(2,3,4,5,6-pentafluoropheny)oxycarbonyl]pyrrolo[3,2-e]indoline-5-sulfonic acid (Compound 1-2 in Scheme II)

Synthesis of 1-acetylindoline-6-sulfonic acid (Compound 2-2 in Scheme II)

Indoline-6-sulfonic acid (Compound 2-1 in Scheme II) (20 g), which was prepared according to the procedure described in U.S. Pat. No. 4,405,788, was dissolved in 200 mL of anhydrous DMF in the presence of 20 mL of triethylamine. Acetic anhydride (12 mL) was added, and the resulting solution was kept at room temperature for 8 h. DMF was evaporated and the residue was diluted with 100 mL of water. Concentrated sulfuric acid (20 mL) was added slowly with cooling. The product was allowed to crystallize overnight at 4° C. The crystals were collected by filtration and washed with small amount of cold water followed by acetone. Drying under vacuum over $P_2O_5$ afforded 18.6 g of the desired product as white crystals. $^1$H MNR (d6-DMSO) δ: 8.32 (s, 1H), 7.25 (dd, $J_1$=7.7 Hz, $J_2$=1.5 Hz, 1H) 7.14 (d, J=7.7 Hz), 6.70 ($OH+H_2O$), 4.07 (t, J=8.5 Hz, 2H), 3.09 (t, J=8.5Hz, 2H) and 2.14 (s, 3H).

Synthesis of 1-acetyl-5-nitroindoline-6-sulfonic acid (Compound 2-3 in Scheme II)

16.0 g (66 mmol) of 1-acetylindoline-6-sulfonic acid (Compound 2-2 in Scheme II) was dissolved in 160 mL of conc, sulfuric acid. The solution was cooled to 0° C. using ice/water bath. Nitric acid (90%, fuming) (3.0 mL, 1.1 eqv.) was added dropwise over 10 min. The resulting pale yellow solution was stirred at 0° C. for 2 h and then slowly poured onto 200 g of ice. The crystals formed were collected by filtration and washed successively with cold water acetone and ether. Drying under vacuum over $P_2O_5$ afforded 18.2 g of the title compound. $^1$H MNR (d6-DMSO) δ: 8.47 (s, 1H), 7.40 (s, 1H), 5.54 ($OH+H_2O$), 4.12 (t, J=8.5 Hz, 2H), 3.13 (t, J=8.5 HZ, 2H) and 2.17 (s, 3H). $^{13}$C NMR (d6-DMSO) δ: 169.19, 144.18, 143.17, 139.54, 133.54, 119.10, 115.23, 48,67, 26.75 and 24.01.

Synthesis of 1-acetyl-5-aminoindoline-6-sulfonic acid (Compound 2-4 in Scheme II)

A suspension of 1-acetyl-5-nitroindoline-6-sulfonic acid (Compound 2-3 in Scheme II) (9.0 g) in 250 mL of methanol was hydrogenated in the presence of 0.5 g of 10% Pd/C for 3 h. DMF (~250 mL) was added to dissolve the precipitated product. The catalyst was removed by filtration through Celite® and the filtrate was concentrated to give a solid. The solid was suspended in methanol (50 mL), filtered and washed with small amount of methanol and ether. Drying under vacuum afforded 6.4 g of the desired amine as an off-white solid.

5-{[(1E)-1-aza-2-(ethoxycaxbonyl)prop-1-enyl]amino}-1-acetylindoline-6-sulfonic acid (Compound 2-6 in Scheme II)

A suspension of 1-aceyl-5-aminoindoline-6-sulfonic acid (Compound 2-4 in Scheme II) (6.3 g, mmol) in a mixture of conc. HCl (40 mL) and water (35 mL) was cooled in ice/water bath. To the stirred mixture was slowly (~10 min) added a solution of $NaNO_2$ (2.0 g) in 10 mL of water. The resultant yellow suspension of the diazonium salt 5 was stirred at 0° C. for another 1 h and then used in the next reaction without workup.

To the above suspension of the diazonium salt (Compound 2-5 in Scheme II) was added a solution of $SnCl_2$ dihydrate (30.0 g) in 50 mL of water. The initially clear solution turned into a thick suspension in about 1 min. It was stirred for 30 min and treated with 4 mL of ethyl pyruvate to give a yellow suspension of the crude product (Compound 2-6 in Scheme II). After being stirred for another 30 min the solid was filtered off, washed with a mixture of 20 mL of conc. HCl and 80 mL of water followed by cold water. Drying under vacuum overnight afforded 8.7 g of the crude product (Compound 2-6 in Scheme II) which was contaminated with the tin salts. This product was 95% pure by HPLC analysis and was used in the next step without further purification.

Synthesis of 3-acetyl-7-(ethoxycarbonyl)[3,2-e]indoline-5-sulfonic acid (Compound 2-7 in Scheme II)

A solution of the crude 5-{[(1E)-1-aza-2-(ethoxycaxbonyl)prop-1-enyl]amino}-1-acetylindoline-6-sulfonic acid (Compound 2-6 in Scheme II) (8.5 g) in 220 mL of TFA was refluxed for 90 min. The reaction mixture was cooled and concentrated. The resulting black solid was chromatographed on silica eluting with an eluent comprising 5% triethylamine, 10% methanol and 85% dichloromethane. The product containing fractions were combined, concentrated, and the residue was triturated with cold methanol (30 mL). The precipitated off-white solid was collected by filtration, washed with ethyl acetate/hexane (1:1) and dried under vacuum. The yield of the pure product (triethylammonium salt) was 3.7 g. $^1$H MNR (d6-DMSO) δ: 10.09 (s, 1H), 8.85 (br s, 1H), 8.46 (s, 1H), 7.12 (d, J=2.2 Hz, 1H), 4.36 (q, J=7 Hz, 2H), 4.18 (t, J=8.7 Hz, 2H), 3.31 (t, J=8.6 Hz, 2H), 3.09 (m, 6H), 2.16 (s, 3H), 1.34 (t, J=7 Hz, 3H) and 1.16 (t, J=7.4 Hz).

Synthesis of 3-[(tert-butyl)oxycarbonyl]-5-sulfopyrrolo[3,2-e]indoline-7-carboxylic acid (Compound 2-9 in Scheme II)

To a solution of 3-acetyl-7-(ethoxycarbonyl)[3,2-e]indoline-5-sulfonic acid (Compound 2-7 in Scheme II) (3.6 g) in 37 mL of water was added 23 mL of 3 M KOH solution. The resultant suspension was stirred for 15 min to give a clear solution. The flask was placed into an oil bath and heated with stirring at 80° C. for 7 h. The resultant solution of the aminoacid (Compound 2-8 in Scheme II) was cooled to room temperature, and sodium bicarbonate (4.5 g) was added followed by a solution of Boc anhydride (2.0 g) in 20 mL of THF. The resulting emulsion was vigorously stirred for 5 h and then acidified with citric acid (~12 g) to pH of about 3. The mixture was concentrated to a semi-solid and triturated with methanol. The insoluble potassium citrate was filtered off, and the filtrate was concentrated. The solid was dissolved in DMF (100 mL). After stirring for 1 h, the solution was filtered to remove small amount of residual salts and concentrated. Drying under vacuum afforded 3.5 g of the desired product (Compound 2-9 in Scheme II) as a pale yellow, amorphous solid. The NMR analysis showed that the product was contaminated with potassium acetate and DMF. $^1$H MNR (d6-DMSO) δ: 9.98 (s, 1H), 8.05 (br s, 1H), 7.95 (s, 1H, DMF), 7.00 (d, J=2.2 Hz, 1H), 4.00 (m, 2H), 3.23 (t, J=8.7 Hz, 2H), 2,80 (d, DMF), 1.96 (s, CH$_3$COO$^-$ and 1.51 (s,911).

Synthesis of 3-[(tert-butyl)oxycarbonyl]-7-[(2,3,4,5,6-pentafluoropheny)oxycarbonyl]-pyrrolo[3,2-e]indoline-5-sulfonic acid (Compound 1-2 in Scheme II)

To a solution of the above compound (Compound 2-9 in Scheme II) (1.7 g) in DMF (10 mL) was added triethylamine (2.0 mL) followed by pentafluorophenyl trifluoroacetate (i.e., PFP-TFA) (2.0 mL). After stirring for 1 h, the solution was concentrated under vacuum to afford a dark oil. The mixture was chromatographed on silica eluting with a gradient of methanol (10-20%) in dichloromethane. The product fractions were combined and concentrated to give a tan, oily product. Trituration with 30% ethyl acetate/hexane produced a precipitate of the desired pentafluorophenyl (i.e., PFP) ester (1.22 g). $^1$H MNR (d6-DMSO) δ: 10.34 (s, 1H), 8.25 (br s, 1H), 8.46 (s, 1H), 7.56 (d, J=2.2 Hz, 1H), 4.04 (t J=8.7 Hz, 2H), 3.29 (t, J=8.6 Hz, 2H) and 1.53 (s, 911).

Example 2

This example illustrates a method for synthesizing CDPI-trimer (i.e., CDPI$_3$) derivative of the present invention.

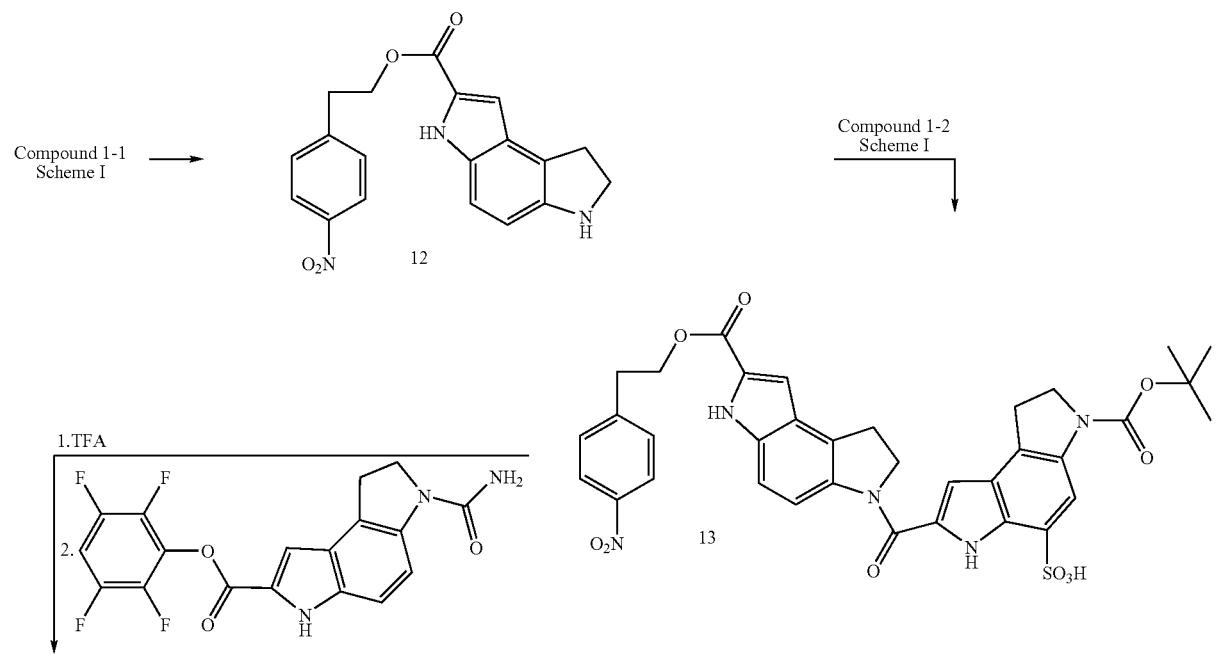

Compound 1-4 (n = 1, X = SO₃H) Scheme I →[1.DBU][2. PFP—TFA] Compound 1-5 (n = 1, X = SO₃H) Scheme I Synthesis of 3-[(tert-butyl)oxycarbonyl]-7-[(7-{[2-4-nitrophenyl)ethyl]oxycarbonyl}-pyrrolo[3,2-e]indolin-3-yl)carbonyl]pyrrolo[3,2-indoline-5-sulfonic acid, triethylammonium salt (13)

2-(4-Nitrophenyl)ethyl 3-[(tert-butyl)oxycarbonyl]pyrrolo[4,5-e]indoline-7-carboxylate (1.62 g) (Compound 1-1 of Scheme I) was selectively deprotected by treatment with 15 mL of trifluoroacetic acid (i.e., TFA) for 1 h. TFA was evaporated to afford a TFA salt of amine 12. Residual TFA was removed by co-evaporation with ether followed by drying under vacuum. The TEA salt was dissolved in 30 mL of anhydrous DMF in the presence of 0.9 mL of triethylamine. Compound 1-2 of Scheme II (see Example 1) (1.86 g) was added and the reaction was stirred at room temperature overnight. The solvent was evaporated under vacuum and the semi-solid residue was triturated with 10% MeOH/dichloromethane. The resulting yellow solid was collected by filtration and washed with the MeOH/dichloromethane mixture followed by ether. Drying under vacuum afforded 2.2 g of the dimer 13. The product contained about 1 equivalent of DMF according to the NMR analysis. ¹H MNR (d6-DMSO) δ: 11.96 (s, 1H, NH), 10.27 (s, 1H, NH), 8.84 (br s, 1H), 8.33 (d, J=8.8 Hz, 1H), 8.19 (d, J=8.8 Hz, 2:H), 8.12 (br s, 1H), 7.65 (d, J=8.8 Hz, 2H), 7.35 (d, J=8.8 Hz, 1H), 7.08 (s, 1H), 7.07 (s, 1H), 4.64 (t, J=8 Hz, 2H), 4.57 (t, J=6.4 Hz, 2H), 4.03 (t, J=8.5 Hz, 2H), 3.44 (t, J=8 Hz, 2H), 3.27 (t, J=8.5 Hz, 2H), 3.22 (t, J=6.6 Hz, 2H), 3.09 (m, 6H), 1.52 (s, 9H) and 1.16 (t, J=7.4 Hz, 9H).

Synthesis of 3-[(3-carbarmoylpyrrolo[4,5-e]indolin-7-yl)carbonyl]-7-[(7-{[2-(4-nitrophenyl)ethyl] oxycarbonyl}pyrrolo[3,2-e]indolin-3-yl)carbonyl] pyrrolo[3,2-e]indoline-5-sulfonic acid (Compound 1-4, n=1, X=SO₃H, of Scheme I)

Compound 13 (1.2 g) from above was deprotected by a treatment with 26 mL of 50% TFA/CH₂Cl₂ for 2 h. The reaction was concentrated and the resultant TFA salt was washed with ether and dried under vacuum. To a suspension of the TFA salt in anhydrous DMF (25 mL) was added triethylamine (0.9 mL) followed by 2,3,5,6-tetrafluorophenyl 3-carbamoylpyrrolo[4,5-e]indoline-7-carboxylate (0.8 g) (prepared from the procedure described by Lukhtanov et al. in *Bioconjugate Chem.*, 1995, 6, 418-426). The reaction mixture was stirred at room temperature for 24 h. DMF was evaporated and the residue was triturated with CH₃CN. The solid was stirred overnight and collected by filtration. Washing with ethyl acetate and drying under vacuum afforded 1.3 g of the trimer (Compound 1-4, n=1, X=SO₃H, of Scheme I) as an off-white solid.

Synthesis of 3-[(3-carbamoylpyrrolo[4,5-e]indolin-7-yl)carbonyl]-7-({7-[(2,3,4,5,6-pentafluorophenyl) oxycarbonyl]pyrrolo[3,2-e]indolin-3-yl}carbonyl) pyrrolo [(3,2-e]indoline-5-sulfonic acid (Compound 1-5, n=1, X=SO₃H, of Scheme I)

To a suspension of Compound 1-4 (n=1, X=SO₃H, of Scheme I) (1.3 g) in 75 mL of DMF was added 4.5 mL of DBU. After being stirred at 50° C. for 40 min the solution was concentrated and the residue was triturated with ether (150 mL). The solid was filtered off, washed with ether and dried. This procedure afforded 1.7 g of the free acid (DBU salt) as a pale yellow solid. This product was suspended in anhydrous DMF (35 mL) and treated with triethylamine (1.7 mL) followed by PEP-TFA (1.7 mL). After being stirred for 1 h the solution was concentrated, ether was added to the residue to precipitate the product. It was filtered off, washed with 50% MeOH/ether and ether. Drying under vacuum afforded 1.1 g of the title PFP ester as a dark yellow solid.

Example 3

This example illustrates a method for synthesizing CDPI-tetramer (i.e., DPI₄ or CDPI₄) derivative of the present invention.

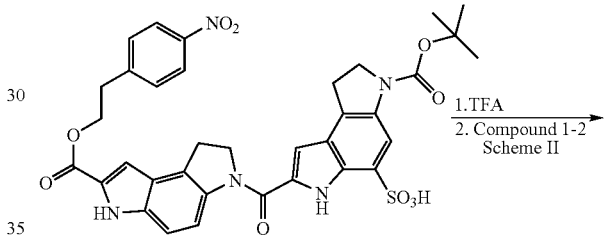

13

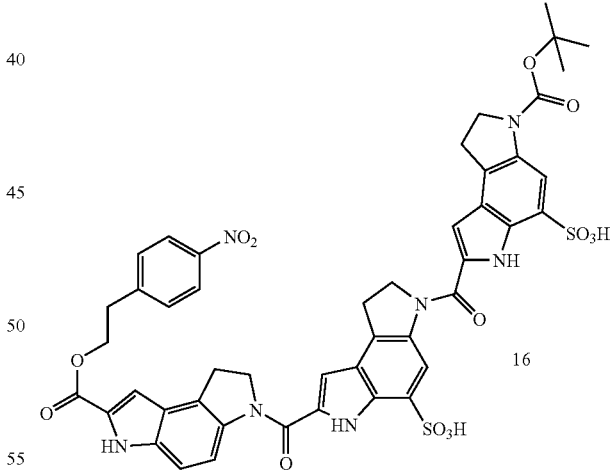

16

Compound 1-5 (n = 2, X = SO₃H) Scheme I ⇌ Compound 1-4 (n = 2, X = SO₃H) Scheme I Synthesis of 3-({3-[(tert-butyl)oxycarbonyl]-5-sulfopyrrolo[4,5-e]indolin-7-yl}carbonyl)-7-[(7-{[2-(4-nitrophenyl)ethyl]carbonyl]pyrrolo[3,2-e]indoline-5- sulfonic, ditriethylammonium salt (16)

A suspension of Compound 13 (2.1 g) (see Example 2) in 20 mL of TFA was stirred at room temperature for 1 h. TFA was evaporated and the resulting solid was washed with ether to remove residual TFA. After being dried in vacuo for 1 h, the solid was dissolved in 20 mL of anhydrous DMF in the presence of 1.0 mL of triethylamine. To this solution was added Compound 1-2 (Scheme II) (1.6 g) (see Example 1). The resulting reaction mixture was stirred overnight to give a suspension. DMF was evaporated and the solid was washed with methanol, ether and dried under vacuum to afford 2.8 g of the title Compound 16. $^1$H MNR (d6-DMSO) δ: 11.97 (s, 1H, NH), 10.39 (s, 1H, NH), 10.29 (s, 1H, NH), 8.85 (br s, 2H), 8.58 (s, 1H), 8.34 (d, J=8.7 Hz, 1H), 8.20 (d, J=8.8 Hz, 2H), 8.12 (br s, 1H), 7.67 (d, J=8.7 Hz, 2H), 7.36 (d, J=8.8 Hz, 1H), 7.22 (d, J=1 Hz, 1H), 7.12 (d, J=1 Hz, 1H), 7.09 (d, J=1 Hz, 1H), 4.70 (t, J=8 Hz, 4H), 4.58 (t, J=6.4 Hz, 2H), 4.05 (t, J=8.6 Hz, 2H), 3.50 (m, 4H), 3.28 (t, J=8.5 Hz, 2H), 3.23 (t, J=6.6 Hz, 2H), 3.09 (m, 12H), 1.53 (s, 9H) and 1.17 (t, J=7.4 Hz, 18H).

Synthesis of 3-({3-[(3-carbamoylpyrrolo[4,5-e]indo-lin-7-yl]-5-sulfopyrrolo[4, 5-e]indolin-7-yl}carbonyl)-7-[(7-{[2-(4-nitrophenyl)ethyl] oxycarbonyl}pyrrolo[3,2-indolin-3-yl)carbonyl] pyrrolo[3,2-e]indoline-5-sulforic acid, ditriethylammonium salt (Compound 1-4, n=2, X=SO$_3$H, of Scheme I))

Compound 16 (1.5 g) from above was selectively deprotected by a treatment with 26 mL of 50% TFA/CH$_2$Cl$_2$ for 2 h. The reaction was concentrated and the resultant TFA salt was washed with ether and dried under vacuum. To a suspension of the TFA salt in DMF (25 mL) was added triethylamine (0.9 mL) followed by 2,3,5,6-tetrafluorophenyl 3-carbamoylpyrrolo[4,5-e]indoline-7-carboxylate (0.8 g) (prepared from the procedure described by Lukhtanov et al. in *Bioconjugate Chem.*, 1995, 6, 418-426). The reaction mixture was stirred at room temperature for 48 h. DMF was evaporated and the residue was triturated with CH$_3$CN. The solid was stirred overnight and collected by filtration. Washing with ethyl acetate and drying under vacuum afforded 1.6 g of the tetramer (Compound 1-4, n=2, X=SO$_3$H, of Scheme I) as an off-white solid. $^1$H MNR (d6-DMSO) δ: 11.97 (s, 1H, NH), 11.55 (s, 1H, NH), 10.40 (s, 2H, 2NH), 8.85 (br s, 2H), 8.60 (s, 1H), 8.57 (s, 1H), 8.35 (d, J=8.9 Hz, 1H), 8.20 (d, J=8.7 Hz, 2H), 7.98 (d, J=9 Hz, 1H), 7.67 (d, J=8.7 Hz, 2H), 7.36 (d, J=9 Hz, 1H), 7.25 (d, J=9 Hz, 1H), 7.22 (br s, 2H), 7.09 (d, J=1 Hz, 1H), 6.99 (d, J=1 Hz, 1H), 6.11 (br s, 2H, NH$_2$), 4.70 (m, 6H), 4.58 (t, J=6 Hz, 2H), 3.99 (t, J=8.7 Hz, 2H), 3.49 (m, 6H), 3.30 (t, J=8.5 Hz, 2H), 3.23 (t, J=6 Hz, 2H); 3.09 (m, 12H), 1.16 (t, J=7.4 Hz, 18H).

Synthesis of 3-({3-[(3-carbamoylpyrrolo[4,5-e]indo-lin-7-yl]-5-sulfopyrrolo[4,5-e]indolin-7-yl}carbonyl)-7-({7-[(2,3,4,5,6-pentafluorophenyl) oxycarbonyl]pyrrolo[3,2-e]indolin]-3-yl}carbonyl) pyrrolo[3,2-e]indoline-5-sulfonic acid, ditriethylammonium salt (Compound 1-5, n=2, X=SO$_3$H, of Scheme I)

To a suspension of Compound 1-4 (n=2, X=SO$_3$H, of Scheme 1) (1.5 g) in 75 mL of DMF was added 4.5 mL of DBU. After stirring at 50° C. for 40 min, the solution was concentrated and the residue was triturated with ether (150 mL). The solid was filtered off, washed with ether and dried.

This procedure afforded 1.7 g of the free acid (di-DBU salt) as a pale yellow solid. This product was suspended in anhydrous DMF (35 mL) and treated with triethylamine (1.7 mL) followed by PEP-TFA (1.7 mL). After stirring the resulting mixture for 1 h, the solution was concentrated. To the residue was added ether to precipitate the product (Compound 1-5, n=2, X=SO$_3$H, of Scheme I). It was filtered off, washed with 50% MeOH/ether, ether and dried. The yield of the final product was 1.48 g. $^1$H MNR (d6-DMSO) δ: 12.54 (s, 1H, NH), 11.54 (s, 1H, NH), 10.41 (s, 2H, 2NH), 8.84 (br s, 2H), 8.61 (s, 1H), 8.57 (s, 1H), 8.46 (d, J=8.9 Hz, 1H), 7.98 (d, J=9 Hz, 1H), 7.60 (d, J=1 Hz, 1H), 7.44 (d, J=9 Hz, 1H), 7.25 (d, J=9 Hz, 1H), 7.23 (br s, 2H), 6.99 (d, J=1 Hz, 1H), 6.10 (br s, 2H, NH$_2$), 4.70 (m, 6H), 3.99 (t, J=8.5 Hz, 2H), 3.49 (m, 6H), 3.30 (m, 2H), 3.09 (m, 12H) and 1.16 (t, J=7.4 Hz, 18H).

Example 4

This example illustrates conjugates of the present invention to perform mismatch discrimination.

Oligonucleotide conjugates 5'-CCAAAATTAC-X$^{11}$-3' (SEQ ID NO:1), where X$^{11}$ is a minor groove binder of FIG. 1, were hybridized to different complementary targets that contain A/C mismatch at positions 5, 6, 7 and 8, relative to the attached minor groove binder.

The relative free energy difference (ΔΔG°) between match and mismatch at positions 5, 6, 7 and 8 were calculated at 50° C. and are listed in Table below. The ΔΔG° values were calculated as described in U.S. application Ser. No. 09/796,988.

| Table of ΔΔG° between match and mismatch calculated at 50° C. for different conjugates. | | | |
|---|---|---|---|
| A/C Mismatch Position | CDPI$_3$ (N) cal/mol | CDPI$_3$ (C) cal/mol | CDPI$_3$-SO$_3^-$ cal/mol |
| 5 | 5280 | 4870 | 4260 |
| 6 | 6320 | 6220 | 5160 |
| 7 | 5550 | 6240 | 5550 |
| 8 | 5510 | 5520 | 4320 |

As shown in the above Table, the CDPI$_3$—SO$_3^-$ conjugates perform comparable to the other conjugates in the Table.

In addition, the CDPI$_4$ moiety when attached to an oligonucleotide yields conjugates with aggregation properties that make it not practical to use. However, when the CDPI$_4$ is substituted with one or more SO$_3$H groups, their aggregation problems are significantly reduced such that they can be successfully used in hybridization base studies and assays.

Example 5

This example shows measured thermodynamic properties of conjugates of the present invention.

Thermodynamic properties of 3'-conjugated, where X" represents the attached minor groove binder which is either CDPI$_3$ (C), CDPI$_3$ (N) and CDPI$_4$—(SO$_3^-$)$_2$. The parameters were determined at PCR buffer, where the oligonucleotide concentration was 5×10$^{-7}$M. The sequences below were hybridized to matched complement of ODN #1. The relative free energy difference (ΔΔG°) between match and mismatch at positions 5, 6, 7 and 8 were calculated at 50° C. and plotted in FIG. 2. The bold C base in the sequences indicates the position of the C/A mismatch.

| ODN | SEQUENCES (SEQ ID NOS:2-6) |
|---|---|
| #1 | GGTTTTAATG-X" |
| #0 | GGTTTCAATG-X" |
| #2 | GGTTCTAATG-X" |
| #3 | GGTCTTAATG-X" |
| #4 | GGCTTTAATG-X" |

Figure 2:
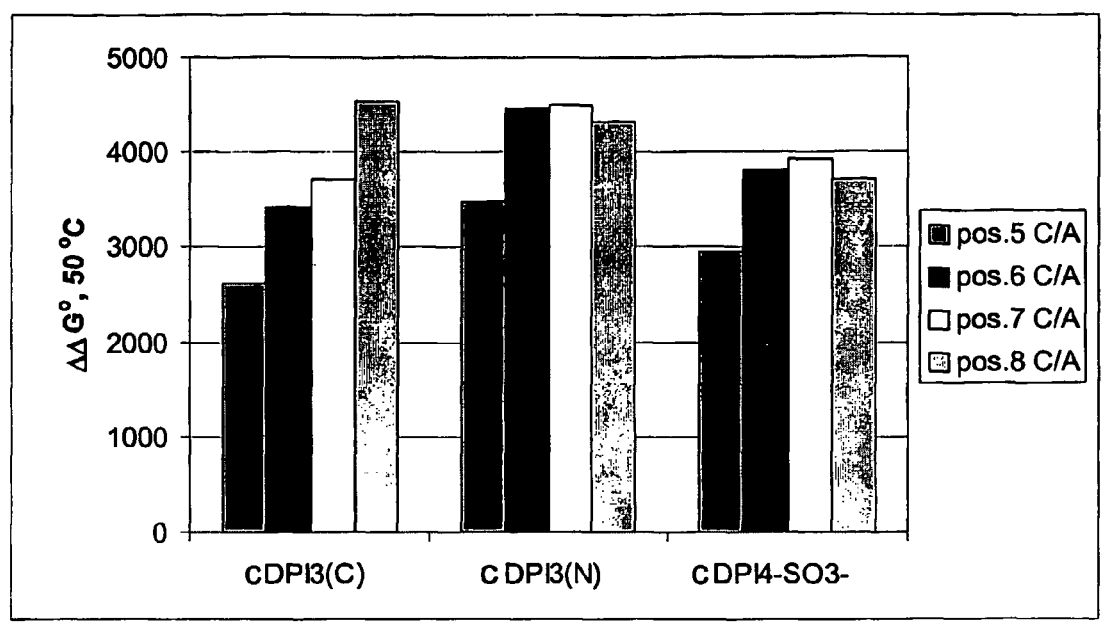
FIG. 2 shows a calculated relative free energy difference, $\Delta\Delta G°$ (cal/mol), between match and mismatch (C/A) at positions 5, 6, 7, and 8 in the conjugates at 50° C. of compounds of FIG. 1.

As shown in FIG. 2, the $CDPI_4$—$(SO_3^-)_2$ (i.e., $DPI_4$—$(SO_3^-)_2$) conjugate showed comparable mismatch discrimination than that of the other two $CDPI_3$ (i.e., $DPI_3$) conjugates. In addition, improved mismatch discrimination was observed when a mismatch is placed in the minor groove binding area in the duplex. Thus, the $CDPI_4$—$(SO_3^-)_2$ conjugate extends the useful binding area for this purpose.

All publications and patent applications cited in this specification are incorporated herein by reference in their entireties. The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An oligonucleotide-negatively charged minor groove binder conjugate comprising:
   a negatively charged minor groove binder moiety comprising:
      at least one aryl moiety, and
      at least one acidic moiety capable of ionizing under physiological conditions, wherein said acidic moiety is covalently attached to at least one of said aryl moiety and optionally comprises an acidic moiety linker;
   an oligonucleotide moiety which is covalently attached to said negatively charged minor groove binder moiety, wherein said negatively charged minor groove binder moiety is covalently attached to 3'-position, 5'-position or an internal sugar moiety of said oligonucleotide; and
   wherein the conjugate retains said at least one acidic moiety of the negatively charged minor groove binder moiety.

2. The oligonucleotide-negatively charged minor groove binder conjugate according to claim 1, wherein said negatively charged minor groove binder moiety is covalently attached to a heterocyclic base portion of said oligonucleotide moiety.

3. The oligonucleotide-negatively charged minor groove binder conjugate according to claim 1, wherein said negatively charged minor groove binder moiety comprises a plurality of said acidic moieties.

4. The oligonucleotide-negatively charged minor groove binder conjugate according to claim 3, wherein said negatively charged minor groove binder moiety comprises at least three of said acidic moieties.

5. The oligonucleotide-negatively charged minor groove binder conjugate according to claim 1, wherein said oligonucleotide comprises from about 3 to about 100 nucleotide units.

6. The oligonucleotide-negatively charged minor groove binder conjugate according to claim 1, wherein at least one of said acidic moiety is covalently attached to at least one of said aryl moiety through said acidic moiety linker.

7. The oligonucleotide-negatively charged minor groove binder conjugate according to claim 6, wherein said acidic moiety linker comprises from 1 to about 30 atoms selected from the group consisting of C, N, O, S, P and a combination thereof.

8. The oligonucleotide-negatively charged minor groove binder conjugate according to claim 7, wherein the combination of said acidic moiety and said acidic moiety linker is of the formula:

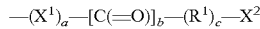

wherein
each of a, b and c is independently 0 or 1;
each $X^1$ is independently selected from the group consisting of:
(i) O,
(ii) $NR^2$, where each $R^2$ is independently selected from the group consisting of hydrogen, alkyl, cycloalkyl and a nitrogen protecting group, and
(iii) alkylene;
each $R^1$ is independently selected from the group consisting of alkylene, cycloalkylene, arylene and a combination thereof; and
each $X^2$ is independently said acid moiety.

9. The oligonucleotide-negatively charged minor groove binder conjugate according to claim 1, wherein said acidic moiety has pKa of about 6 or less.

10. The oligonucleotide-negatively charged minor groove binder conjugate according to claim 9, wherein each of said acidic moiety is independently selected from the group consisting of:
(i) $-(O)_dS(O)_eOH$, wherein d 0 or 1 and e is 1 or 2, and
(ii) $-(O)_fP(O)_g(OR^{a1})_h(OH)_i$, wherein each $R^{a1}$ is independently selected from the group consisting of alkyl, aralkyl and aryl; f is 0 or 1; each of g and h is independently 0, 1, or 2; and i is 1, 2 or 3, provided the sum of g+h+i is 2 or 3;
(iii) $-CO_2H$; and
(iv) salts thereof.

11. The oligonucleotide-negatively charged minor groove binder conjugate according to claim 1, wherein said acidic moiety is covalently attached to a phenyl moiety or a heteroatom of a heteroaryl portion of said aryl moiety, optionally through said acidic moiety linker.

12. The oligonucleotide-negatively charged minor groove binder conjugate according to claim 11, wherein said aryl moiety of negatively charged minor groove binder is selected from the group consisting of phenyl, a heteroaryl, a fused phenyl-heteroaryl, a fused heteroaryl-phenyl-heterocyclyl and a combination thereof.

13. The oligonucleotide-negatively charged minor groove binder conjugate according to claim 1 further comprising a first linker moiety, wherein said negatively charged minor groove binder moiety is covalently attached to said oligonucleotide moiety through said first linker moiety.

14. The oligonucleotide-negatively charged minor groove binder conjugate according to claim 13 further comprising a quencher moiety, wherein said quencher moiety is covalently attached to said first linker moiety.

15. The oligonucleotide-negatively charged minor groove binder conjugate according to claim 14, wherein said quencher moiety has an absorbance maximum of from about 400 nm to about 1000 nm.

16. The oligonucleotide-negatively charged minor groove binder conjugate according to claim 1 further comprising a fluorophore moiety covalently attached to said oligonucleotide moiety, wherein said fluorophore moiety is covalently attached to said oligonucleotide moiety through an optional second linker moiety.

17. The oligonucleotide-negatively charged minor groove binder conjugate according to claim 16, wherein the emission wavelength of said fluorophore moiety is from about 400 to about 1000 nm.

18. The oligonucleotide-negatively charged minor groove binder conjugate according to claim 1 of the formula:

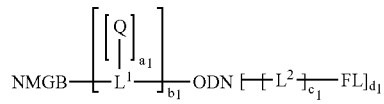

wherein
NMGB is said negatively charged minor groove binder;
ODN is said oligonucleotide;
FL is a fluorophore;
Q is a quencher;
$L^1$ is a first linker comprising a chain of from 3 to about 100 atoms selected from the group consisting of C, N, 0, S, P and combinations thereof;
$L^2$ is a second linker comprising a chain of from 1 to about 30 atoms selected from the group consisting of C, N, O, S, P and combinations thereof; and
each of $a_1$, $b_1$, $c_1$ and $d_1$ is independently 0 or 1.

19. The oligonucleotide-negatively charged minor groove binder conjugate according to claim 18, wherein NMGB moiety is of the formula:

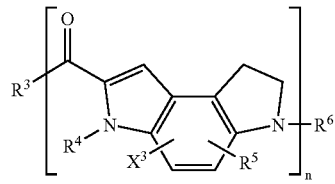

wherein
n is an integer from 2 to 10;
$R^3$ is selected from the group consisting of:
(a) alkoxy,
(b) aryloxy,
(c) $R^a$—O—$L^3$—$N(R^b)$—, where $L^3$ is a third linker comprising a chain of from 3 to 20 atoms selected from the group consisting of C, N, O, S, P and combinations thereof; and $R^a$ is hydrogen, a hydroxyl protecting group or attached to $L^1$; and $R^b$ is hydrogen, alkyl, cycloalkyl or a nitrogen protecting group,
(d) a moiety of the formula:

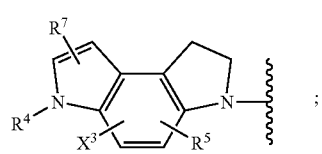

where
each of $X^3$ is independently selected from the group consisting of hydrogen, alkyl, alkoxy, halide, cyano, nitro, the acidic moiety optionally comprising an acidic linker and $-NR^{b1}-C(=O)R^c$, where each $R^{b1}$ is hydrogen, alkyl, cycloalkyl or a nitrogen protecting group, each $R^c$ is independently selected from the group consisting of hydrogen, alkyl, and cycloalkyl;
each of $R^4$ is independently selected from the group consisting of:
(a) hydrogen,
(b) alkyl,
(c) the acidic moiety optionally comprising an acidic moiety linker,
(d) —C(=O)$R^{71}$, where $R^{71}$ is hydrogen, alkyl, hydroxy or alkoxy,
(e) —NR'R", where each of R' and R" is independently hydrogen or alkyl, and
(f) -alkylene)-O$R^{72}$, where $R^{72}$ is hydrogen or alkyl,
each $R^5$ is independently selected from the group consisting of:
(a) hydrogen,
(b) alkyl,
(c) alkoxy,
(d) cycloalkyl,
(e) halide,
(f) cyano,
(g) nitro,
(h) —[$X^4$]$_{m1}$—C(=O)—[O]$_{m2}$—$R^8$, where each m1 and m2 is independently 0 or 1, $X^4$ is O, $NR^{b1}$, where $R^{b1}$ is hydrogen, alkyl, cycloalkyl or a nitrogen protecting group and $R^8$ is hydrogen, alkyl or cycloalkyl, provided when m2 is 1, $R^8$ is alkyl or cycloalkyl, and
(i) —C(=O)—$NR^eR^f$, where each of $R^e$ and $Rf$ is independently hydrogen, alkyl, cycloalkyl and a nitrogen protecting group,
(j) the acidic moiety optionally comprising an acidic moiety linker,
(k) —NR'R", where each of R' and R" is independently hydrogen or alkyl, and
(l) -(alkylene)-O$R^{72}$, where $R^{72}$ is hydrogen or alkyl;
each of $R^6$ and $R^7$ is selected from the group consisting of:
(a) hydrogen,
(b) alkyl,
(c) cycloalkyl,
(d) -$L^x$-$Z^x$, where $L^x$ is a linker comprising from 3 to 20 atoms selected from the group consisting of C, N, O, S, P and combinations thereof; $Z^x$ is hydrogen, a protecting group, a solid support or a point of attachment to said first linker $L^1$,
(e) the acidic moiety optionally comprising an acidic moiety linker, and
(f) a moiety of the formula -($Z^1$)$_j$-C(=O)—($R^{10}$)$_k$—[C(=O)]$_l$—$R^{11}$,
where
each of j, k and l is independently 0 or 1;
each $Z^1$ is independently selected from the group consisting of O, $NR^{12}$ and alkylene;
each $R^{10}$ is independently selected from the group consisting of alkylene and cycloalkylene;
each $R^{11}$ is independently selected from the group consisting of alkyl, alkoxy, aryloxy, —$NR^{13}R^{14}$, —$NR^{15}$—$NR^{16}R^{17}$, hydroxyalkyl and thioalkyl; and
each of $R^{12}$, $R^{13}$, $R^{14}$, $R^{15}$, $R^{16}$, and $R^{17}$ is independently selected from the group consisting of hydrogen, alkyl, cycloalkyl and a nitrogen protecting group;
(g) —NR'R", where each of R' and R" is independently hydrogen or alkyl;
(h) -(alkylene)-O$R^{72}$, where $R^{72}$ is hydrogen or alkyl; and
(i) —CHO provided at least one of $X^3$, $R^4$, $R^6$, or $R^7$ comprises said acidic moiety optionally comprising said acidic moiety linker, and provided that one of $R^3$, $R^6$, $R^7$ and $R^a$ is a point of attachment to said first linker $L^1$.

20. The oligonucleotide-negatively charged minor groove binder conjugate according to claim 18, wherein NMGB moiety is of the formula:

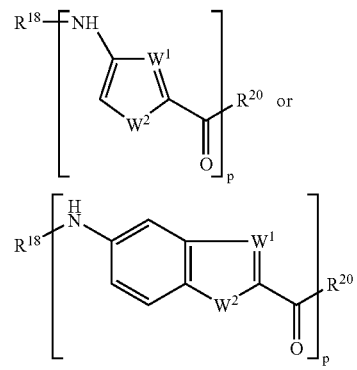

wherein
$W^1$ is N or $CR^{x30}$, where $R^{x30}$ is hydrogen, alkyl, or hydroxy;
$W^2$ is $NR^{19}$, S or O;
p is an integer from 2 to 12;
each $R^{19}$ is independently selected from the group consisting of:
(a) hydrogen,
(b) alkyl,
(c) a nitrogen protecting group, and
(b) said acidic moiety optionally comprising an acidic moiety linker;
each of $R^{18}$ and $R^{20}$ is independently selected from the group consisting of:
(a) hydrogen,
(b) alkyl,
(c) cycloalkyl,
(d) said acidic moiety; and
(e) -($Z^1$)$_j$-C(=O)—($R^{10}$)$_k$—[C(=O)]$_l$—$R^{11}$,
where
each of j, k and l is independently 0 or 1;
each $Z^1$ is independently selected from the group consisting of O, $NR^{12}$ and alkylene;
each $R^{10}$ is independently selected from the group consisting of alkylene and cycloalkylene;
each $R^{11}$ is independently selected from the group consisting of alkyl, alkoxy, aryloxy, —$NR^{13}R^{14}$, —$NR^{15}$—$NR^{16}R^{17}$, hydroxyalkyl and thioalkyl; and
each of $R^{12}$, $R^{13}$, $R^{14}$, $R^{15}$, $R^{16}$, and $R^{17}$ is independently selected from the group consisting of hydrogen, alkyl, cycloalkyl and a nitrogen protecting group;
provided at least one of $R^{18}$, $R^{19}$ or $R^{20}$ is said acidic moiety, optionally comprising said acidic moiety linker, and provided that one of $R^{18}$ and $R^{20}$ is a point of attachment to said first linker $L^1$.

21. The oligonucleotide-negatively charged minor groove binder conjugate according to claim 20, wherein NMGB moiety is of the formula:

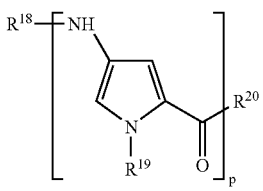

wherein
p, $R^{18}$, $R^{19}$ and $R^{20}$ are those defined in claim 20.

22. The oligonucleotide-negatively charged minor groove binder conjugate according to claim 18, wherein NMGB moiety is of the formula:

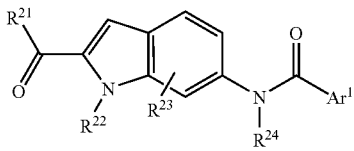

wherein
$R^{21}$ is an optionally substituted aryl-heterocyclyl;
each of $R^{22}$ and $R^{24}$ is independently selected from the group consisting of hydrogen, alkyl, cycloalkyl and a nitrogen protecting group;
$Ar^1$ is optionally substituted aryl moiety; and
$R^{23}$ is selected from the group consisting of hydrogen and said acidic moiety optionally comprising said acidic moiety linker,
provided when $R^{23}$ is hydrogen at least one of $Ar^1$ or $R^{21}$ is substituted with said acidic moiety optionally comprising said acidic moiety linker, and provided that one of $R^{21}$, $R^{22}$, $R^{23}$ and $R^{24}$ is a point of attachment to said first linker $L^1$.

23. The oligonucleotide-negatively charged minor groove binder conjugate according to claim 18, wherein said quencher moiety, Q, is of the formula:

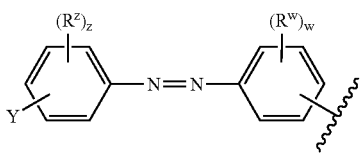

wherein
Y is selected from the group consisting of substituted phenyldiazenyl, nitro and —$NR^{50}R^{51}$, where each of $R^{50}$ and $R^{51}$ is independently selected from the group consisting of hydrogen, alkyl, cycloalkyl and a nitrogen protecting group;
each of z and w is independently an integer from 0 to 4;
each $R^z$ is independently selected from the group consisting of hydrogen, nitro, cyano, halide and —$S(O)_{aa}NR^{52}R^{53}$, where aa is 0, 1 or 2 and each of $R^{52}$ and $R^{53}$ is independently selected from the group consisting of hydrogen, alkyl, cycloalkyl and a nitrogen protecting group, or two adjacent $R^z$'s and carbon atom to which they are attached to forms a five- or six-membered ring having from zero to three heteroatoms as ring members; and each $R^w$ is independently selected from the group consisting of alkoxy, halide and —$NR^{54}$—$C(=O)R^{55}$, where $R^{54}$ is selected from the group consisting of hydrogen, alkyl and a nitrogen protecting group, and $R^{55}$ is selected from the group consisting of hydrogen, alkyl and cycloalkyl, or two adjacent $R^w$'s and carbon atom to which they are attached to forms a five- or six-membered ring having from zero to three heteroatoms as ring members.

24. The oligonucleotide-negatively charged minor groove binder conjugate according to claim 23, wherein said quencher moiety is of the formula:

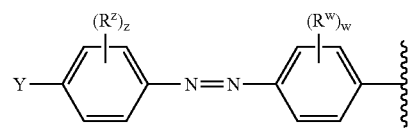

wherein
w, z, $R^w$ and $R^z$ are those defined in claim 24; and
Y is selected from the group consisting of nitro and —$N(CH_3)_2$.

25. The oligonucleotide-negatively charged minor groove binder conjugate according to claim 23, wherein said quencher moiety is of the formula:

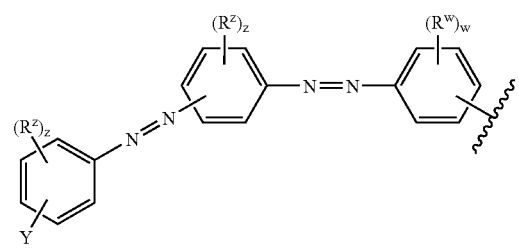

wherein
Y is selected from the group consisting of nitro and —$NR^{50}R^{51}$; and
w, z, $R^w$, $R^z$, $R^{50}$ and $R^{51}$ are those defined in claim 23.

26. The oligonucleotide-negatively charged minor groove binder conjugate according to claim 18, wherein said fluorophore has emission wavelength of from about 400 to about 1000 nm.

27. The oligonucleotide-negatively charged minor groove binder conjugate according to claim 26, wherein said fluorophore, FL, is selected from the group consisting of a derivative of fluoresceine, cyanine, resorufin and coumarin.

28. The oligonucleotide-negatively charged minor groove binder conjugate according to claim 27, wherein said fluorophore, FL, is a coumarin derivative selected from the group consisting of:

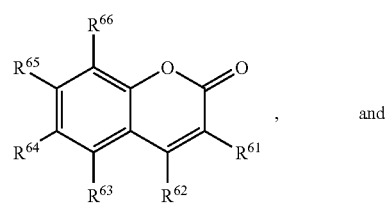

, and

-continued

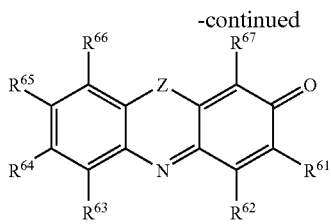

wherein
each of $R^{61}$, $R^{62}$, $R^{63}$, $R^{64}$, $R^{65}$, $R^{66}$ and $R^{67}$ is independently selected from the group consisting of hydrogen, halide, nitro, cyano, —$SO_3R^{70}$, —$SO_2N(R^{70})_2$, —$C(=O)OR^{70}$, —$C(=O)N(R^{70})_2$, —CNS, —$OR^{70}$, —$C(=O)R^{70}$, —$SR^{70}$, —$NHC(O)R^{70}$, —$CF_3$, —$N(R^{70})_2$, wherein each $R^{70}$ is independently selected from the group consisting of hydrogen, $C_1$-$C_8$ alkyl, aryl and a protecting group compatible with oligonucleotide synthesis, or two adjacent groups of $R^{61}$ through $R^{66}$ together with the carbon atoms to which they are attached form a five- or six-membered ring having from zero to three heteroatoms as ring member; and Z is O or S;

provided that at least one of $R^{61}$ through $R^{67}$ is a point of attachment to said second linker $L^2$ or to said oligonucleotide ODN.

29. The oligonucleotide-negatively charged minor groove binder conjugate according to claim 18, wherein $L^1$ comprises a moiety selected from the group consisting of:

(a)

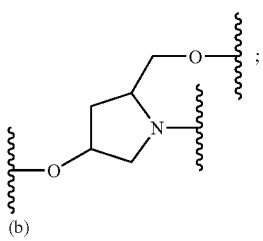

(b)

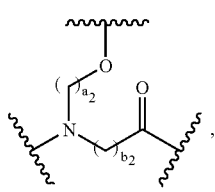

wherein $a_2$ and $b_2$ are independently an integer from 2 to 10;

(c)

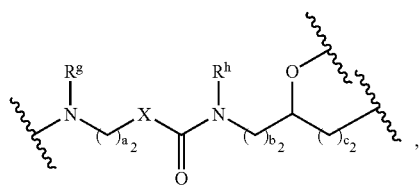

wherein $a_2$, $b_2$ and $c_2$ are independently an integer from 2 to 10, X is O, $CH_2$ or $NR^i$ and each of $R^g$, $R^h$ and $R^i$ is independently hydrogen, alkyl, cycloalkyl or a nitrogen protecting group; and (d)

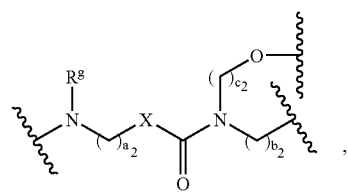

wherein $a_2$, $b_2$ and $c_2$ are independently an integer from 2 to 10, X is O, $CH_2$ or $NR^i$ and each of $R^g$ and $R^i$ is independently hydrogen, alkyl, cycloalkyl or a nitrogen protecting group.

30. The oligonucleotide-negatively charged minor groove binder conjugate according to claim 29 of the formula:

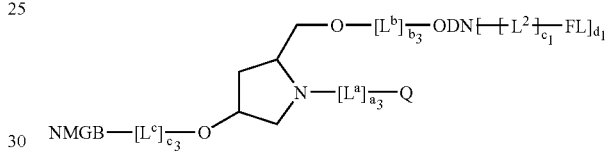

wherein
$c_1$, $d_1$, $L^2$, Q, ODN, NMGB and FL are those defined in claim 18;
each of $a_3$, $b_3$ and $c_3$ is 0 or 1; and
each of $L^a$, $L^b$ and $L^c$ is independently a linker comprising an acyclic chain of from 1 to about 10 atoms, wherein each atom of the acyclic chain is independently selected from the group consisting of C, N, O, S and P.

31. The oligonucleotide-negatively charged minor groove binder conjugate according to claim 29 of the formula:

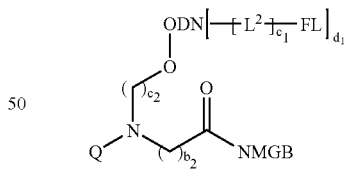

wherein
$c_1$, $d_1$, $L^2$, FL, Q, ODN and NMGB are those defined in claim 18; and
$a_2$ and $b_2$ are those defined in claim 29.

32. A pharmaceutical composition comprising an oligonucleotide-negatively charged minor groove binder conjugate of claim 1.

* * * * *